US008725556B2

(12) United States Patent
Strawmyer et al.

(10) Patent No.: US 8,725,556 B2
(45) Date of Patent: May 13, 2014

(54) WAGE INDEX NAVIGATOR SYSTEM

(75) Inventors: Mark A. Strawmyer, Fishers, IN (US); Andrew Jay Sutton, Zionsville, IN (US)

(73) Assignee: Crowe Horwath LLP, South Bend, IN (US)

( * ) Notice: Subject to any disclaimer, the term of this patent is extended or adjusted under 35 U.S.C. 154(b) by 191 days.

(21) Appl. No.: 13/151,176

(22) Filed: Jun. 1, 2011

(65) Prior Publication Data

US 2012/0016689 A1   Jan. 19, 2012

Related U.S. Application Data

(60) Provisional application No. 61/350,283, filed on Jun. 1, 2010.

(51) Int. Cl.
| G06Q 10/00 | (2012.01) |
| G06Q 10/06 | (2012.01) |
| G06Q 10/10 | (2012.01) |

(52) U.S. Cl.
CPC .......... G06Q 10/06393 (2013.01); *G06Q 10/00* (2013.01); *G06Q 10/105* (2013.01); *G06Q 10/1053* (2013.01)
USPC ...................................................... 705/7.39

(58) Field of Classification Search
CPC ............ G06Q 10/05693; G06Q 10/00; G06Q 10/105; G06Q 10/1053
See application file for complete search history.

(56) References Cited

U.S. PATENT DOCUMENTS

| 5,937,387 | A  * | 8/1999  | Summerell et al. ................ 705/2 |
| 6,401,079 | B1 * | 6/2002  | Kahn et al. ...................... 705/30 |
| 7,054,864 | B1 * | 5/2006  | Toomey ................................ 1/1 |
| 7,676,428 | B2 * | 3/2010  | VanKirk et al. .................. 705/38 |
| 8,001,021 | B1 * | 8/2011  | Quinn et al. ..................... 705/31 |
| 8,301,519 | B2 * | 10/2012 | Bang et al. ....................... 705/30 |
| 2003/0004847 | A1 * | 1/2003 | Calderaro et al. .............. 705/36 |
| 2003/0028421 | A1 * | 2/2003 | Kobayashi ....................... 705/11 |
| 2003/0177140 | A1 * | 9/2003 | Debard et al. ............. 707/104.1 |
| 2004/0064390 | A1 * | 4/2004 | Pullen ............................. 705/35 |
| 2005/0160033 | A1 * | 7/2005 | VanKirk et al. .................. 705/38 |
| 2005/0165634 | A1 * | 7/2005 | Rimsky ........................... 705/10 |
| 2005/0283397 | A1 * | 12/2005 | Rimsky .......................... 705/11 |
| 2006/0010121 | A1 * | 1/2006 | Hotz et al. ........................ 707/4 |
| 2007/0266054 | A1 * | 11/2007 | Stephens et al. ............. 707/200 |
| 2009/0076987 | A1 * | 3/2009 | Chmura et al. ................. 706/11 |
| 2012/0010907 | A1 * | 1/2012 | Doelling et al. .................. 705/4 |
| 2012/0109792 | A1 * | 5/2012 | Eftekhari et al. ............... 705/31 |

* cited by examiner

*Primary Examiner* — Brett Feeney
(74) *Attorney, Agent, or Firm* — Anthony P. Filomena; Taft Stettinius & Hollister LLP

(57) ABSTRACT

A healthcare wage index reporting method and system providing questions and tasks to collect information for filling out a wage index and occupational mix report; receiving responses; processing the responses to complete the report; checking the responses to detect errors; generating error notices; tracking progress; and generating a completed report for submission. Electronic data files, including PUFs, can be imported to complete the report, or to pre-populate responses, and the system can generate notifications of differences between the report and the imported file. A dashboard can display progress, and current results. The system can save supporting documents, and supply templates for supporting information. The system can generate prompts based on responses, and determine future questions based on past responses. The system can generate various user-requested reports and can include bulletin board functionality.

33 Claims, 45 Drawing Sheets

```
Provider Number                                              150084
Provider Name                                                     0
Fiscal Year Salary - Overall (line 1, 21-35)                             $  -
Salary - CRNA (lines 2 & 3)                                  $  -
Salary - Physicians (lines 4, 4.01, 5, 5.01, 10, 10.01)      $  -
Salary - Interns & Residents (lines 6)                       $  -
Salary - Home office (lines 7, 11, 12, 12.01)                $  -
Salary - Excluded areas (lines 8, 8.01)                      $  -
Salary - Contract labor (lines 6.01, 9, 9.01, 9.02)          $  -
Salary - Wage-related costs (lines 13-20)                    $  -
Hours - All (except lines 13-20)                             $  -
```

FIG. 25

Hospital Name
Provider Number
Fiscal Year Ended (mm/dd/yyyy)

| Adjustment Reference | Line # | Column # | Line Description | Initial Value | Adjustment | Proposed Amount |
|---|---|---|---|---|---|---|
| | 1 | 2 | Total salaries | - | - | - |
| | 1 | 4 | Total salaries | - | - | - |
| | 2 | 1 | Non-physician anesthetist Part A | - | - | - |
| | 2 | 2 | Non-physician anesthetist Part A | - | - | - |
| | 2 | 4 | Non-physician anesthetist Part A | - | - | - |

FIG. 27

Enter Provider #  150084
Provider Name
Fiscal Year

|  |  | Amount Reported 1 | Reclass of Salaries 2 | (Col 1 + Col 2) Adjusted Salaries 3 | Paid Hours Related to Salary 4 | (Col 3/Col 4) Average Hourly Wage 5 |
|---|---|---|---|---|---|---|
| Part II - Wage Data |  Salaries |  |  |  |  |  |
| 1 | Total salaries | 291,861,919 |  | 291,861,919 | 9,655,478 | 30.23 |
| 2 | Non-physician anestheist Part A | - |  | - | - | - |
| 3 | Non-physician anestheist Part B | - |  | - | - | - |
| 4 | Physician salaries - Part A | 1,214,014 |  | 1,214,014 | 13,728 | 88.43 |
| 4.01 | Teaching physician salaries | 3,352,000 |  | 3,352,000 | 55,850 | 60.02 |
| 5 | Physician salaries - Part B | 14,090,673 |  | 14,090,673 | 130,081 | 108.32 |
| 5.01 | Non-physician Part B | - |  | - | - | - |
| 6 | Interns & residents (in approved program) | 6,147,354 |  | 6,147,354 | 253,826 | 24.22 |
| 6.01 | Contract services, I&R | - |  | - | - | - |
| 7 | Home office personnel | - |  | - | - | - |
| 8 | SNF | 972,693 |  | 972,693 | 46,339 | 20.99 |
| 8.01 | Excluded area salaries | 26,192,849 |  | 26,192,849 | 885,789 | 29.57 |
|  | Other Wages & Related Costs |  |  |  |  |  |
| 9 | Contract labor | 1,454,968 |  | 1,454,968 | 25,021 | 58.15 |
| 9.01 | Pharmacy services under contract | - |  | - | - | - |
| 9.02 | Laboratory services under contract | - |  | - | - | - |
| 9.03 | Management & Administrative under contract | - |  | - | - | - |
| 10 | Contract labor - physician - Part A | - |  | - | - | - |
| 10.01 | Teaching physicians under contract | - |  | - | - | - |
| 11.00 | Home office salaries & wage related costs | 33,303,101 |  | 33,303,101 | 806,581 | 41.29 |
| 12.00 | Home office: physician - Part A | - |  | - | - | - |
| 12.01 | Teaching physician salaries | - |  | - | - | - |
|  | Wage-Related Costs |  |  |  |  |  |
| 13 | Wage-related costs (core) | 48,613,116 |  | 48,613,116 |  |  |
| 14 | Wage-related costs (other) | - |  | - |  |  |
| 15 | Excluded areas | 5,495,404 |  | 5,495,404 |  |  |
| 16 | Non-physician anestheist Part A | - |  | - |  |  |
| 17 | Non-physician anestheist Part B | - |  | - |  |  |
| 18 | Physician Part A | 155,709 |  | 155,709 |  |  |
| 18.01 | Part A teaching physicians | 487,676 |  | 487,676 |  |  |
| 19 | Physician Part B | 1,713,106 |  | 1,713,106 |  |  |
| 19.01 | Wage-related costs (RHC/FQHC) | - |  | - |  |  |
| 20 | Interns & residents (in approved program) | 1,420,836 |  | 1,420,836 |  |  |
|  | Overhead Costs - Direct Salaries |  |  |  |  |  |
| 21 | Employee Benefits | 11,087,238 |  | 11,087,238 | 231,321 | 47.93 |
| 22 | Administrative & General | 47,609,242 |  | 47,609,242 | 1,331,862 | 35.75 |
| 22.01 | Administrative & General under contract | - |  | - | - | - |
| 23 | Maintenance & Repairs | - |  | - | - | - |
| 24 | Operation of Plant | 5,582,307 |  | 5,582,307 | 268,254 | 20.81 |
| 25 | Laundry & Linen Service | 266,455 |  | 266,455 | 20,265 | 13.15 |
| 26 | Housekeeping | 4,925,828 |  | 4,925,828 | 386,911 | 12.73 |
| 26.01 | Housekeeping under contract | - |  | - | - | - |
| 27 | Dietary | 2,041,186 |  | 2,041,186 | 146,313 | 13.95 |
| 27.01 | Dietary under contract | - |  | - | - | - |
| 28 | Cafeteria | 2,503,921 |  | 2,503,921 | 182,366 | 13.73 |
| 29 | Maintenance of Personnel | - |  | - | - | - |
| 30 | Nursing Administration | 7,316,847 |  | 7,316,847 | 254,643 | 28.73 |
| 31 | Central Services and Supply | 281,703 |  | 281,703 | 36,853 | 7.64 |

FIG. 26

Provider Number # 150084
Provider Name
Fiscal Year

Part II - Wage Data

| | | Amount Reported 1 | Reclass of Salaries 2 | (Col 1 + Col 2) Adjusted Salaries 3 | Paid Hours Related to Salary 4 | (Col 3/Col 4) Average Hourly Wage 5 |
|---|---|---|---|---|---|---|
| | Salaries | | | | | |
| 1 | Total salaries | 291,861,919 | | 291,861,919 | 9,655,478 | 30.23 |
| 2 | Non-physician anestheist Part A | - | | - | - | - |
| 3 | Non-physician anestheist Part B | - | | - | - | - |
| 4 | Physician salaries - Part A | 1,214,014 | | 1,214,014 | 13,728 | 88.43 |
| 4.01 | Teaching physician salaries | 3,352,000 | | 3,352,000 | 55,850 | 60.02 |
| 5 | Physician salaries - Part B | 14,090,673 | | 14,090,673 | 130,081 | 108.32 |
| 5.01 | Non-physician Part B | - | | - | - | - |
| 6 | Interns & residents (in approved program) | 6,147,354 | | 6,147,354 | 253,826 | 24.22 |
| 6.01 | Contract services, I&R | - | | - | - | - |
| 7 | Home office personnel | - | | - | - | - |
| 8 | SNF | 972,693 | | 972,693 | 46,339 | 20.99 |
| 8.01 | Excluded area salaries | 26,192,849 | | 26,192,849 | 885,789 | 29.57 |
| | Other Wages & Related Costs | | | | | |
| 9 | Contract labor | 1,454,968 | | 1,454,968 | 25,021 | 58.15 |
| 9.01 | Pharmacy services under contract | - | | - | - | - |
| 9.02 | Laboratory services under contract | - | | - | - | - |
| 9.03 | Management & Administrative under contract | - | | - | - | - |
| 10 | Contract labor - physician - Part A | - | | - | - | - |
| 10.01 | Teaching physicians under contract | - | | - | - | - |
| 11.00 | Home office salaries & wage related costs | 33,303,101 | | 33,303,101 | 806,581 | 41.29 |
| 12.00 | Home office: physician - Part A | - | | - | | |
| 12.01 | Teaching physician salaries | - | | - | | |
| | Wage-Related Costs | | | | | |
| 13 | Wage-related costs (core) | 48,613,116 | | 48,613,116 | | |
| 14 | Wage-related costs (other) | - | | - | | |
| 15 | Excluded areas | 5,495,404 | | 5,495,404 | | |
| 16 | Non-physician anestheist Part A | - | | - | | |
| 17 | Non-physician anestheist Part B | - | | - | | |
| 18 | Physician Part A | 155,709 | | 155,709 | | |
| 18.01 | Part A teaching physicians | 487,676 | | 487,676 | | |
| 19 | Physician Part B | 1,713,106 | | 1,713,106 | | |
| 19.01 | Wage-related costs (RHC/FQHC) | - | | - | | |
| 20 | Interns & residents (in approved program) | 1,420,836 | | 1,420,836 | | |
| | Overhead Costs - Direct Salaries | | | | | |
| 21 | Employee Benefits | 11,087,238 | | 11,087,238 | 231,321 | 47.93 |
| 22 | Administrative & General | 47,609,242 | | 47,609,242 | 1,331,862 | 35.75 |
| 22.01 | Administrative & General under contract | - | | - | - | - |
| 23 | Maintenance & Repairs | - | | - | - | - |
| 24 | Operation of Plant | 5,582,307 | | 5,582,307 | 268,254 | 20.81 |
| 25 | Laundry & Linen Service | 266,455 | | 266,455 | 20,265 | 13.15 |
| 26 | Housekeeping | 4,925,828 | | 4,925,828 | 386,911 | 12.73 |
| 26.01 | Housekeeping under contract | - | | - | - | - |
| 27 | Dietary | 2,041,186 | | 2,041,186 | 146,313 | 13.95 |
| 27.01 | Dietary under contract | - | | - | - | - |
| 28 | Cafeteria | 2,503,921 | | 2,503,921 | 182,366 | 13.73 |
| 29 | Maintenance of Personnel | - | | - | - | - |
| 30 | Nursing Administration | 7,316,847 | | 7,316,847 | 254,643 | 28.73 |
| 31 | Central Services and Supply | 281,703 | | 281,703 | 36,853 | 7.64 |
| 32 | Pharmacy | 9,933,725 | | 9,933,725 | 282,294 | 35.19 |
| 33 | Medical Records & Medical Records library | 3,596,027 | | 3,596,027 | 201,491 | 17.85 |

FIG. 28

| | LAKE COUNTY RECLASSIFICATION FINANCIAL IMPACT SUMMARY | | | | | | |
|---|---|---|---|---|---|---|---|
| | | | W/OUT ReClass | | W/OUT ReClass | | |
| | | | Index of 1.0348 | | Index of 1.0701 | | GAIN |
| Midwestern Regional | | | | | | | |
| | Inpatient | | $ 4,005,564 | | $ 4,155,461 | | $ 149,897 |
| | Outpatient | | | | | | $ 94,045 |
| | | | | | | | |
| Advocate Good Shephard | | | | | | | |
| | Inpatient | | $ 21,440,045 | | $ 21,966,139 | | $ 526,094 |
| | Outpatient | | | | | | $ 113,490 |
| | | | | | | | |
| Condel | | | | | | | |
| | Inpatient | | $ 43,382,166 | | $ 44,444,764 | | $ 1,062,598 |
| | Outpatient | | | | | | $ 176,779 |
| | | | | | | | |
| Lake Forest Hospital | | | | | | | |
| | Inpatient | | $ 14,059,872 | | $ 14,404,974 | | $ 345,102 |
| | Outpatient | | | | | | $ 133,995 |
| | | | | | | | |
| Provena St. Therese | | | | | | | |
| | Inpatient | | $ 14,303,598 | | $ 14,822,456 | | $ 518,858 |
| | Outpatient | | | | | | $ 44,391 |
| | | | | | | | |
| Victory | | | | | | | |
| | Inpatient | | $ 24,224,159 | | $ 25,095,317 | | $ 871,158 |
| | Outpatient | | | | | | $ 65,271 |
| | | | | | | | |
| TOTAL INPATIENT IMPACT | | | | | | | $ 3,473,707 |
| TOTAL OUTPATIENT IMPACT | | | | | | | $ 627,971 |
| GRAND TOTAL | | | | | | | $ 4,101,678 |

FIG. 29

CBSA 16974

| | Provider Name | FFY 2009 AHW (August 2008 Final Rule) | % of CBSA, Per FFY2009 Final Rule | Obvious Negative Adjustments | |
|---|---|---|---|---|---|
| | | | | Negative Wi Adjustments, AHW Impact | Negative Impact on CBSA |
| | Provena | | | | |
| 140174 | MERCY CENTER FO HEALTH CARE SERVICES | $33.94 | 0.80% | $ (0.46) | $ (0.0037) |
| 140007 | PROVENA ST. JOSEPH MEDICAL CENTER | $32.44 | 1.86% | $ (0.62) | $ (0.0114) |
| 140217 | ST. JOSEPH HOSPITAL | $33.22 | 0.77% | $ (0.43) | $ (0.0033) |
| | Resurrection | | | | |
| 140117 | RESURRECTION MEDICAL CENTER | $28.58 | 1.73% | $ (1.07) | $ (0.0182) |
| 140224 | SAINT JOSEPH HOSPITAL & HLTH CR CENTER | $30.72 | 1.06% | $ (0.19) | $ (0.0020) |
| 140049 | WEST SUBURBAN HOSPITAL MED CENTER | $32.02 | 1.06% | $ (0.27) | $ (0.0030) |
| | Rush | | | | |
| 140119 | RUSH-PRESBYTERIAN-ST LUKES MED CTR | $34.56 | 3.80% | $ (2.72) | $ (0.1057) |
| | Freestanding Hospitals | | | | |
| 140124 | COOK COUNTY HOSPITAL | $38.00 | 4.83% | $ (2.73) | $ (0.1318) |
| 140200 | EU/HURST MEMORIAL HOSPITAL | $31.87 | 1.81% | $ (0.49) | $ (0.0088) |

MATCH LINE TO FIG. 31B

FIG. 31A

| Negative Wi impact on Reimbursement | Positive Wage Index Adjustments ||| Total Wage Index Adjustments |||||
|---|---|---|---|---|---|---|---|
| | Positive Wi Adjustments, AHW Impact | Positive Impact on CBSA | Positive Wi impact on Reimbursement | Total Estimated Wi Review AHW Impact | Impact to CBSA AWi | Current Reimb Impact Re??? Hosp Impact Only* | Current Reimbursement Impact* |
| | | | | | | Incr. of $0.06 | Incr. of $0.06 |
| $ (455,863) | $ 1.84 | $ 0.0148 | $ 288,568 | $ 1.38 | $ 0.0111 | $ 27,748 | $ 27,261 |
| $ (1,367,588) | $ 0.70 | $ 0.0130 | $ 868,703 | $ 0.08 | $ 0.0016 | $ 83,244 | $ 83,284 |
| $ (547,035) | $ 0.80 | $ 0.0062 | $ 347,481 | $ 0.37 | $ 0.0029 | $ 33,296 | $ 33,314 |
| $ (1,641,106) | $ 4.24 | $ 0.0731 | $ 1,042,444 | $ 3.17 | $ 0.0549 | $ 99,893 | $ 99,941 |
| $ (820,063) | $ 0.67 | $ 0.0070 | $ 621,222 | $ 0.48 | $ 0.0051 | $ 49,946 | $ 49,970 |
| $ (638,208) | $ 0.20 | $ 0.0022 | $ 405,305 | $ (0.07) | $ (0.0008) | $ 38,547 | $ 38,566 |
| $ (2,662,831) | $ 0.99 | $ 0.0385 | $ 1,621,579 | $ (1.73) | $ (0.0672) | $ 155,389 | $ 155,463 |
| $ (547,035) | $ 1.16 | $ 0.056 | $ 347,481 | $ (1.57) | $ (0.0758) | $ 33,280 | $ 33,314 |
| $ (1,002,898) | $ 0.38 | $ 0.0069 | $ 837,049 | $ (0.11) | $ (0.0019) | $ 60,046 | $ 61,075 |

| WageIndex | | | |
|---|---|---|---|
| Provider Data | CBSA List | Fiscal Year | |

Fiscal Year [2007 ▾]  Providers [ 72 ]   Current AHW [$31.6404] Total AHW Increase
CBSA  [16974 - Chicago-Naperville-Joliet, IL ▾]   National AHW [$29.6529] Total Impact
Increase  [    ]  [Calculate] [Clear]   Current WIF [1.0670] Estimated NEW WIF

| Provider No | Provider Name | Geo CBSA | Post-Reclass CBSA | Percent CBSA | Increase AHW | Weighted Increase | Impact |
|---|---|---|---|---|---|---|---|
| 140007 | Provena Saint Joseph Medical Ca... | 16974 | | 1.69% | | | |
| 140008 | Gottlieb Memorial Hospital | 16974 | | 0.80% | | | |
| 140010 | Evanston Hospital | 16974 | | 4.54% | | | |
| 140018 | Mount Sinai Hospital | 16974 | | 1.17% | | | |
| 140029 | Rush-Copley Medical Center | 16974 | | 0.85% | | | |
| 140030 | Sherman Hospital | 16974 | | 1.43% | | | |
| 140048 | Advocate Trinity Hospital | 16974 | | 0.77% | | | |
| 140049 | West Surburban Medical Center | 16974 | | 1.07% | | | |
| 140051 | Rush North Shore Medical Center | 16974 | | 0.90% | | | |
| 140054 | MacNeal Hospital | 16974 | | 1.33% | | | |
| 140062 | Palos Community Hospital | 16974 | | 2.02% | | | |
| 140063 | Rush Oak Park Hospital | 16974 | | 0.44% | | | |
| 140065 | Adventist La Grange Memorial Ho... | 16974 | | 0.95% | | | |
| 140068 | Roseland Community Hospital | 16974 | | 0.33% | | | |
| 140075 | Michael Reese Hospital and Medi... | 16974 | | 0.63% | | | |
| 140080 | Saint Francis Hospital | 16974 | | 0.96% | | | |
| 140082 | Weiss Memorial Hospital | 16974 | | 0.58% | | | |
| 140083 | Loretto Hospital | 16974 | | 0.28% | | | |
| 140088 | The University of Chicago Hospit... | 16974 | | 4.64% | | | |
| 140094 | Saints Mary and Elizabeth Medica... | 16974 | | 0.73% | | | |
| 140095 | Saint Anthony Hospital | 16974 | | 0.44% | | | |
| 140101 | Morris Hospital | 16974 | | 0.50% | | | |
| 140103 | Saint Bernard Hospital and Health... | 16974 | | 0.43% | | | |

1   of 88   Save  Refresh

MATCH LINE TO FIG. 33B

| Provider Wages | Discharges | Medicare Cases | AHW | CMI | Orig WIF | Orig Blended Rate | New Blended Rate | Orig Payment | New Payment |
|---|---|---|---|---|---|---|---|---|---|
| $113,592,8... | 22,265.00 | 9,859 | 30.7378 | 1.3229 | 1.0670 | $5,102... | | $66,544,302.73 | |
| $54,049,35... | 9,490.00 | 3,986 | 29.1767 | 1.4480 | 1.0670 | $5,102... | | $29,448,071.03 | |
| $303,529,1... | 31,807.00 | 13,628 | 31.8806 | 1.5072 | 1.0670 | $5,102... | | $104,798,244.10 | |
| $78,423,15... | 18,546.00 | 2,370 | 26.3533 | 1.4132 | 1.0670 | $5,102... | | $17,088,461.74 | |
| $57,412,31... | 10,554.00 | 2,693 | 30.2688 | 1.5819 | 1.0670 | $5,102... | | $21,735,336.85 | |
| $95,628,49... | 16,617.00 | 4,729 | 30.2776 | 1.5647 | 1.0670 | $5,102... | | $37,752,993.41 | |
| $51,559,43... | 11,956.00 | 3,255 | 29.3877 | 1.2695 | 1.0670 | $5,102... | | $21,083,110.93 | |
| $72,099,61... | 11,035.00 | 3,434 | 29.0976 | 1.5162 | 1.0670 | $5,102... | | $26,564,875.13 | |
| $60,689,40... | 9,796.00 | 5,631 | 30.9696 | 1.5325 | 1.0670 | $5,102... | | $44,028,815.94 | |
| $89,260,84... | 15,401.00 | 5,262 | 33.1406 | 1.4543 | 1.0670 | $5,102... | | $39,044,138.40 | |
| $135,581,2... | 18,058.00 | 10,261 | 34.1230 | 1.2106 | 1.0670 | $5,102... | | $63,378,411.93 | |
| $29,824,33... | 3,963.00 | 2,104 | 28.6559 | 1.4113 | 1.0670 | $5,102... | | $15,150,120.00 | |
| $63,985,73... | 8,891.00 | 5,244 | 30.1856 | 1.3830 | 1.0670 | $5,102... | | $37,002,908.25 | |
| $22,407,11... | 4,961.00 | 1,247 | 28.3938 | 1.1930 | 1.0670 | $5,102... | | $7,590,281.68 | |
| $42,435,01... | 9,958.00 | 2,972 | 26.2626 | 1.2757 | 1.0670 | $5,102... | | $19,344,092.33 | |
| $64,518,51... | 12,029.00 | 5,006 | 28.8791 | 1.4393 | 1.0670 | $5,102... | | $36,761,495.14 | |
| $39,420,81... | 7,543.00 | 3,151 | 28.3429 | 1.4747 | 1.0670 | $5,102... | | $23,708,445.49 | |
| $19,054,99... | 3,537.00 | 1,637 | 26.8919 | 1.0315 | 1.0670 | $5,102... | | $8,615,270.29 | |
| $310,610,4... | 25,428.00 | 7,522 | 30.5450 | 1.8434 | 1.0670 | $5,102... | | $70,746,328.76 | |
| $49,115,09... | 12,807.00 | 3,429 | 27.3841 | 1.0394 | 1.0670 | $5,102... | | $18,184,492.84 | |
| $29,589,42... | 6,265.00 | 1,138 | 28.7617 | 1.2495 | 1.0670 | $5,102... | | $7,254,868.05 | |
| $33,938,06... | 6,109.00 | 2,219 | 29.4081 | 1.1667 | 1.0670 | $5,102... | | $13,208,925.65 | |
| $29,157,52... | 7,549.00 | 1,905 | 23.6406 | 1.1933 | 1.0670 | $5,102... | | $11,598,334.14 | |

MATCH LINE TO FIG. 33A

FIG. 33B

| 16974 | Chicago-Naperville-Joliet, IL | 2003 Data FY 2006 Wage Index | | | | | | | | | |
|---|---|---|---|---|---|---|---|---|---|---|---|
| Provider # | Hospital | Teach | Benefit % | Sal & Benefits | Hours | AHW | Benefit % Rank | Sal & Bene Rank | Hours Rank | AHW Rank |
| 140007 | SAINT JOSEPH MEDICAL CA... | N | 26.12% | ######## | 3,714,595 | $30.9103 | 20 | 19 | 18 | 30 |
| 140008 | GOTTLIEB MEMORIAL HOSPITAL | N | 23.19% | $54,074,180 | 1,835,199 | $29.4650 | 39 | 43 | 43 | 46 |
| 140010 | EVANSTON HOSPITAL CORPORATION | Y | 34.10% | ######## | 9,453,813 | $32.2991 | 3 | 4 | 3 | 17 |
| 140018 | MOUNT SINAI HOSPITAL MEDICAL CENT | Y | 7.93% | $74,312,677 | 2,959,182 | $25.1138 | 71 | 30 | 24 | 68 |
| 140029 | COPLEY MEMORIAL HOSPITAL | Y | 21.17% | $57,272,072 | 1,873,133 | $30.5755 | 51 | 40 | 42 | 35 |
| 140030 | SHERMAN HOSPITAL | N | 21.39% | $96,145,989 | 3,120,078 | $30.8152 | 49 | 23 | 23 | 33 |
| 140048 | TRINITY HOSPITAL | N | 24.22% | $52,050,568 | 1,731,451 | $30.0618 | 30 | 45 | 45 | 40 |
| 140049 | WEST SUBURBAN HOSPITAL MEDICAL | Y | 25.59% | $73,984,405 | 2,479,327 | $29.8405 | 22 | 31 | 30 | 41 |
| 140051 | RUSH NORTH SHORE MEDICAL CENTER | N | 21.15% | $61,162,000 | 2,070,167 | $29.5449 | 53 | 39 | 39 | 45 |
| 140054 | MACNEAL HOSPITAL | Y | 17.49% | 492,818,449 | 2,700,247 | $34.3741 | 57 | 24 | 27 | 9 |
| 140062 | PALOS COMMUNITY HOSPITAL | N | 33.64% | ######## | 3,962,232 | $34.1643 | 4 | 12 | 17 | 10 |
| 140063 | OAK PARK HOSPITAL | N | 16.71% | $29,139,500 | 1,044,284 | $27.9039 | 64 | 61 | 60 | 59 |
| 140065 | COLUMBIA - LA GRANGE | Y | 22.70% | $62,875,292 | 2,058,443 | $30.5451 | 42 | 37 | 40 | 36 |
| 140068 | ROSELAND COMMUNITY | 0 | 0.00% | $0 | 0 | $0.0000 | 0 | 0 | 0 | 0 |
| 140075 | COLUMBIA MICHAEL REESE HOSPITAL | Y | 17.43% | $42,775,719 | 1,582,895 | $27.0237 | 59 | 50 | 47 | 60 |
| 140079 | ST. JAMES HOSPITAL & HEALTH CENTE | 0 | 0.00% | $0 | 0 | $0.0000 | 0 | 0 | 0 | 0 |
| 140080 | SAINT FRANCIS HOSPITAL | Y | 25.14% | $64,426,124 | 2,236,860 | $28.8020 | 24 | 36 | 32 | 53 |
| 140082 | JULIUS A. WEISS MEMORIAL HOSPITAL | Y | 17.99% | $40,366,417 | 1,356,878 | $29.7495 | 60 | 55 | | 43 |
| | | | | | | | 85 | | | |

FIG. 34

| PUF DATA | INITIAL PUF | | FINAL PUF | | | VARIANCE | | |
|---|---|---|---|---|---|---|---|---|
| FFY | AHW | # Hosps | AHW | # Hosps | AHW $ Var | AHW % Var | # Hosps | |
| CBSA AHW FFY 2006 | $29.74 | 71 | $29.60 | 71 | ($0.13) | -0.45% | 0 | |
| National AHW FFY 2006 | $27.87 | 3,742 | $27.37 | 3,742 | ($0.50) | -1.80% | 0 | |
| CBSA AHW FFY 2007 | $31.35 | 72 | $31.27 | 72 | ($0.08) | -0.26% | 0 | |
| National AHW FFY 2007 | $29.18 | 3,570 | $29.00 | 3,570 | ($0.18) | -0.61% | | |
| CBSA AHW Change FFY 2006 - 2007 | 5.44% | | 5.64% | | | | | |
| National AHW Change FFY 2006 - FFY 2007 | 4.70% | | 5.97% | | | | | |
| CBSA AHW FFY 2008 | $32.22 | 71 | $32.60 | 71 | $0.39 | 1.20% | 0 | |
| National AHW FFY 2008 | $30.29 | 3,569 | $30.28 | 3,569 | ($0.01) | -0.04% | 0 | |
| CBSA AHW Change FFY 2007 - FFY 2008 | 2.76% | | 4.26% | | | | | |
| National AHW Change FFY 2007 - FFY 2008 | 3.79% | | 4.40% | | | | | |
| CBSA AHW FFY 2009 | $33.75 | 72 | $33.05 | 72 | ($0.72) | -2.12% | 0 | |
| National AHW FFY 2009 | $31.46 | 3,537 | $31.65 | 3,537 | $0.19 | 0.62% | 0 | |
| CBSA AHW Change FFY 2008 - FFY 2009 | 4.76% | | 1.33% | | | | | |
| National AHW Change FFY 2008 - FFY 2009 | 3.85% | | 4.52% | | | | | |
| Est. CBSA AHW FFY 2010 (May PUF) | $35.28 | 69 | $34.65 | 69 | ($0.62) | -1.78% | 0 | |
| Est. National AHW FFY 2010 | $33.58 | 3,524 | $32.99 | 3,524 | ($0.59) | -1.75% | 0 | |
| CBSA AHW Change FFY 2009 - FFY 2010 | 4.53% | | 4.89% | | | | | |
| National AHW Change FFY 2009 - FFY 2010 | 6.75% | | 4.24% | | | | | |

FIG. 35

| Provider # | Hosp Name | CBSA | Work with EY/MCHC | FFY 10 CBSA Percentage | Comparison of May to Feb PUF ||||
|---|---|---|---|---|---|---|---|---|
| | | | | | Feb PUF AHW | May PUF AHW | Nominal Change in AHW | Percent change in AHW |
| 140033 | VISTA MEDICAL CENTER WEST | 29404 | | 0.26% | $ 32.08 | $ 32.08 | $ - | 0.00% |
| 140084 | VISTA MEDICAL CENTER - EAST | 29404 | | 3.47% | $ 32.10 | $ 32.10 | $ - | 0.00% |
| 140100 | MIDWESTERN REGIONAL MEDICAL CENTER | 29404 | | 5.95% | $ 38.57 | $ 38.57 | $ - | 0.00% |
| 140130 | LAKE FOREST HOSPITAL | 29404 | | 8.25% | $ 35.30 | $ 35.30 | $ - | 0.00% |
| 140202 | CONDELL MEDICAL CENTER | 29404 | X | 15.99% | $ 37.30 | $ 37.30 | $ - | 0.00% |
| 140291 | GOOD SHEPHERD HOSPITAL | 29404 | X | 9.39% | $ 34.16 | $ 34.16 | $ - | 0.00% |
| 520021 | UNITED HOSPITAL SYSTEM INC. | 29404 | | 8.77% | $ 28.75 | $ 28.75 | $ - | 0.00% |
| 520189 | AURORA MEDICAL CENTER KENOSHA | 29404 | | 4.71% | $ 29.13 | $ 29.13 | $ - | 0.00% |
| 140810 | EVANSTON NORTHWESTERN HEALTHCARE | 29404 | | 43.23% | $ 38.83 | $ 38.83 | $ - | 0.00% |
| Grand Total, Lake County-Kenosha County (CBSA 29404) | | | | 100.00% | $ 33.91 | $ 35.88 | $ 1.97 | 5.81% |
| 140007 | PROVENA ST JOSEPH MEDICAL CA... | 16974 | X | 1.87% | $ 33.02 | $ 33.02 | $ - | 0.00% |
| 140008 | GOTTLIEB MEMORIAL HOSPITAL | 16974 | X | 0.72% | $ 32.92 | $ 32.92 | $ - | 0.00% |
| 140010 | EVANSTON HOSPITAL CORPORATION | 16974 | X | | | | | |

| Line | Description | FFY 2010 May PUF | | | FFY 2010 February PUF | | |
|---|---|---|---|---|---|---|---|
| | | Adjusted Salaries 3 | Paid Hours Related to Salary in Col 3 4 | (Col 3/Col 4) Average Hourly Wage 5 | Adjusted Salaries 3 | Paid Hours Related to Salary in Col 3 4 | (Col 3/Col 4) Average Hourly Wage 5 |
| 1 | Total Salary (w's A, ??? 1 ln 101) | 49,537,409 | 1,887,953 | 26.25 | 49,537,409 | 1,887,953 | |
| 2 | Non-physician anestheist Part A | 0 | 0 | 0.00 | 0 | 0 | |
| 3 | Non-physician anestheist Part B | 0 | 0 | 0.00 | 0 | 0 | |
| 4 | Physician salaries - Part A (Administration) | 138,720 | 1,021 | 135.87 | 138,720 | 1,021 | |
| 4.01 | Physician salaries - Part A (Teaching & Supervision of Interns) | 0 | 0 | 0.00 | 0 | 0 | |
| 5 | Physician salaries - Part B | 156,311 | 2,128 | 73.45 | 156,311 | 2,128 | |
| 5.01 | Non-physician Part B | 0 | 0 | 0.00 | 0 | 0 | |
| 6 | Interns & residents (in approved program) | 0 | 0 | 0.00 | 0 | 0 | |
| 6.01 | Contract services, I&R | 108,680 | 2,080 | 52.25 | 108,680 | 2,080 | |
| 7 | Home office personnel | 0 | 0 | 0.00 | 0 | 0 | |
| 8 | SNF | 1,807,302 | 80,122 | 22.56 | 1,807,302 | 80,122 | |
| 8.01 | Excluded Area Salaries | 2,191,491 | 75,047 | 29.20 | 2,191,491 | 75,047 | |
| | Other Wages & Related Costs | | | | | | |
| 9 | Contract Labor | 2,101,320 | 31,632 | 66.35 | 2,101,320 | 31,632 | |
| 9.01 | Pharmacy Services Under Contract | 0 | 0 | 0.00 | 0 | 0 | |
| 9.02 | Laboratory Services Under Contract | 0 | 0 | 0.00 | 0 | 0 | |
| 9.03 | Management Contract | 0 | 0 | 0.00 | 0 | 0 | |
| 10 | Contract labor - Physician - Part A | 0 | 0 | 0.00 | 0 | 0 | |
| 10.01 | Teaching Physicians under Contract | 0 | 0 | 0.00 | 0 | 0 | |
| 11.00 | Home Office Salaries & Wage | 0 | 0 | 0.00 | 0 | 0 | |
| 12.00 | Home office Phys Part A | 0 | 0 | 0.00 | 0 | 0 | |
| 12.01 | Teaching Physician Salaries | 0 | 0 | 0.00 | 0 | 0 | |
| | Wage Related Costs | | | | | | |
| 13 | Wage related costs (Core) | 9,984,673 | | | 9,984,673 | | |
| 14 | Wage related costs (Other) | 0 | | | 0 | | |
| 15 | Excluded areas | 889,846 | | | 889,846 | | |
| 16 | Non-Physician Anestheist Part A | 0 | | | 0 | | |
| 17 | Non-Physician Anestheist Part B | 0 | | | 0 | | |
| 18 | Physician Part A (Administration) | 17,317 | | | 17,317 | | |
| 18.01 | Physician Part A (Teaching & Supervision of Interns) | 0 | | | 0 | | |
| 19 | Physician Part B | 22,594 | | | 22,594 | | |
| 19.01 | WRC - RHC/FQHC | 0 | | | 0 | | |
| 20 | Interns & Residents (approved) | 0 | | | | | |
| 21 | Overhead Costs - Direct Salaries | | | | | | |
| 22 | Employee Benefits | | | | | | |

PUF Data File Used
Top 10 CBSSs (Ranked by Salaries)

| Rank | CBSA Name | CBSA# | Providers | Salaries | Hours | AHW |
|---|---|---|---|---|---|---|
| 1 | New York | 35644 | 92 | 11,073,467,181 | 315,628,720 | 35.08 |
| 2 | Chicago | 16974 | 73 | 5,795,461,825 | 202,326,282 | 28.64 |
| 3 | LA | 31084 | 96 | 5,347,093,384 | 172,915,125 | 30.92 |
| 4 | Philedelphia | 37964 | 44 | 3,049,501,820 | 106,487,868 | 28.64 |
| 5 | Houston | 26420 | 45 | 2,925,192,618 | 111,324,656 | 26.28 |
| 6 | Boston | 14484 | 20 | 2,371,015,031 | 77,044,127 | 30.77 |
| 7 | Washington | 47894 | 30 | 2,178,759,915 | 74,988,333 | 29.05 |
| 8 | Atlanta | 12060 | 38 | 2,163,330,539 | 82,316,245 | 26.28 |
| 9 | Suffolk County | 44844 | 25 | 2,158,990,402 | 63,361,303 | 34.06 |
| 10 | Baltimore | 12580 | 22 | 2,052,423,265 | 78,595,698 | 26.11 |
|  | Subtotal |  | 485 | 39,115,181,980 | 1,285,018,357 | 30.44 |
|  | All Providers |  | 3,522 | 173,744,951,478 | 6,595,494,435 | 26.35 |

| Provider # | Hosp Name | FFY 10 CBSA Percentage | 2006 | | | 2007 | | |
|---|---|---|---|---|---|---|---|---|
| | | | Initial AHW | Final AHW | % change | Initial AHW | Find AHW | % change | Initial AHW |
| 140007 | PROVENA ST. JOSEPH MEDICAL CA... | 1.87% | $27.35 | $27.53 | 0.68% | $30.02 | $29.72 | -1.02% | $30.60 |
| 140008 | GOTTLIEB MEMORIAL HOSPITAL | 0.72% | $27.67 | $27.70 | 0.11% | $28.01 | $28.61 | 0.00% | $30.24 |
| 140010 | EVANSTON HOSPITAL | 4.94% | $34.11 | $33.51 | -1.73% | $30.84 | $30.75 | -0.30% | $38.71 |
| 140018 | MOUNT SINAI HOSPITAL | 1.22% | $27.83 | $27.08 | -0.54% | $25.05 | $26.19 | 4.58% | $29.60 |
| 140029 | COPLEY MEMORIAL HOSPITAL | 1.11% | $28.90 | $28.52 | -1.31% | $30.43 | $30.43 | 0.00% | $34. |
| 140030 | SHERMAN HOSPITAL | 1.25% | $29.43 | $29.40 | -0.12% | $30.42 | $30.45 | 0.09% | $32.26 |
| 140048 | TRINITY HOSPITAL | 0.82% | $27.66 | $27.50 | 0.58% | $29.29 | $28.76 | -1.82% | $30.22 |
| 140049 | WEST SURBURBAN HOSPITAL MEDICAL | 1.06% | $27.15 | $27.25 | 0.37% | $29.68 | $29.63 | -0.17% | $29. |
| 140051 | RUSH NORTH SHORE MEDICAL CENTER | 0.94% | $20.52 | $27.53 | 3.82% | $29.27 | $30.02 | 2.57% | $30. |
| 140054 | MACNEAL HOSPITAL | 1.30% | $34.02 | $30.61 | -10.01% | $33.03 | $31.89 | -3.45% | $33.60 |
| 140062 | PALOS COMMUNITY HOSPITAL | 2.02% | $34.11 | $33.80 | -0.91% | $33.21 | $33.98 | 2.32% | $34.97 |
| 140063 | OAK PARK HOSPITAL | 0.47% | $27.78 | $27.61 | -0.62% | $27.68 | $28.56 | 3.20% | $30. |
| 140065 | COLUMBIA - LA GRANGE | 0.83% | $33.39 | $28.34 | -15.13% | $29.57 | $29.49 | 0.36% | $30. |
| 140068 | ROSELAND COMMUNITY | 0.28% | $20.42 | $20.52 | 0.40% | $27.57 | $27.42 | 0.19% | $27.65 |
| 140075 | COLUMBIA MICHAEL REESE HOSPITAL | 0.62% | $27.37 | $26.93 | -1.62% | $26.05 | $26.07 | 0.07% | $19.62 |
| 140080 | ST. JAMES HOSPITAL & HEALTH CENTE | 0.93% | $22.71 | $23.12 | 1.82% | $28.03 | $28.63 | 0.00% | $24.50 |
| 140082 | SAINT FRANCIS HOSPITAL | 0.58% | $26.54 | $25.24 | -4.87% | $29.26 | $28.74 | -1.80% | $31.6 |
| 140083 | JULIUS A. WEISS MEMORIAL HOSPITAL | 0.38% | $26.83 | $26.19 | -2.38% | $26.90 | $26.65 | -1.15% | $28.26 |
| 140088 | LORETTO HOSPITAL | 0.38% | $29.77 | $32.26 | 8.35% | $30.93 | $31.05 | 0.41% | $32.46 |
| 140094 | THE UNIVERSITY OF CHICAGO HOSPIT... | 0.63% | $25.04 | $27.69 | 10.58% | $27.71 | $27.68 | -0.12% | $28.50 |
| 140095 | SAINTS MARY AND ELIZABETH MEDICA... | 0.43% | $26.58 | $26.91 | 1.22% | $26.48 | $27.97 | 5.70% | $32.78 |
| 140101 | SAINT ANTHONY HOSPITAL | 0.64% | $27.71 | $27.63 | -0.26% | $28.48 | $28.32 | 0.49% | $27.76 |
| | | 0.48% | $22.13 | $22.60 | 2.15% | $23.39 | $23.16 | -0.91% | $23.7 |
| | | | $27.26 | $27.23 | -0.11% | $28.21 | $28.21 | 0.01% | $29.2 |
| | | 1.22% | $27.06 | $27.05 | 0.00% | $27.79 | | 1.30% | $28 |

FIG. 40

WAGE INDEX NAVIGATOR SYSTEM

CROSS-REFERENCE TO RELATED APPLICATIONS

This application claims the benefit of U.S. Provisional Application Ser. No. 61/350,283, filed on Jun. 1, 2010, entitled "Wage Index Navigator System" which is incorporated herein by reference.

BACKGROUND AND SUMMARY

Section 1886(d)(3)(E) of the Social Security Act (the Act) requires that, as part of the methodology for determining prospective payments to hospitals, the Secretary must adjust the standardized amounts "for area differences in hospital wage levels by a factor (established by the Secretary) reflecting the relative hospital wage level in the geographic area of the hospital compared to the national average hospital wage level." This adjustment factor is the wage index. Hospital geographic areas (labor market areas) are defined based on the definitions of Core-Based Statistical Areas (CBSAs) established by the Office of Management and Budget. The wage index also reflects the geographic reclassification of hospitals to another labor market area in accordance with sections 1886(d)(8)(B) and 1886(d)(10) of the Act.

The Act further requires that the wage index be updated annually based on a survey of wages and wage-related costs of short-term, acute care hospitals. Data included in the wage index derives from the Medicare Cost Report, the Hospital Wage Index Occupational Mix Survey, hospitals' payroll records, contracts, and other wage-related documentation. In computing the wage index, an average hourly wage (AHW) is derived for each labor market area. The AHW for a geographic area is computed as total wage costs divided by total hours for all hospitals in the geographic area, and a national AHW is computed as the total wage costs divided by total hours for all hospitals in the nation. A labor market area's wage index value is the ratio of the area's average hourly wage to the national average hourly wage. The wage index adjustment factor is applied only to the labor portion of the standardized amounts.

The wage index review process is run annually by the Centers for Medicare and Medicaid Services (CMS) during the federal fiscal year. The Wage Index Navigator (WIN) system includes functionality to help hospitals and hospital/health systems in reporting and complying with this process. The typical wage index review process includes the following:

1. October—Release of the preliminary fiscal year wage index public use file (PUF).
2. December—Deadline for fiscal intermediaries (FIs) to have received the hospital's request for revisions to their Worksheet S-3 wage data and occupational mix data as included in the October PUF and provide documentation to support the hospital's request.
3. February—Deadline for FIs to complete desk reviews for hospital wage index data and transmit revised Worksheet S-3 data and occupational mix data to CMS' Division of Acute Care (DAC).
4. February—Deadline for FIs to notify State hospital associations regarding hospitals that fail to respond to issues raised during the desk review.
5. February—Release of revised fiscal year wage index and occupational mix files as PUFs on the CMS web site.
6. March—Deadline for hospitals to submit requests (including supporting documentation) for corrections to errors in the February PUFs due to CMS or FI mishandling of wage index data or revisions of desk review adjustments to their wage index data.
7. April/may—Proposed rule is published, which includes proposed wage index values.
8. April—Deadline for FIs to transmit final revised wage index data for inclusion in the final wage index.
9. April—Deadline for hospitals to appeal FI determinations and request CMS intervention in cases where the hospital disagrees with the FI's determination.
10. Late April—Wage index compiled and sent by CMS to FIs for verification.
11. May—Release of final wage index and occupational mix data PUFs on the CMS web site.
12. June—Deadline for hospitals to submit corrections to both CMS and their FI to correct errors due to CMS or FI mishandling of the final wage index and occupational mix data.
13. August—Approximate date for publication of the final rule; wage index rule includes final wage index corrections.
14. October—Effective date of wage index.

The Wage Index Navigator (WIN) system can be used by hospitals and hospital systems to input, compile and report wage index and occupational mix information. The majority of the processing and calculation of the WIN system are focused on the October PUF and the December filing of the hospital's request for revisions to their Worksheet S-3 wage data and occupational mix data as included in the October PUF, and the documentation to support the hospital's request. The majority of the processing after the December filing of the hospital's request is directed towards reporting and comparison of later publications and submissions until the next filing. An embodiment of the WIN system has been implemented as a web-based system. The WIN system can include functionality to:

Guide an end user through a set of questions, queries and tasks that will provide rigor and consistency to the compilation and reporting process;
Provide checks and balances that steer the end user towards submitting correct and complete data;
Provide a dashboard utility that manages the process and tactically assists medical facilities in completing the process;
Provides flexibility in allowing an end user the option of either importing or "keying-in" certain data elements;
Import publicly available and other hospital or relevant data;
Manage data by allowing supporting documentation to be uploaded for submission purposes and stored for future reference;
Generate reports to assist hospitals and hospital systems with compiling, filing and decision-making and with communicating with other hospitals; and
Maintain compliance with current CMS rules and regulations.

Terms relevant to the description of the WIN system are defined throughout this document. Some introductory definitions are provided here for an easier understanding of the description, and these definitions are augmented by more detailed definitions provided throughout this disclosure. The "Average Hourly Wage" (AHW) represents an average hourly wage dollar amount. The "AHW Index Factor" represents the ratio of the AHW for a CBSA to the AHW for the nation. A "Core Based Statistical Area" (CBSA) represents a geographic area in which a particular hospital's wage index is grouped. A "Fiscal Intermediary" (FI) is a reviewer appointed by the CMS that performs a desk review of a hospital's wage index submission and reports to the CMS. The "Federal Register" is a publication of the federal government that includes data from the CMS used as an input to the WIN system. The "Public Use Files" (PUFs) are data files published periodically by the CMS and are described in more detail below. The PUFs are currently published in October, February, May and August which may be referred to herein as the October PUF, February PUF, May PUF and August PUF, respectively. An Electronic Cost Report (ECR) is a report generated annually for or by a hospital that contains information useful for the WIN system. The "S-3" refers to Worksheet S-3, Parts II & III which are included in the PUFs published by CMS. The "Initial S-3" refers to the initial version of the S-3, usually generated from the ECR or the October PUF. The "Proposed S-3" is generated by the WIN system as part of the proposed adjustment listing. The "Revised S-3" refers to the S-3 that comes back from the FI desk review.

A healthcare wage index reporting method is disclosed that includes providing questions and tasks through an electronic user interface to collect information for filling out a wage index and occupational mix report; electronically receiving responses to the questions and tasks; processing the responses to complete the wage index and occupational mix report; checking the responses to detect inconsistencies or errors; generating notices of detected inconsistencies or errors in the wage index and occupational mix report; tracking progress in completing the wage index and occupational mix report; and generating a completed wage index and occupational mix report for submission to a recipient. The recipient can be a fiscal intermediary that communicates with the Centers for Medicare and Medicaid Services (CMS). The method can also include displaying a dashboard showing progress of completing the wage index and occupational mix report, and current results for the wage index and occupational mix report. The method can also include validating the completed wage index and occupational mix report before submission; and protecting the validated wage index and occupational mix report from further modification.

The healthcare wage index reporting method can also include separating the wage index and occupational mix report into a plurality of sections; delegating each of the plurality of sections to a coordinator for completion; and for each completed section of the plurality of sections, compiling the information from the completed section to complete the wage index and occupational mix report. The method can also include tracking the progress toward completion of each delegated section, displaying a progress monitor showing the progress toward completion of each delegated section; and generating a notification message when each delegated section is completed.

The healthcare wage index reporting method can also include importing an electronic data file, storing the data in the imported electronic data file in memory; and processing the data from the imported electronic data file to complete the wage index and occupational mix report. The electronic data file can be a wage index and occupational mix public use file (PUF). The electronic data file can be used to pre-populate responses. Notifications can be generated of differences between information in the wage index and occupational mix report and information received from the electronic data file. In some embodiments, the notifications are only generated when the difference between information in the wage index and occupational mix report and information received from the electronic data file exceeds a threshold for that response. The threshold for generating a notification can be different for different information in the wage index and occupational mix report. A discrepancy report can be generated that shows differences between information in the wage index and occupational mix report and information received from the electronic data file.

Generating notices of detected inconsistencies or errors can include automatically notifying a user of a detected error; and not permitting progress in the wage index reporting process until the detected error is corrected. The healthcare wage index reporting method can also include providing a user-selectable link to more detailed instructions for responding to a particular question or task; and displaying more detailed instructions for responding to the particular question or task when the user-selectable link is selected. The more detailed instructions can include a worksheet or a series of questions for deriving the desired response to the particular question or task.

Receiving responses can include receiving supplemental attachment files supporting a response. The healthcare wage index reporting method can also include preparing workpapers supporting a particular response to a question or task; and attaching the workpaper to an appropriate portion of the wage index and occupational mix report. Preparing workpapers supporting a particular response to a question or task can include providing a workpaper template for collecting the supporting information for the particular response. The healthcare wage index reporting method can include electronically receiving a comment associated with one of the responses to the questions and tasks, the comment providing a user explanation of the response; and associating the comment with the one of the responses to the questions and tasks. The method can also include uploading audited financial statements; and reconciling the wage index and occupational mix report against the uploaded audited financial statements. The method can include selecting supporting documentation to be submitted with the completed wage index and occupational mix report.

The healthcare wage index reporting method can include generating prompts based on responses to the questions and tasks; and displaying the prompts as part of future questions and tasks provided to collect information for filling out a wage index and occupational mix report. The method can also include determining future questions and tasks to be provided based upon responses to previous questions and tasks. The method can also include generating reminders of time left for submission of the wage index and occupational mix report.

The healthcare wage index reporting method can include generating user-requested reports, for example an analysis report for review of current status of the wage index and occupational mix report; or an impact report showing the impact of proposed changes to the wage index and occupational mix report; or a proposed adjustment listing showing the differences between the current wage index and occupational mix report and a revision to the wage index and occupational mix report; or a county reclassification summary report showing the financial impact of county reclassification within a core based statistical area (CBSA); or an estimated wage index and occupational mix report based upon currently received information. The impact report can be generated for a selected core based statistical area (CBSA).

The healthcare wage index reporting method can include maintaining an audit log recording all responses and the source of each response. The method can also include receiving user messages for posting on a system bulletin board; receiving bulletin board responses responding to posted messages on the system bulletin board; associating each bulletin board response with the appropriate posted message; and deleting each posted message and any associated responses after a designated time period.

A healthcare wage index reporting system is disclosed that includes an electronic user interface, a processor, a validation module, an electronic dashboard and a finalization module. The electronic user interface provides questions and tasks to collect information for filling out a wage index and occupational mix report, and receives responses to the questions and tasks. The processor processes the responses to complete the wage index and occupational mix report. The validation module checks the responses to detect inconsistencies or errors in the wage index and occupational mix report, and generates notices of detected inconsistencies or errors in the wage index and occupational mix report. The electronic dashboard tracks progress in completing the wage index and occupational mix report. The finalization module generates a completed wage index and occupational mix report for submission to a recipient. The recipient can be a fiscal intermediary that communicates with the Centers for Medicare and Medicaid Services (CMS).

The electronic user interface can import and store electronic data files, and the processor can process the data from the imported electronic data files to complete the wage index and occupational mix report. The electronic data file can be a wage index and occupational mix public use file (PUF). The processor can pre-populate responses based on the electronic data file. The validation module can generate notifications of differences between information in the wage index and occupational mix report and information received from the electronic data file. In some embodiments, the notifications are only generated when the difference between information in the wage index and occupational mix report and information received from the electronic data file exceeds a threshold for that response. The validation module can generate a discrepancy report showing differences between information in the wage index and occupational mix report and information received from the electronic data file. The validation module can automatically notify a user of a detected error; and prevent further progress in the wage index reporting process until the detected error is corrected.

The healthcare wage index reporting system can include a help module for providing more detailed instructions for responding to the particular question or task when a user-selectable link is selected. The help module can provide a worksheet or a series of questions for deriving the desired response to the particular question or task.

The electronic user interface can accept supplemental attachment files supporting a response. The electronic user interface can display templates for collecting data and preparing workpapers to support a particular response to a question or task. The electronic user interface can accept audited financial statements; and the validation module can reconcile the wage index and occupational mix report against the uploaded audited financial statements. The electronic user interface can accept comments associated with one of the responses to the questions and tasks, where the comment provides a user explanation of the response. The healthcare wage index reporting system can include a reviewer module for a reviewer to respond to the user explanation in the comment field. The reviewer module can include a deletion function for deleting the comment field.

The finalization module can validate the completed wage index and occupational mix report before submission; protect the validated wage index and occupational mix report from further modification, and electronically submit the completed wage index and occupational mix report to the recipient. The finalization module can select supporting documentation to be submitted with the completed wage index and occupational mix report.

The processor can generate prompts based on responses to the questions and tasks; and the electronic user interface can display the prompts as part of future questions and tasks provided to collect information for filling out a wage index and occupational mix report. The processor can determine future questions and tasks to be provided through the electronic user interface based upon responses to previous questions and tasks. The processor can generate reminders of time left for submission of the wage index and occupational mix report.

The healthcare wage index reporting system can include a report module for generating user-requested reports, including an analysis report to review the current status of the wage index and occupational mix report; an impact report showing the impact of proposed changes to the wage index and occupational mix report; a proposed adjustment listing showing the differences between the current wage index and occupational mix report and a revision to the wage index and occupational mix report; a county reclassification summary report showing the financial impact of county reclassification within a core based statistical area (CBSA); or an estimated wage index and occupational mix report based upon currently received information.

The healthcare wage index reporting system can include an audit module for maintaining an audit log recording all responses and the source of each response. The healthcare wage index reporting system can also include a bulletin board module for receiving bulletin board posts, receiving bulletin board responses associated with bulletin board posts, and deleting each bulletin board post and any associated responses after a designated time period.

BRIEF DESCRIPTION OF THE DRAWINGS

FIG. 25 shows an exemplary format for an impact sheet summary;

FIG. 26 shows an exemplary impact sheet;

FIG. 27 shows an exemplary portion of a proposed adjustment listing;

FIG. 28 shows an exemplary S-3 display;

FIG. 29 shows an exemplary county reclassification summary report;

FIG. 31 shows a portion of an exemplary estimated impact report for a CBSA;

FIG. 32 shows an exemplary estimated impact report for a hospital;

FIG. 33 shows an exemplary "what-if" impact scenario report;

FIG. 34 shows an exemplary CBSA overview report;

FIG. 35 shows an exemplary summary PUF comparison report for a CBSA;

FIG. 36 shows an exemplary PUF comparison report for a CBSA;

FIG. 37 shows an exemplary PUF comparison report for a hospital;

FIG. 40 shows an exemplary trending report;

DESCRIPTION OF EXEMPLARY EMBODIMENTS

The exemplary embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

Figure 1:
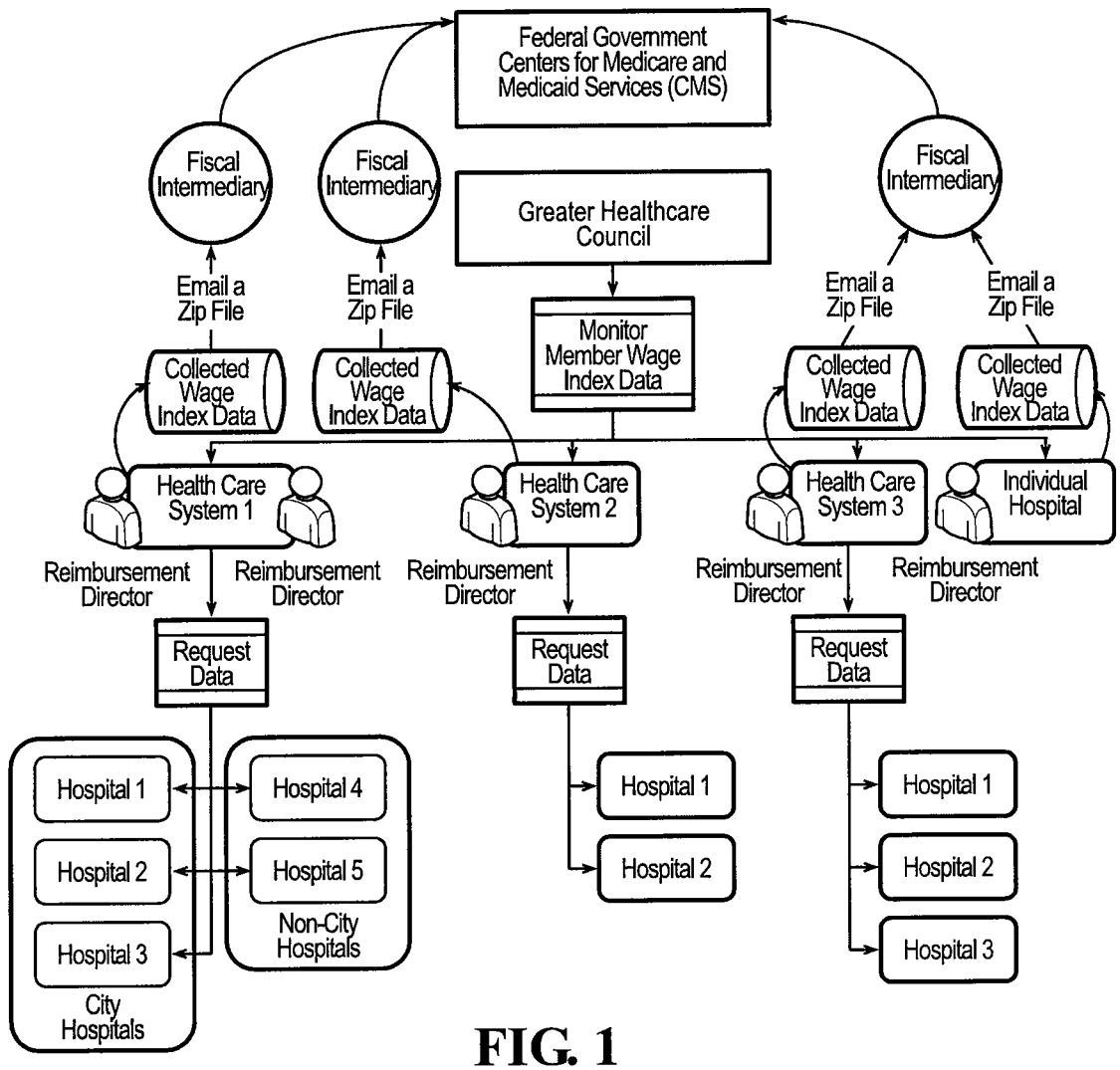
FIG. 1 illustrates a hospital system in which the wage index navigator system can be utilized along with some of the interconnections in the wage index review process.

The Wage Index Navigator (WIN) system can be used by or for individual hospitals and by or for hospital systems. FIG. 1 shows an exemplary hospital system in which the WIN system can be utilized in the wage index review process. The hospital system shown in FIG. 1 includes a Greater Healthcare Council that includes members of Health Care Systems 1-3 and an Individual Hospital. Health Care System 1 includes five hospitals of which three are in the city and two are not in the city. Each of the five hospitals of Health Care System 1 provides information for the wage index review process to the wage index review process coordinator(s) for Health Care System 1, which may be one or more reimbursement directors. Health Care System 2 includes two hospitals that each provides information for the wage index review process to the wage index review process coordinator for Health Care System 2. Health Care System 3 includes three hospitals that each provides information for the wage index review process to the wage index review process coordinator for Health Care System 3. The Individual Hospital collects information for their hospital for the wage index review process. The WIN system assists the hospitals and hospital systems in the wage index data collection, compilation and reporting process. The Greater Healthcare Council can also use the WIN system to perform wage index reporting for their members and/or to monitor the wage index data collection, compilation and reporting process.

In the exemplary diagram shown in FIG. 1 there are three fiscal intermediaries (FIs) for the member health care systems and hospitals of the Greater Healthcare Council. A first FI is assigned to Health Care System 1, a second FI is assigned to Health Care System 2, and a third FI is assigned to both Health Care System 3 and the Individual Hospital. The WIN system can be used by each of Health Care Systems 1-3 and the Individual Hospital to collect and report wage index data to the appropriate FI. The reporting can be done electronically using a compressed file. The FIs review the reported data and communicate with the appropriate healthcare systems and hospitals, as well as with the Centers for Medicare and Medicaid Services (CMS).

Some exemplary ways in which the WIN system can be used in the exemplary environment of FIG. 1 include the following. The Greater Healthcare Council can perform on-site review at the member health care systems and hospitals using the Wage Index Navigator system. The data can be entered into the WIN system by Greater Healthcare Council staff and reported to the FI in both electronic and hardcopy formats. The Greater Healthcare Council can perform maintenance reviews where the council receives a copy of a hospital's S-3 and other data as part of a high-level review, and the council staff can enter the revised S-3 and adjustments requested by the hospital into WIN system in order to accumulate data for reporting purposes. A health care system or hospital can uses the WIN system to facilitate the wage index process themselves, and may receive training and/or support available from the council. An independent third-party can use the WIN system to review collected data and reports. The council can have the ability to import or "key-in" the final S-3 results into the WIN system for any member health system or hospital.

Figure 2:
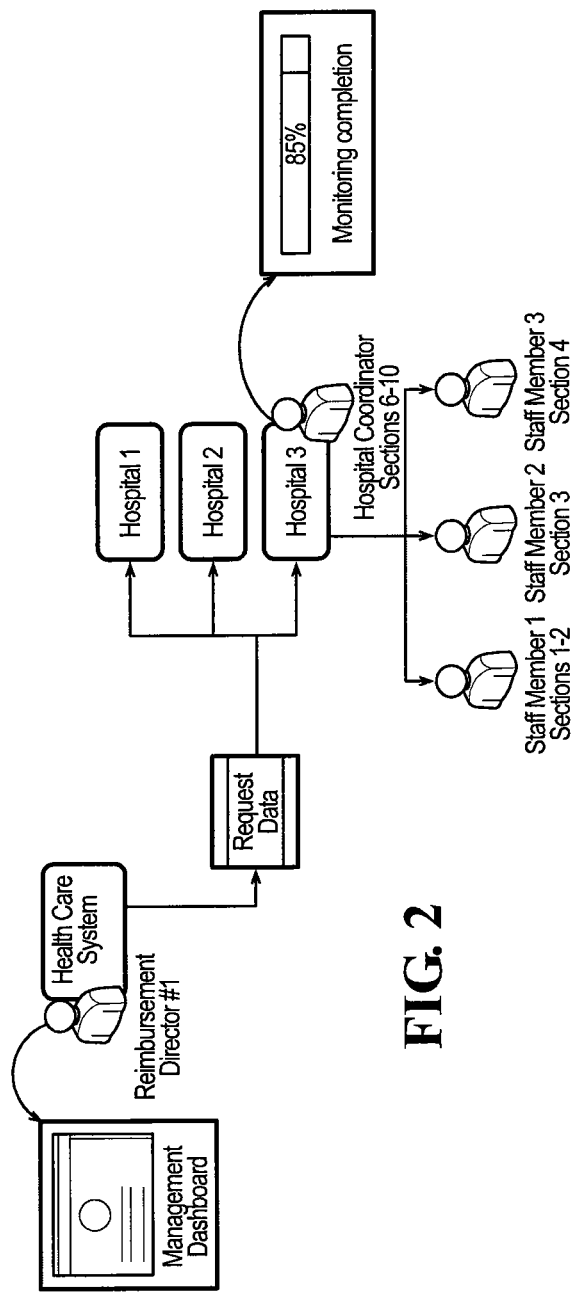
FIG. 2 illustrates an exemplary perspective for a health system with more than one hospital.
Figure 3:
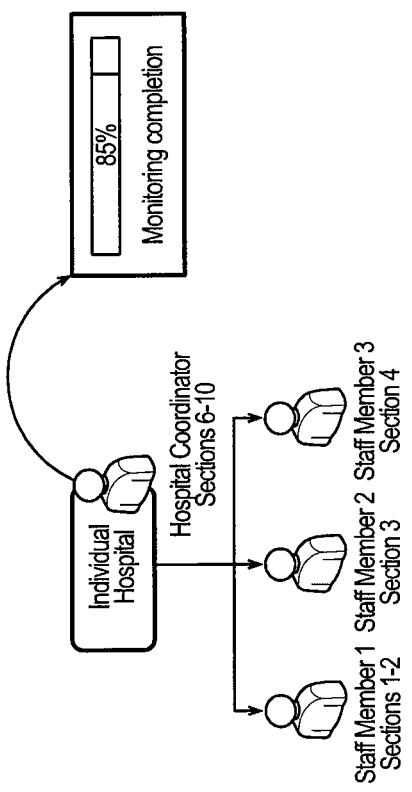
FIG. 3 illustrates an exemplary perspective for an individual hospital.

FIG. 2 provides an exemplary perspective for a health system with more than one hospital, and FIG. 3 provides an exemplary perspective for an individual hospital. The health care system of FIG. 2 includes N hospitals. The health care system has a reimbursement director that can typically delegate responsibility for data collection and compilation for the wage index review process to various hospital coordinators and other staff members. The reimbursement director(s) are usually responsible for initiating and overseeing the process. The hospital coordinator completes portions or all of the input required, and may delegate portions or all of the questions as desired. The hospital coordinator can review and edit the data, and typically finalizes the inputs for their hospital. The reimbursement director can be automatically notified by the WIN system when the input is finalized by the hospital coordinator. The reimbursement director can review and edit or return the input of the hospital coordinator for further adjustments.

The WIN system can support one or more reimbursement directors for a health system. Each of the reimbursement directors can be assigned ownership of different hospitals for which they will be responsible for controlling the wage index review process. The hospitals assigned to a reimbursement director may or may not all be within the same core based statistical area (CBSA). The WIN system can account for the CBSA data groupings. A maintenance process can support the ability to control the mapping of reimbursement director to hospital for a given health system. A management dashboard and/or progress monitor can be made available to the reimbursement director or other entities to track the progress of the wage index review process.

The hospital coordinator can complete portions or all of the input required. The hospital coordinator can delegate specific blocks of questions or the entire set of questions to other individuals. The hospital coordinator reviews and makes final edits to the collected data and typically finalizes the information for their hospital. The hospital coordinator and assigned staff can use a web-based interface to input/compile information for wage index review process. The WIN system can be configured to consider the hospital coordinator or other entity to be the master/owner of the wage index data and not allow other persons or entities to finalize the wage index review. A management dashboard and/or progress monitor can be made available to the hospital coordinator or other entities to track the overall percentage completion of the wage index review process for the hospital.

The high level steps involved in the wage index review process can include central import of the public use file (PUF) data into the WIN system, completion of the wage index review and submission to the FI through WIN system, exception monitoring and additional reporting functionality.

The WIN system can provide various forms of user guidance/help to assist hospitals and hospital systems in completing the wage index review. The WIN system can provide in process "alerts", which are warnings presented to the user when data does not validate properly or is otherwise incorrect. Selected alerts can be configured to not allow a user to continue in the wage index process until correcting the issue causing the alert. There WIN system can provide summary information, and alternatively can provide a user-selectable link to more detailed information. The WIN system can be configured to provide "prompts" to the user at selected steps where the prompts are informational and/or provide work step directions and other items of note to the user. The prompts have configurable content and can include links to more detailed information. The user guidance can be maintained and adjusted by a system administrator or other authorized persons. The WIN system can be configured to provide spreadsheets and other example templates for download to assist users with understanding certain work steps, or providing examples on certain work steps.

The WIN system enables the user to upload one or more supporting documents, spreadsheets or other attachments. The user can select an attachment. The WIN system will provide a visual indicator for the entries or work steps that include attachment(s). The WIN system will allow the user to delete uploaded attachments, upload additional attachments, or download copies of attachments.

The WIN system can pre-populate input values from a PUF or ECR file or other available sources where appropriate. Adjustments made to the pre-populated values can be tracked as proposed adjustments. Textboxes can be made available for the user to explain reasoning for their entries or adjustments.

If the user chooses to start the wage index review process prior to the October PUF, they can key in an S-3 or upload an ECR off which the process will be based. If the user chooses to start the process in advance of the October PUF and enters their S-3, the WIN system can check for any discrepancies and notify the appropriate party of any differences when the PUF data is imported. The user can continue to make adjustments until the deadline for submission has past. The WIN system can provide reminders of when the deadline is approaching. The WIN system automatically saves progress as the user navigates through the data input process. The wage index process is not complete until the user has passed all of the validation checks and marked the review as finalized. Once finalized, the user can no longer make edits to the wage index information.

The WIN system can provide the ability for users authorized to complete a wage index review or contribute to portions of the review to create notes about the review in a general notes area. All or specified users contributing to a review can read the notes associated with a review. The notes can be modified or deleted, and can be listed in a selected order, such as from newest to oldest.

The WIN system can provide quality controls that include checks and balances to ensure correct and complete data is provided in the wage index review process. The quality controls can be embedded directly within the review process. The quality controls can contain checks enforced and brought to the user's attention throughout the process as the alerts occur. The quality controls can contain additional final checks at the end of the wage index review process to check the overall validity once everything is believed to be complete. The specific quality controls can be defined as a part of the data gathering process. The system can have threshold checks embedded in the process. An exemplary threshold check is a user alert when there is a five percent or greater difference between a current value and a prior year value for a data entry. The system can also include process wizards for selected work steps. A process wizard can include an alternate checklist that the user can launch on the associated steps in order to guide them through a particular work step with more detailed prompts.

There a various data sources for the wage index review process, and these can be used to populate data fields by the WIN system. The Public Use Files (PUFs) are released from time to time by the Centers for Medicare and Medicaid Services (CMS). Different PUFs are released for wage index and occupational mix purposes. The wage index PUFs contain the collection of hospital wage data reported to CMS on Worksheet S-3, Parts II and III of the Medicare cost report. The occupational mix PUFs contain the collection of occupational mix review data reported by hospitals to CMS. CMS collects occupational mix review data once every three years.

There are typically four versions of the wage index and occupational mix PUF that will be centrally uploaded to the WIN system. There is a PUF released in October, which is preliminary/initial and used as the starting point of the wage index review process. The second PUF is released in February, which is a revised version of the October PUF. The third PUF is released in May and corresponds with the publication of the proposed changes to the hospital inpatient prospective payment systems (IPPS) in the Federal Register. The final PUF is released in August and corresponds with the release of the publication of the final changes to the hospital IPPS in the Federal Register.

The WIN system includes an administrative interface to allow for a PUF file to be imported to the system for a specified version (October, February, May, and final) based on the federal fiscal year. The October PUF is the preliminary file; the February PUF reflects the data after it has gone through the fiscal intermediary (FI) desk review and the FI has accepted or rejected the proposed changes; and the May PUF reflects corrections to the February PUF. The WIN system stores each PUF file for a different time period separately so that data from different periods is available for comparison and reporting.

The electronic cost report (ECR) is generated by the hospital. The ECR for the cost report under review should be provided by each hospital in a standardized format. The ECR data is parsed and used to pre-populate a variety of input fields as well as to help determine which data inputs apply. The WIN system enables the user to electronically upload the hospital ECR data file to pre-populate certain segments of the wage index review. The WIN system supports file formats for the ECR file that are created by hospitals using widely accepted software tools such as Health Financial Systems. The WIN system can also be configured to support other formats. The data file is preferably in the data format supported by CMS (e.g., 2552-96 as currently defined by CMS). When the ECR file is uploaded, the user can specify the hospital fiscal year with which the ECR file is associated. The WIN system can be configured to overwrite the ECR data for the selected hospital fiscal year each time it is uploaded. The WIN system enables the user to input any missing data needed from the ECR should they not have an ECR with the data available.

The hospital may also complete their S-3 outside of the WIN system. It is desirable to include the S-3 information in the WIN system for a complete data set for comparison and other purposes. The user inputs the average hourly wage according to what is on their S-3, Part III, line 6, and column 5. The user can input the remaining or any revised S-3 values. Authorized hospitals can directly enter their own S-3 data, and authorized users can enter S-3 data on behalf of a hospital. The inputted S-3 values are utilized to calculate the average hourly wage and to compare it to the previously given value from their S-3. If there is a discrepancy, the user will be prompted to identify and correct the issues until the values match. This serves as a validation check as the S-3 is entered. Pre-desk review and post desk review versions of the S-3 can be entered by the user. A previously entered S-3 can be re-entered or replaced if there is a revised version of the S-3. A discrepancy report can be executed to compare the revised S-3 against both the February PUF and May PUF for any hospitals that did not complete the wage index review through the WIN system. An electronic copy of documentation received from the FI's desk review can also be attached to the S-3. The WIN system can populate the S-3 values in a number of ways including data from the PUFs, imported ECR, or direct user entry. The pre-populated values can be modified or replaced with adjusted values.

The CMS publishes several data files in addition to the PUF files that can be utilized by the WIN system for calculations, reporting, and trending. The WIN system can upload the "Final Rule Standardizing" file which contains data such as number of cases, case mix, and other data useful for reporting and trending. The WIN system can upload the "Final Review and Correction Notice" file which contains the hospital provider name, CBSA mapping, and reclassifications. The Final Review and Correction Notice file provides the capability to setup all of the hospitals to CBSA mappings. The WIN system can upload the "Final Corrected Rates" data file which contains data for Table 1A through 1E, plus the national average hourly wage as published in the Federal Register. The Final Corrected Rates data file can be utilized in calculating the reimbursement impact. The WIN system can upload the "Final Corrected Tables" data file which contains data for Tables 2, 3A, 3B, 4A, 4B, 4C, 4F, 4J, 9A, 9B, and 9C. This Final Corrected Tables data can be utilized as input for trending reports.

The Medicare Provider Analysis and Review (MEDPAR) file is produced by CMS and contains records for 100% of Medicare beneficiaries who use hospital inpatient services. The records are stripped of most data elements that will permit identification of beneficiaries. The six positions Medicare billing number identifies the hospital. The MEDPAR file has certain data elements such as number of Medicare admissions that can be used by the WIN system for reporting purposes. The MEDPAR file is available from CMS for purchase. The Final Rule Standardizing file described above contains data that is also in the MEDPAR file. The Final Rule Standardizing file can be utilized as the primary file and the MEDPAR file can be used as a backup.

Figure 4:
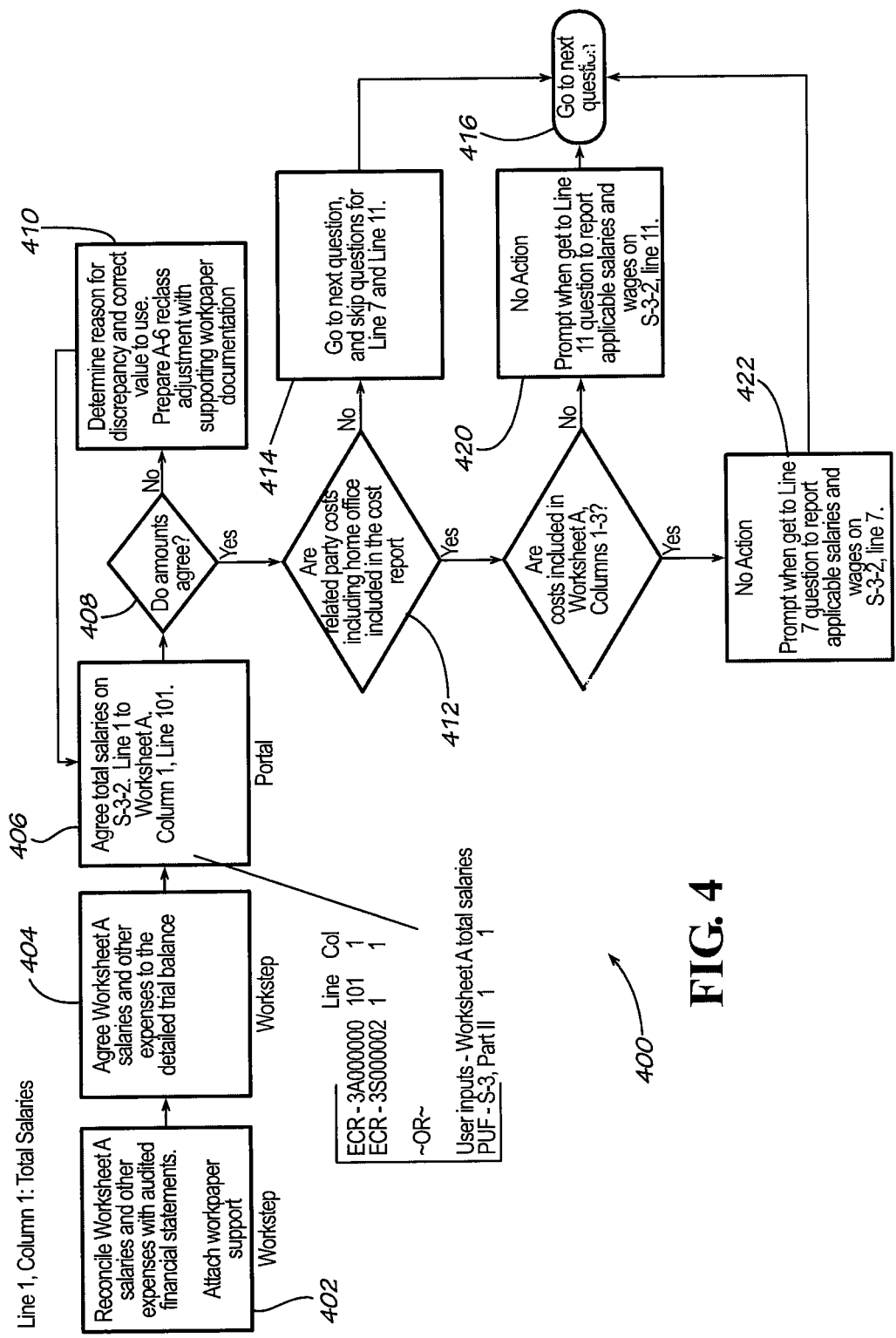
FIG. 4 shows an exemplary process for computing the total salaries entry on line 1, column 1.

FIG. 4 shows an exemplary data gathering and compilation process 400 for computing the total salaries entry on line 1, column 1. This process confirms that the reported salaries are correct and that the trial balance, worksheet A and financial statements agree to demonstrate that underlying financial detail supporting any proposed adjustments is valid. The data sources for this process include audited financial statements, audited trial balance, Worksheet A (which is part of the ECR data) and reconciliation workpaper from audited financial statement to Worksheet A. This process includes the wages and salaries paid to hospital employees increased by amounts paid for vacation, holiday, sick, paid time off (PTO), severance and bonus pay if not repeated in Line 1. Bonus pay includes award pay and vacation, holiday and sick pay conversion (pay in lieu of time off). Capital related salaries associated from Lines 1-4 of Worksheet A are excluded from the wage index. Salaries should exclude contract labor and salaries where no hours are reported. The WIN system can include an alert or prompt for the user to consider if multiple payrolls are included (e.g., executive payroll).

At block 402, Worksheet A salaries and other expenses are reconciled with audited financial statements. Calculations and attachments can be included to show support for the results. At block 404, the Worksheet A salaries and other expenses are reconciled to agree with the detail trial balance. At block 406, the total salaries on S-3, Part II, line 1 are compared with Worksheet A, col. 1, line 101. At block 408, the system checks that the amounts compared in block 406 agree. If the amounts agree control is transferred to block 412, otherwise control is transferred to block 410.

At block 410, a determination is made of the reason for the discrepancy and what the correct value should be. An A-6 adjustment is also prepared with supporting documentation. Control is transferred back to block 406 to check the corrected values.

At block 412, a determination is made whether related party costs, including home office costs, are included in the cost report. If related party costs are included control is transferred to block 418, otherwise control is transferred to block 414. At block 414, the system notes to skip questions for lines 7 and 11. From block 414 the system proceeds to block 416 which proceeds to the next question.

At block 418, a determination is made whether all costs are included in Worksheet A, columns 1-3. If all costs are included control is transferred to block 422, otherwise control is transferred to block 420. At block 420, the system notes to prompt the user at line 11 question to report applicable salaries and wages on S-3, Part II, line 11. From block 420 the system proceeds to block 416 which proceeds to the next question.

At block 422, the system notes to prompt the user at line 7 question to report applicable salaries and wages on S-3, Part II, line 7. From block 422 the system proceeds to block 416 which proceeds to the next question.

Figure 5:
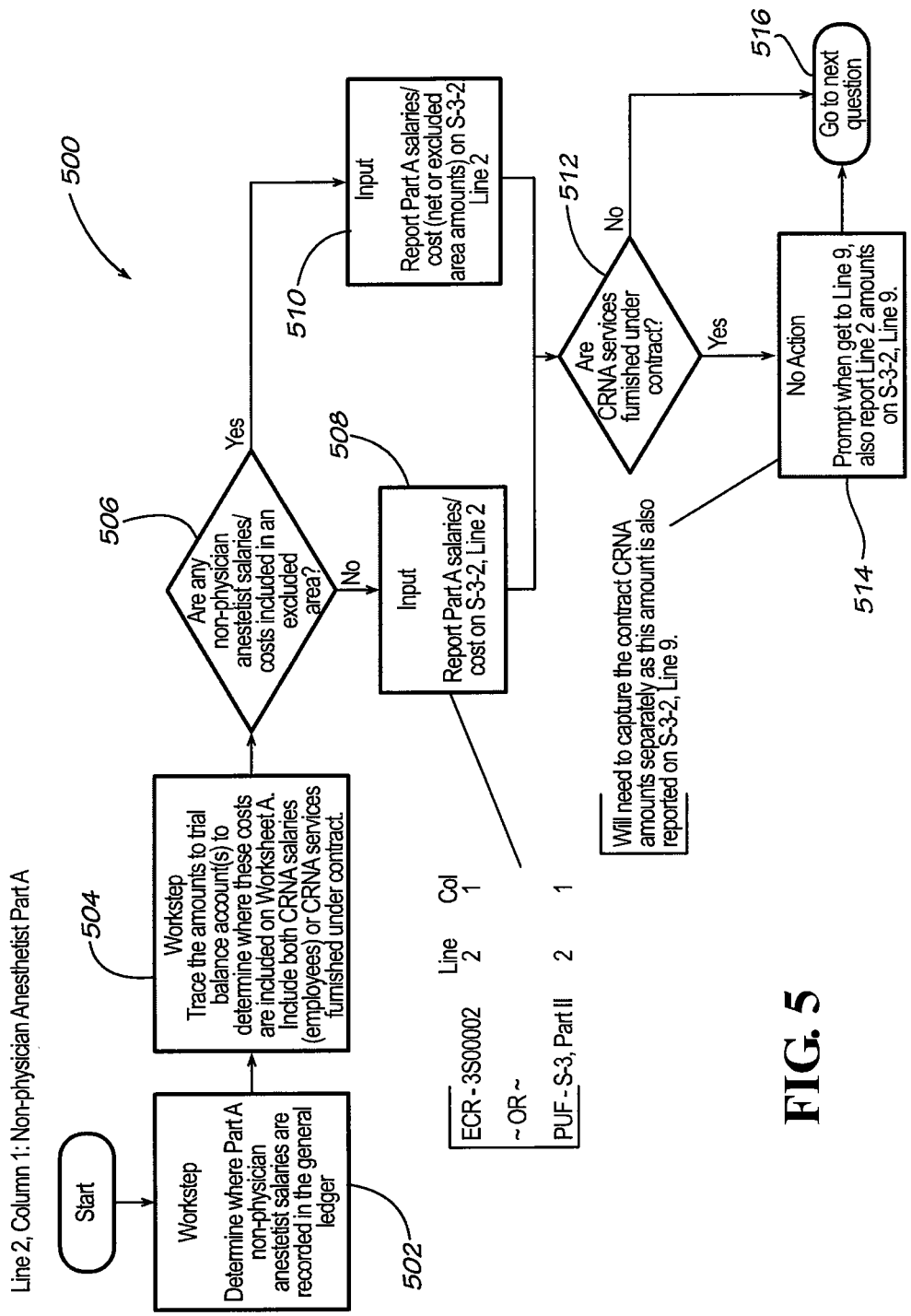
FIG. 5 shows an exemplary process for computing the non-physician anesthetist, Part A entry on line 2, column 1.

FIG. 5 shows an exemplary data gathering and compilation process 500 for computing the non-physician anesthetist, Part A entry on line 2, column 1. This process reports directly employed and/or contracted non-physician anesthetist, Part A dollars. The data sources for this process include audited trial balance. This series of questions is displayed for a rural hospital or when the hospital directly employs or contracts Part A non-physician anesthetists. Line 2 should include contract Part A non-physician anesthetist (CRNA) services to the extent that hours can be accurately determined. Prompts and alerts can be provided to alert the user to various rules regarding the proper entries, including the following. Equipment, supplies, travel expenses or other miscellaneous or overhead costs should not be included. Physician assistants, clinical nurse specialists, nurse practitioners and nurse midwives should not be included. Salaries applicable to excluded areas reported on S-3, Part II, lines 8 and 8.01 should also not be included. Contract non-physician anesthetist costs are also included on line 9. These amounts are not included in the average hourly wage (AHW) calculations.

At block 502, it is determined where Part A non-physician anesthetist salaries are recorded in the general ledger. Then at block 504, the amounts are traced to trial balance accounts to determine where these costs are included on Worksheet A. Both non-physician anesthetist employees and non-physician anesthetist services furnished under contract are included. At block 506, it is determined whether any non-physician anesthetist salaries or costs are included from an excluded area. If any are included control is transferred to block 510, otherwise control is transferred to block 508.

At block 508, Part A salaries and costs are reported on S-3, Part II, line 2; and control passes to block 512. At block 510, Part A salaries and costs, not including excluded area amounts, are reported on S-3, Part II, line 2; and control passes to block 512.

At block 512, it is determined whether non-physician anesthetist services are furnished under contract. If non-physician anesthetist services are not furnished under contract, then the system proceeds to block 516 and the next question. If non-physician anesthetist services are furnished under contract, then the system proceeds to block 514 and notes to prompt the user at line 9 to also report line 2 amounts on S-3, Part II, line 9. The contract CRNA amounts will be captured separately as the amount is also reported on S-3-2, line 9. From block 514 control proceeds to block 516 and the next question.

Figure 6:
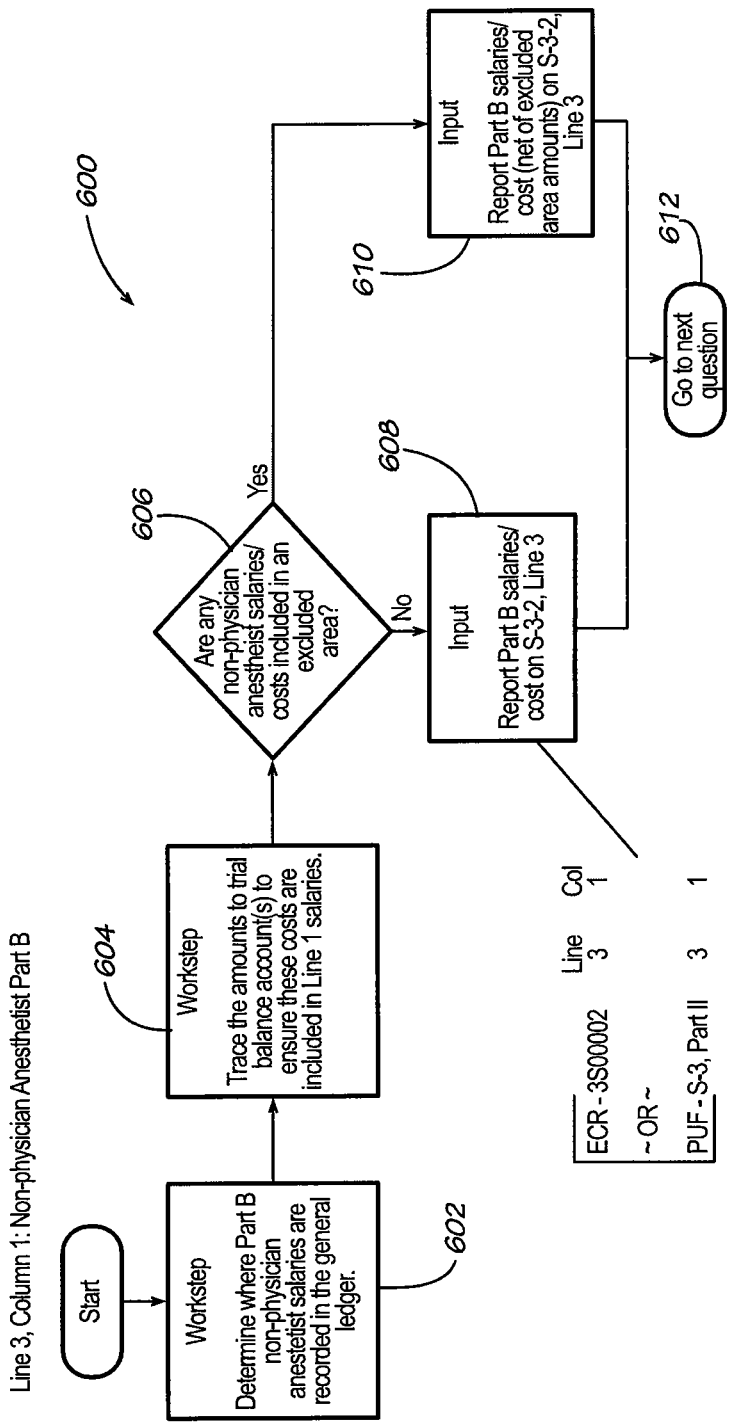
FIG. 6 shows an exemplary process for computing the non-physician anesthetist, Part B entry for line 3, column 1.

FIG. 6 shows an exemplary data gathering and compilation process 600 for computing the non-physician anesthetist, Part B entry for line 3, column 1. This process reports non-physician anesthetist, Part B salaries. The data sources for this process include audited trial balance. This series of questions is displayed for a rural hospital or when non-physician anesthetists are paid under Part B. Line 2 should include contract Part A non-physician anesthetist (CRNA) services to the extent that hours can be accurately determined. Prompts and alerts can be provided to alert the user to various rules regarding the proper entries, including the following. Equipment, supplies, travel expenses or other miscellaneous or overhead costs should not be included. Physician assistants, clinical nurse specialists, nurse practitioners and nurse midwives should not be included. Salaries applicable to excluded areas reported on S-3, Part II, lines 8 and 8.01 should also not be included. Contract non-physician anesthetist costs are also reported on line 9. These amounts are not included in the average hourly wage (AHW) calculations.

At block 602, it is determined where Part B non-physician anesthetist salaries are recorded in the general ledger. Then at block 604, the amounts are traced to trial balance accounts to ensure that these costs are included on Line 1 salaries. At block 606, it is determined whether any non-physician anesthetist salaries or costs are included from an excluded area. If any are included control is transferred to block 610, otherwise control is transferred to block 608.

At block 608, Part B salaries and costs are reported on S-3, Part II, line 3; and control passes to block 612. At block 610, Part B salaries and costs, not including excluded area amounts, are reported on S-3, Part II, line 3; and control passes to block 612. At block 612, the system proceeds to the next question.

Figure 7A:
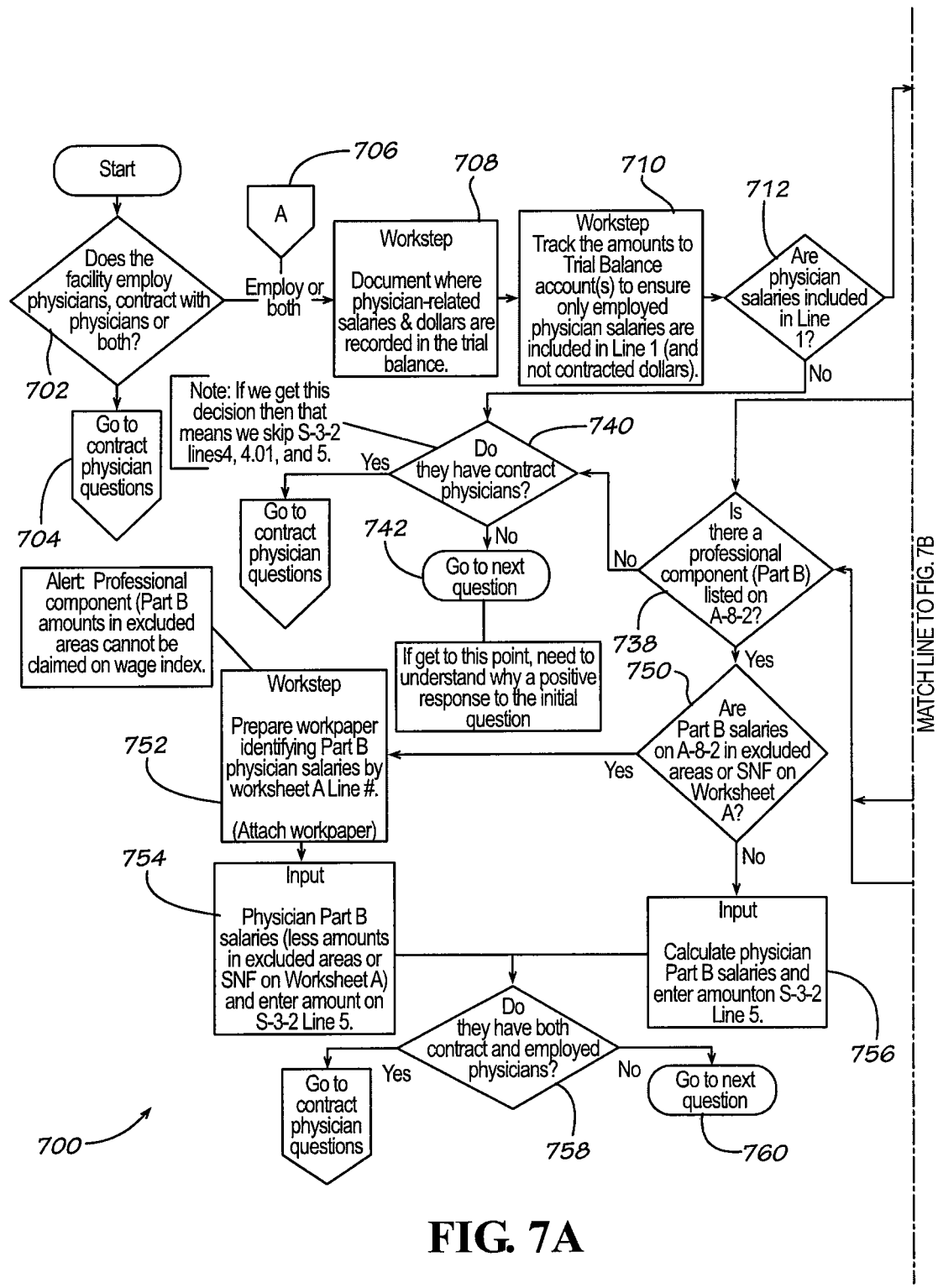
FIG. 7 shows an exemplary process for computing the employed physician entry for lines 4, 4.01, 5, 10 and 10.01.
Figure 7B:
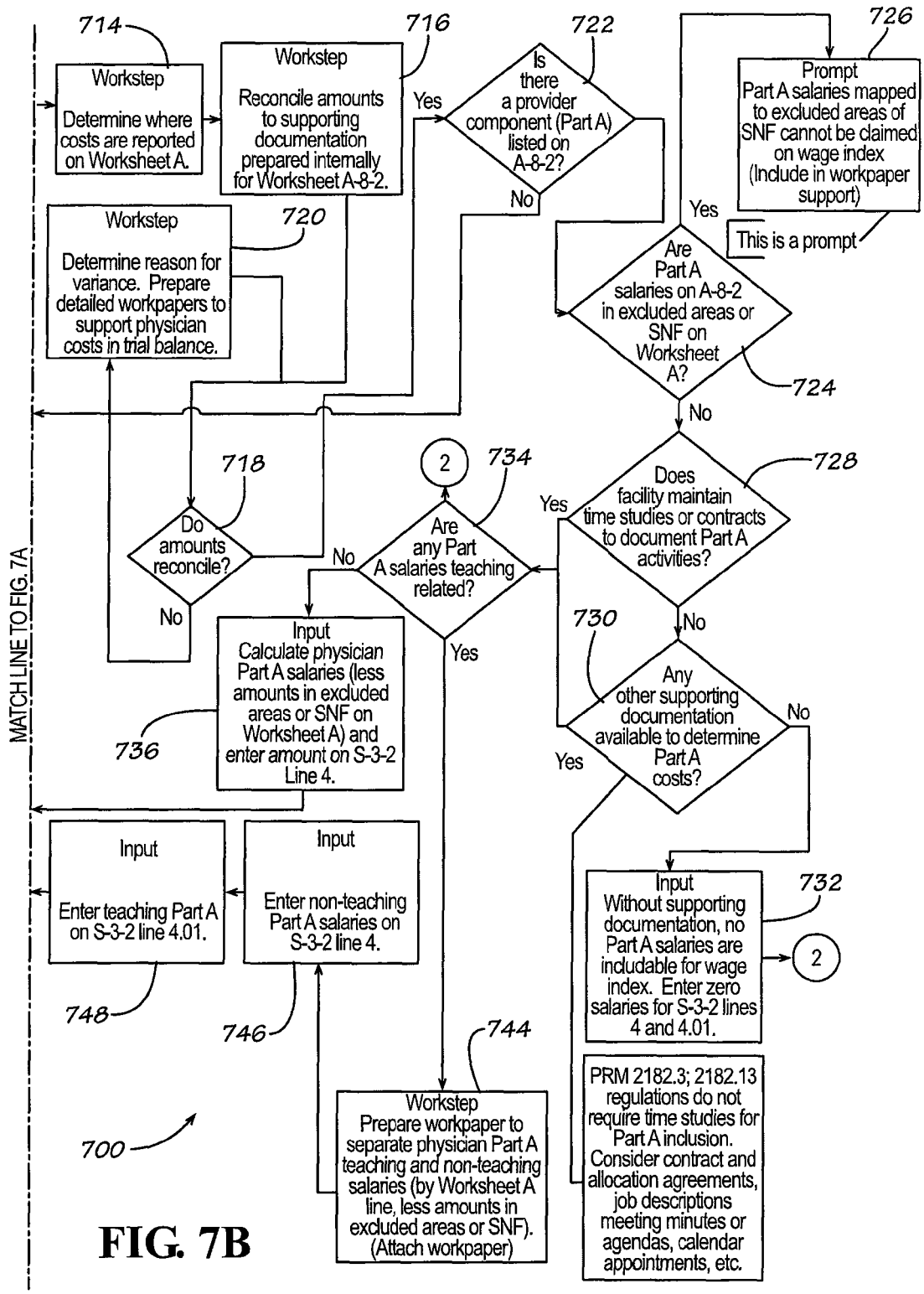

FIG. 7 shows an exemplary data gathering and compilation process 700 for computing the employed physician entry for lines 4, 4.01, 5, 10 and 10.01. This process reports employed physician information. The data sources for this process include Worksheet A, Worksheet A-8-2 and A-8-2 cost report workpapers, the ECR and PUFs. Prompts and alerts can be provided to alert the user to various rules regarding the proper entries, including the following. If user reports zero Part A administration time, consider examining contracts. Contracts must be specific to define the amount of time spent in administrative roles. Review the overall average hourly wage (AHW) for physicians, the expected range is approximately $50-$300 per hour. The facility should have documents to allocate physician time between Part A salaries, Part A teaching and Part B. The provider component (Part A) amount listed on Worksheet A-8-2 less any excluded areas should equal the sum of lines 4, 4.01, 10 and 10.012 in column 1 of S-3, Part II. Physician Part A or Part B costs applicable to excluded areas should not be included. Line 4 is included in AHW calculation.

At block 702, it is determined whether the facility employs physician, contracts with physicians or both. If the facility only contracts physicians, control is transferred to the contract physician questions beginning at block 804 of FIG. 8. Otherwise, control is transferred to block 708 to process the employed physician component. At block 708, it is documented where physician related salaries and dollars are recorded in the trial balance. Then at block 710, the amounts are traced to trial balance accounts to ensure only employed physician salaries are included in line 1 (and not contracted physician dollars). Then at block 712, it is checked whether physician salaries are included in line 1. If physician salaries are included in line 1, control is transferred to block 714. Otherwise control is transferred to block 740.

At block 714, it is determined whether costs are reported on Worksheet A. Then at block 716, amounts are reconciled to supporting documentation prepared internally for Worksheet A-8-2. Then at block 718, it is determined whether the amounts reconcile. If the amounts reconcile, control is transferred to block 722; otherwise control is transferred to block 720. At block 720, the reason for the variance is determined and detailed workpapers are prepared to support physician costs in the trial balance. Then control is returned to block 718 to determine whether the amounts reconcile.

At block 722, it is determined whether a provider component (Part A) is listed on Worksheet A-8-2. If a provider component is listed, control is transferred to block 724; otherwise control is transferred to block 738.

At block 724, it is determined whether Part A salaries on Worksheet A-8-2 for excluded areas or skilled nursing facilities (SNFs) on Worksheet A. If they are then control is transferred to block 726; otherwise control is transferred to block 728. At block 726, a prompt indicates to the user that Part A salaries mapped to excluded areas or SNFs cannot be claimed on the wage index; the prompt is also included in the workpaper support. From block 726 control passes to block 728.

At block 728, it is determined whether the facility maintains time studies or contracts to document Part A activities. If they do control is transferred to block 734; otherwise control is transferred to block 730. At block 730, it is determined whether any other supporting documentation is available to determine Part A costs. A prompt can be given at block 730 indicating that PRM 2182.3 and 2182.13 regulations do not require time studies for Part A inclusion, thus the user should consider contract and allocation agreements, job descriptions, meeting minutes or agendas, calendar appointments, etc. If other supporting documentation is available control is transferred to block 734; otherwise control is transferred to block 732. At block 732, an input is made that without supporting documentation, no Part A salaries are includable for the wage index and zero is entered for salaries on S-3-2, lines 4 and 4.01. From block 732 control passes to block 734.

At block 734, it is determined whether any Part A salaries are teaching related. If they are control is transferred to block 744; otherwise control is transferred to block 736. At block 736, physician Part A salaries, minus amounts in excluded areas or SNFs on Worksheet A, are calculated and entered on S-3-2, line 4. From block 736 control passes to block 738. At block 744, a workpaper is prepared to separate physician Part A teaching and non-teaching salaries by Worksheet A line, minus amounts in excluded areas or SNFs; and the workpaper is attached to the work step. Then at block 746, non-teaching Part A salaries are entered on S-3-2, line 4. Then at block 748, teaching Part A salaries are entered on S-3-2, line 4.01. From block 748 control passes to block 738.

At block 738, it is determined whether there is a professional component (Part B) listed on A-8-2. If there is control is transferred to block 750; otherwise control is transferred to block 740. At block 740, it is determined whether the facility has contract physicians. If the process gets to block 740, then the process skips S-3-2, lines 4, 4.01 and 5. A prompt or alert to that affect can be made to the user. If the facility has contract physicians control is transferred to block 804 of FIG. 8 to process contract physician questions; otherwise control is transferred to block 742 to proceed to the next question. At block 742, an alert can be issued to the user to understand why the response at block 702 indicated that the facility did have contract physicians.

At block 750, it is determined whether Part B salaries on A-8-2 in excluded areas or SNFs on Worksheet A. If they are control is transferred to block 752; otherwise control is transferred to block 756. At block 756, physician Part B salaries are calculated and entered on S-3-2, line 5. From block 756 control passes to block 758. At block 752, a workpaper is prepared and attached identifying Part B physician salaries by Worksheet A line number. At block 752 an alert can be given that professional component (Part B) amounts in excluded areas cannot be claimed on wage index. Then at block 754, physician Part B salaries, minus amounts in excluded areas or SNFs on Worksheet A, are calculated and entered on S-3-2, line 5. From block 754 control passes to block 758.

At block 758, it is determined whether the facility has both contract and employed physicians. If they do control is transferred to block 804 of FIG. 8 to process contract physician information; otherwise the control is transferred to block 760 to proceed to the next question.

Figure 8A:
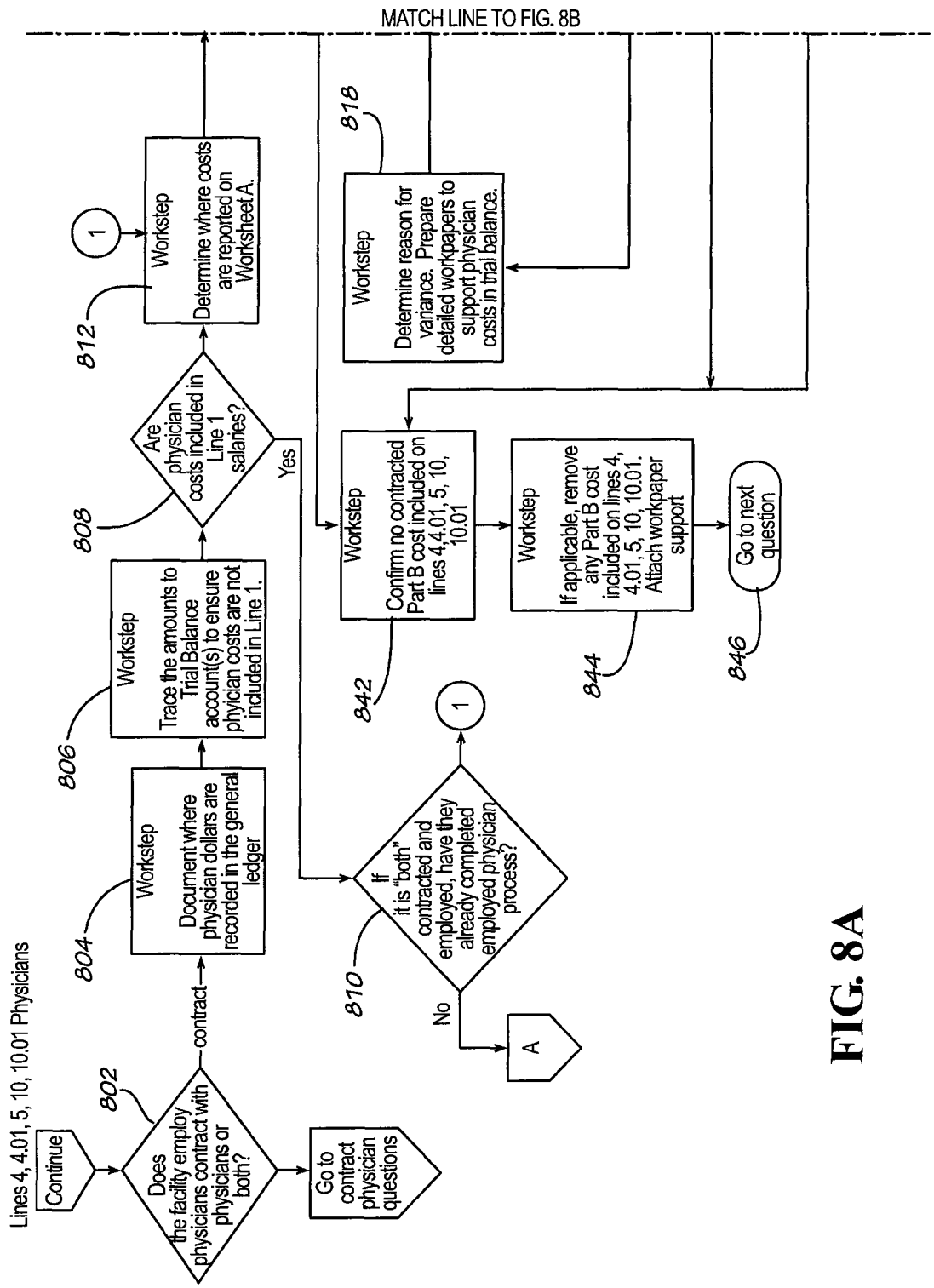
FIG. 8 shows an exemplary process for computing the contracted physician entry for lines 4, 4.01, 5, 10 and 10.01.
Figure 8B:
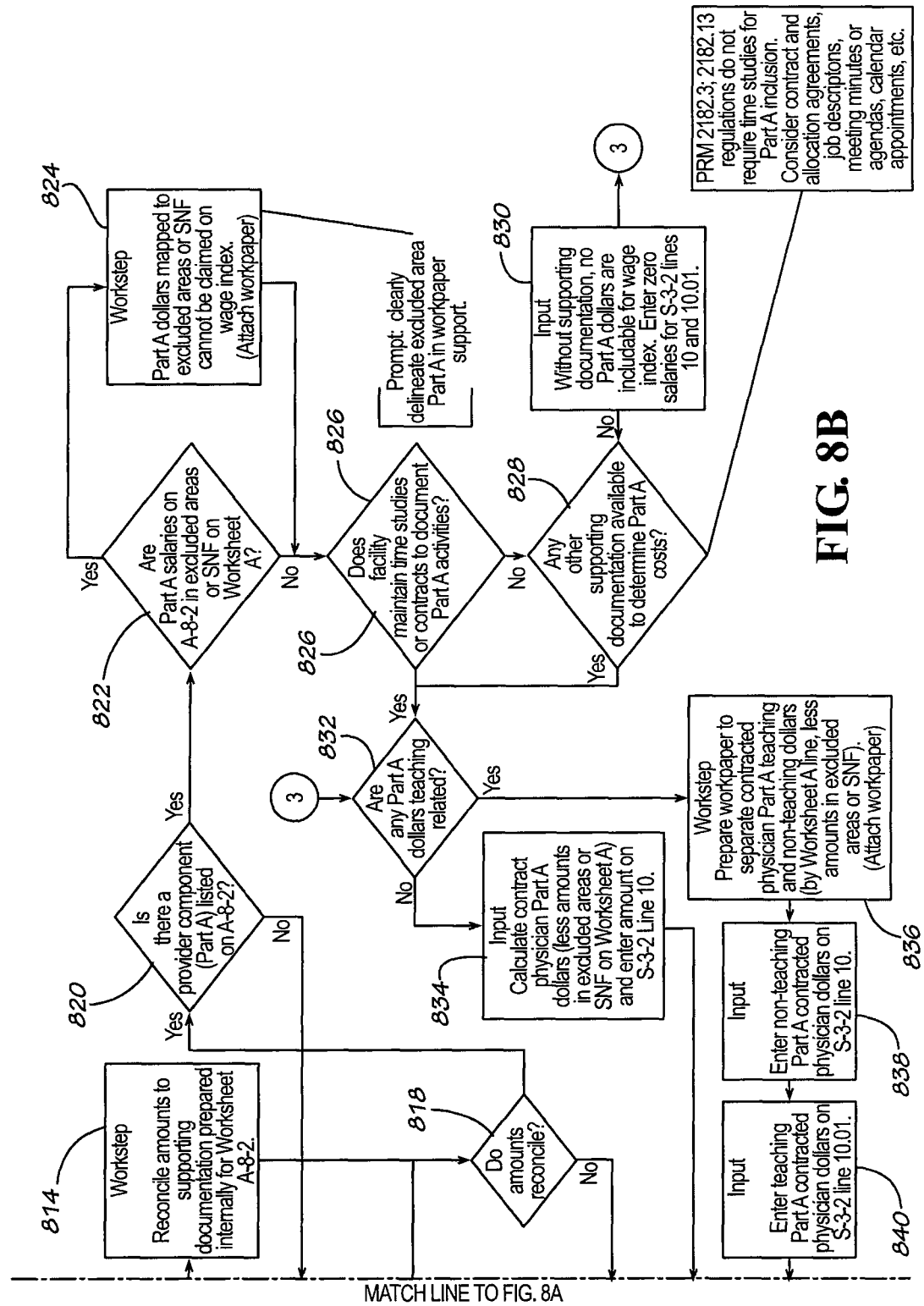

FIG. 8 shows an exemplary data gathering and compilation process 800 for computing the contracted physician entry for lines 4, 4.01, 5, 10 and 10.01. This process reports contracted physician information. The data sources for this process include Worksheet A, Worksheet A-8-2, A-8-2 cost report workpapers, the ECR and PUFs. Prompts and alerts can be provided to alert the user to various rules regarding the proper entries, including the following. If user reports zero Part A administration time, consider examining contracts. Contracts must be specific to define the amount of time spent in administrative roles. Review the overall average hourly wage (AHW) for physicians, the expected range is approximately $50-$300 per hour. The facility should have documents to allocate physician time between Part A salaries, Part A teaching and Part B. The provider component (Part A) amount listed on Worksheet A-8-2 less any excluded areas should equal the sum of lines 4, 4.01, 10 and 10.012 in column 1 of S-3, Part II. Physician Part A or Part B costs applicable to excluded areas should not be included. Line 4 is included in AHW calculation.

At block 802, it is determined whether the facility employs physician, contracts with physicians or both. At this point, in either case, control is transferred to the contract physician questions beginning at block 804. At block 804, it is documented where physician dollars are recorded in the general ledger. Then at block 806, the amounts are traced to trial balance accounts to ensure physician costs are not included in line 1. Then at block 808, it is checked whether physician costs are included in line 1 salaries. If physician costs are included in line 1 salaries, control is transferred to block 810. Otherwise control is transferred to block 812.

At block 810, it is determined, when the facility both employs and contracts physician, whether they have already completed the employed physician process. If the facility both employs and contracts physician and they have not already completed the employed physician process, then control is transferred to the employed physician process beginning at block 708 of FIG. 7. Otherwise control is transferred to block 812.

At block 812, it is determined whether costs are reported on Worksheet A. Then at block 814, amounts are reconciled to supporting documentation prepared internally for Worksheet A-8-2. Then at block 816, it is determined whether the amounts reconcile. If the amounts reconcile, control is transferred to block 820; otherwise control is transferred to block 818. At block 818, the reason for the variance is determined and detailed workpapers are prepared to support physician costs in the trial balance. Then control is returned to block 816 to determine whether the amounts reconcile.

At block 820, it is determined whether a provider component (Part A) is listed on Worksheet A-8-2. If a provider component is listed, control is transferred to block 822; otherwise control is transferred to block 842.

At block 822, it is determined whether Part A salaries on Worksheet A-8-2 for excluded areas or skilled nursing facilities (SNFs) on Worksheet A. If they are then control is transferred to block 824; otherwise control is transferred to block 826. At block 824, a prompt indicates to the user that Part A salaries mapped to excluded areas or SNFs cannot be claimed on the wage index; the prompt is also included in workpaper support. From block 824 control passes to block 826.

At block 826, it is determined whether the facility maintains time studies or contracts to document Part A activities. If they do control is transferred to block 832; otherwise control is transferred to block 828. At block 828, it is determined whether any other supporting documentation is available to determine Part A costs. A prompt can be given at block 828 indicating that PRM 2182.3 and 2182.13 regulations do not require time studies for Part A inclusion, thus the user should consider contract and allocation agreements, job descriptions, meeting minutes or agendas, calendar appointments, etc. If other supporting documentation is available control is transferred to block 832; otherwise control is transferred to block 830. At block 830, an alert is given that without supporting documentation, no Part A dollars are includable for the wage index and zero is entered for salaries on S-3-2, lines 10 and 10.01. From block 830 control passes to block 832.

At block 832, it is determined whether any Part A dollars are teaching related. If they are control is transferred to block 836; otherwise control is transferred to block 834. At block 834, contract physician Part A dollars, minus amounts in excluded areas or SNFs on Worksheet A, are calculated and entered on S-3-2, line 10. From block 834 control passes to block 842. At block 836, a workpaper is prepared to separate contracted physician Part A teaching and non-teaching dollars by Worksheet A line, minus amounts in excluded areas or SNFs; and the workpaper is attached to the work step. Then at block 838, non-teaching Part A contracted physician dollars are entered on S-3-2, line 10. Then at block 840, teaching Part A contracted physician dollars are entered on S-3-2, line 10.01. From block 840 control passes to block 842.

At block 842, it is confirmed that no contracted Part B costs are included on lines 4, 4.01, 5, 10 or 10.01. Then at block 844, any Part B costs included on lines 4, 4.01, 5, 10 or 10.01 are removed and a supporting workpaper is attached. Then control is transferred to block 846 to proceed to the next question.

Figure 9:
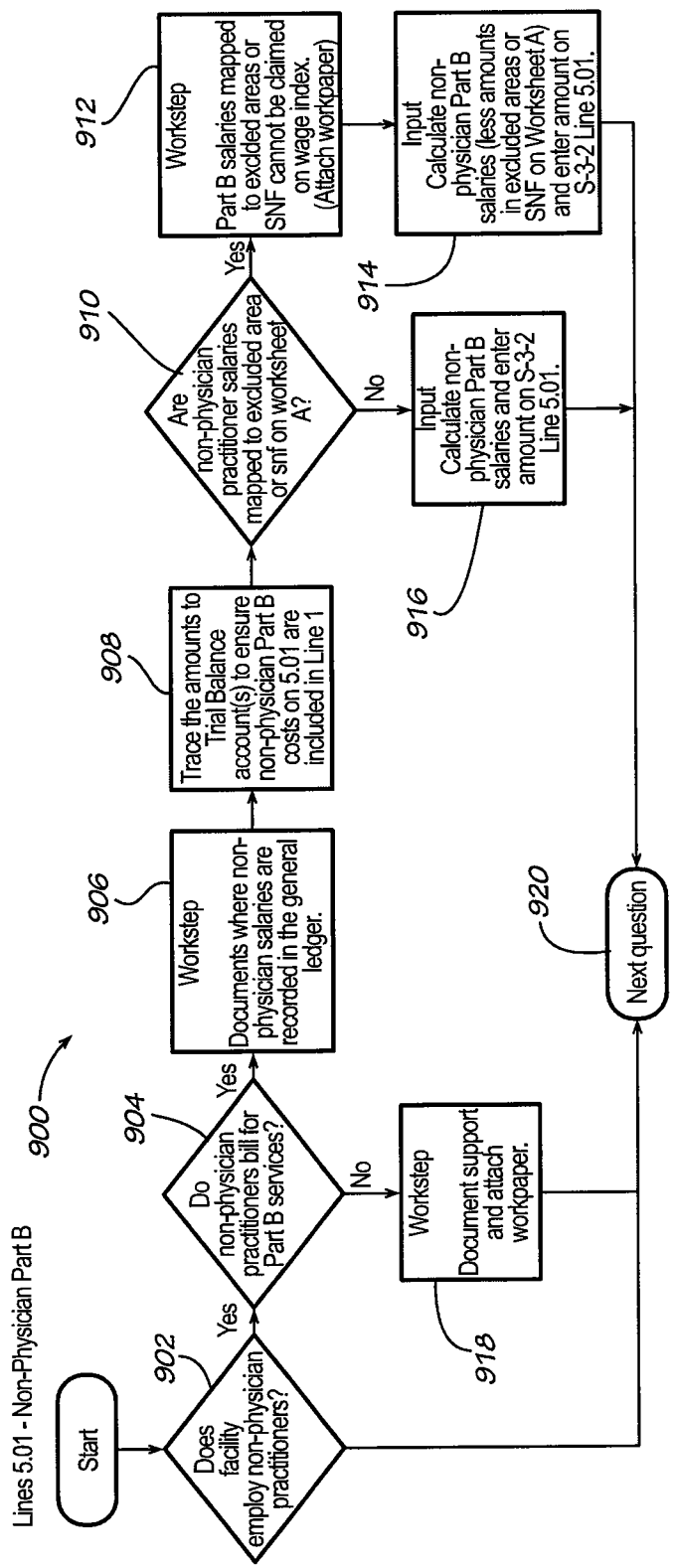
FIG. 9 shows an exemplary process for computing the non-physician Part B entry for line 5.01.

FIG. 9 shows an exemplary data gathering and compilation process 900 for computing the non-physician Part B entry for line 5.01. This process reports the non-physician salaries for patient care services reported for hospital based RHCs and FQHCs services included on Worksheet A, column 1, line 63. Prompts and alerts can be provided to alert the user to various rules regarding the proper entries, including the following. Physician Part A and Part B costs applicable to excluded areas should not be included. Line 5 is not included in the AHW calculation. Amounts should only be reported to the extent that hours can be accurately determined.

At block 902, it is determined whether the facility employs non-physician practitioners. If the facility does not employ non-physician practitioners, control is transferred to block 920 which proceeds to the next question. If the facility does employ non-physician practitioners, control is transferred to block 904.

At block 904, it is determined whether non-physician practitioners bill for Part B services. If non-physician practitioners do not bill for Part B services, control is transferred to block 918 where support for the determination is documented and attached as a workpaper. From block 918 control passes to block 920 which proceeds to the next question. If non-physician practitioners do bill for Part B services, control is transferred to block 906.

At block 906, it is documented where non-physician salaries are recorded in the general ledger. Then at block 908, the amounts are traced to trial balance account(s) to ensure non-physician Part B costs on line 5.01 are included in line 1. Then at block 910, it is determined whether non-physician practitioner salaries are mapped to excluded areas or SNFs on Worksheet A. If non-physician practitioner salaries are mapped to excluded areas or SNFs on Worksheet A control is transferred to block 912; otherwise control is transferred to block 916.

At block 912, a prompt is provided that Part B salaries mapped to excluded areas or SNFs cannot be claimed on the wage index. Then at block 914, Part B salaries minus amounts in excluded areas or SNFs on Worksheet A are calculated and the amount is entered on S-3-2, line 5.01. Control is transferred from block 914 to block 920 which proceeds to the next question.

At block 916, non-physician Part B salaries are calculated and the amount is entered on S-3-2, line 5.01. Control is transferred from block 916 to block 920 which proceeds to the next question.

Figure 10:
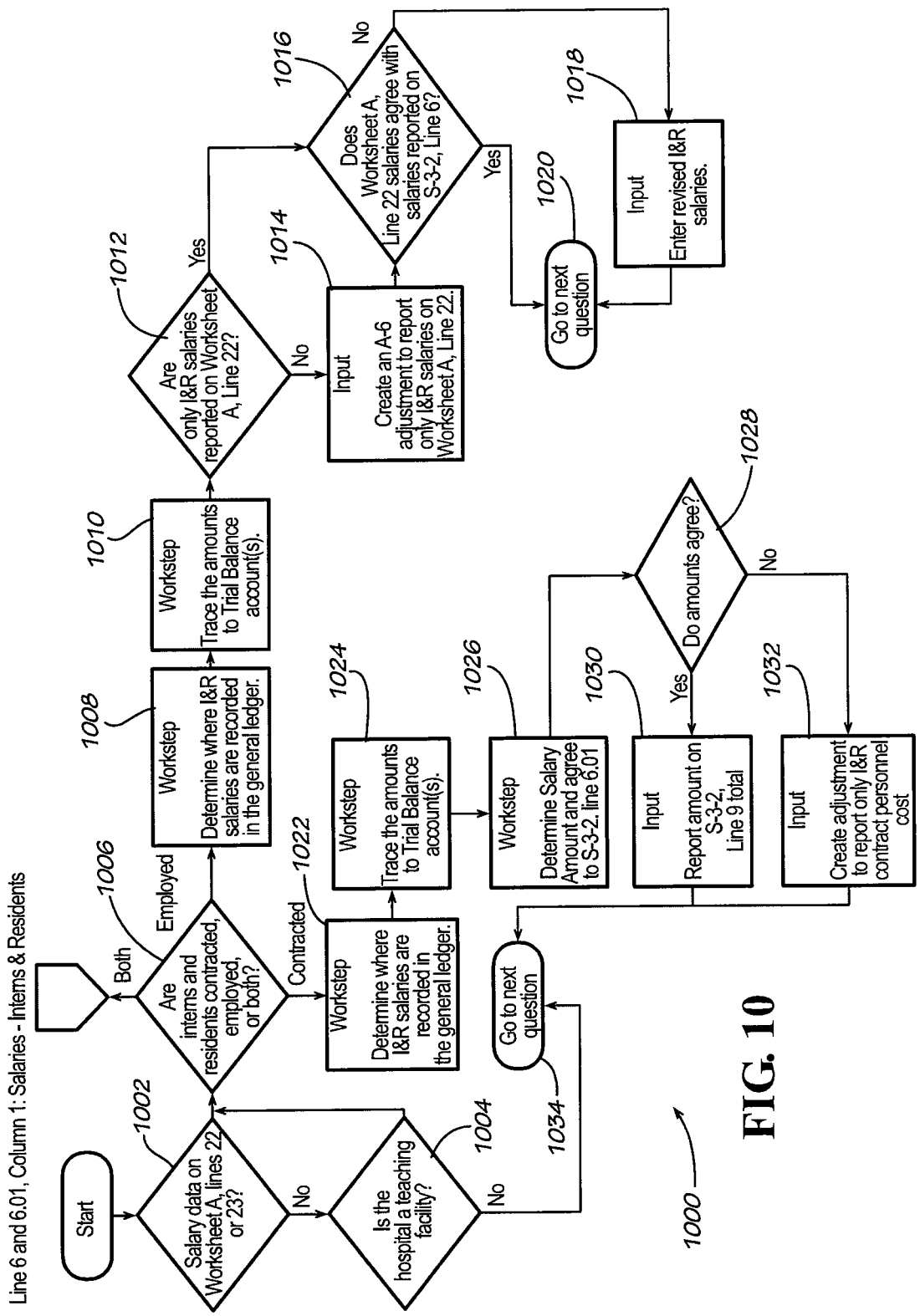
FIGS. 10 and 11 show an exemplary process for computing the interns and residents salaries entry for lines 6 and 6.01.
Figure 11:
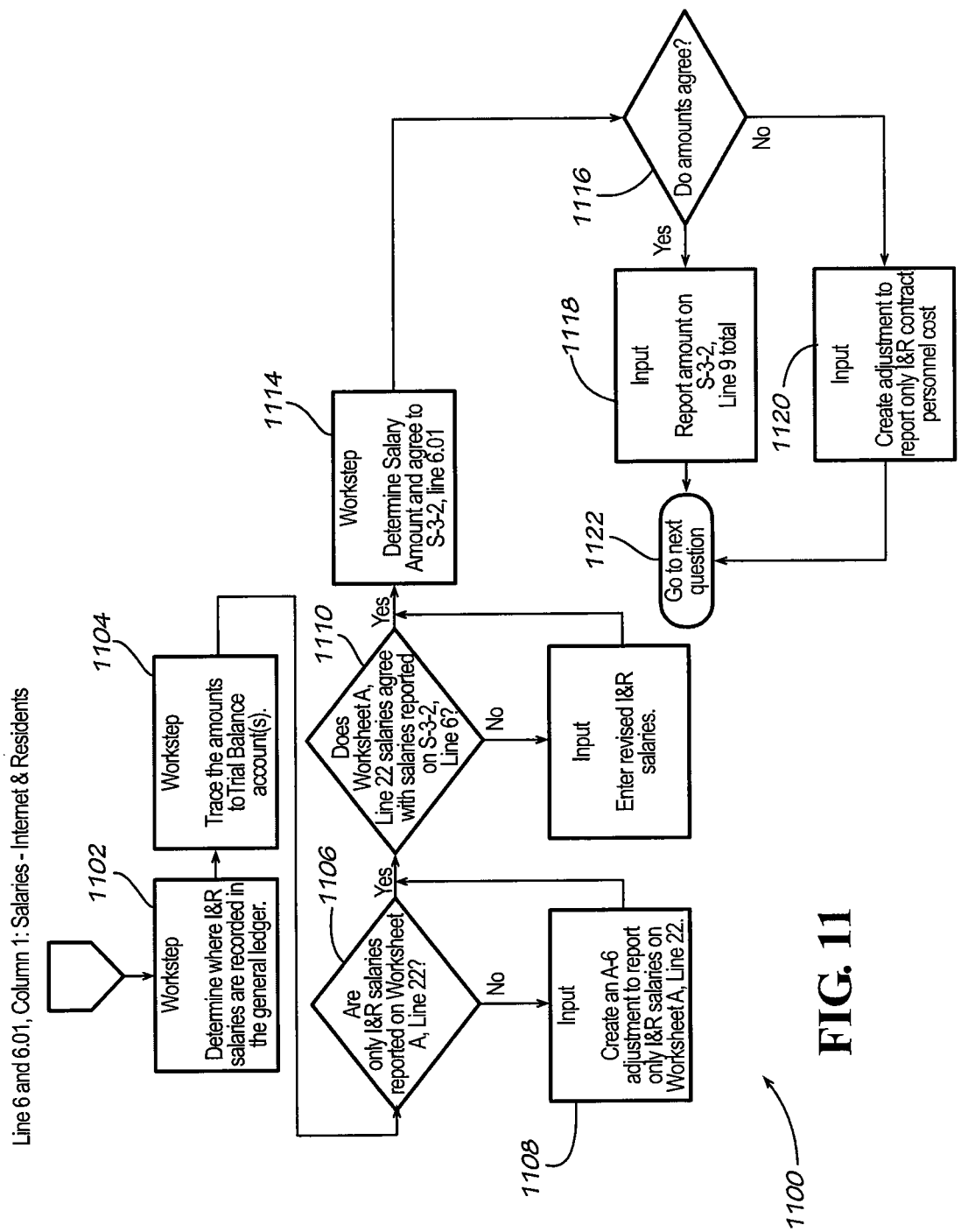

FIGS. 10 and 11 show an exemplary data gathering and compilation process 1000 and 1100 for computing the interns and residents salaries entry for lines 6 and 6.01. This process identifies and documents salaries and wages for interns and residents, if applicable. The data sources for this process include audited trial balance, Worksheet A and ECR data, contract intern and resident detail (if applicable), and employed intern and resident salary to hour detail (if applicable). Prompts and alerts can be provided to alert the user to various rules regarding the proper entries, including the following. Worksheet A salaries are reported in column 1 of line 22 for interns and residents. Report employed interns and residents on line 6 and contracted interns and residents on line 6.01. Report only the personnel costs associated with any intern and resident contracts. Equipment, supplies, travel expenses and other miscellaneous or overhead costs should not be included. Costs applicable to excluded areas should also not be included.

At block 1002, it is determined whether salary data is reported on Worksheet A, lines 22 or 23. If salary data is reported on Worksheet A, lines 22 or 23, control is transferred to block 1006; otherwise control is transferred to block 1004. At block 1004, it is determined whether the hospital is a teaching facility. If it is a teaching facility control is transferred to block 1006; otherwise control is transferred to block 1034 where the system goes to the next question and avoids inapplicable inquiries.

At block 1006, it is determined whether interns and residents are contracted, employed or both. If interns and residents are only employed control is transferred to block 1008. If interns and residents are only contracted control is transferred to block 1022. If interns and residents are both employed and contracted control is transferred to block 1102 of FIG. 11.

At block 1008, it is determined where intern and resident salaries are recorded in the general ledger. Then at block 1010, the amounts are traced to trial balance account(s). Then at block 1012, it is determined whether only intern and resident salaries are reported on Worksheet A, line 22. If it is only intern and resident salaries reported on Worksheet A, line 22 control is transferred to block 1016. If it is not only intern and resident salaries reported on Worksheet A, line 22 control is transferred to block 1014. At block 1014, an A-6 adjustment is created to report only intern and resident salaries on Worksheet A, line 22. Control is transferred from block 1014 to block 1016.

At block 1016, it is determined whether Worksheet A, line 22 salaries agree with salaries reported on S-3-2, line 6. If they agree control is transferred to block 1020. If they do not agree control is transferred to block 1018. At block 1018, revised intern and resident salaries are entered. From block 1018 control is transferred to block 1020. At block 1020 the system goes to the next question.

At block 1022, it is determined where intern and resident salaries are recorded in the general ledger. Then at block 1024, the amounts are traced to trial balance account(s). Then at block 1026, it is determined whether salary amounts agree with amounts reported on S-3-2, line 6.01. Then at block 1028, it is checked whether the salary amounts agree. If the salary amounts agree control is transferred to block 1030. If the salary amounts do not agree control is transferred to block 1032. At block 1030, the amount on S-3-2, line 9 total is reported and control is passed to block 1034. At block 1032, an adjustment is created to report only intern and resident contract personnel costs and control is passed to block 1034. At block 1034 the system goes to the next question.

At block 1102, it is determined where intern and resident salaries are recorded in the general ledger. Then at block 1104, the amounts are traced to trial balance account(s). Then at block 1106, it is determined whether only intern and resident salaries are reported on Worksheet A, line 22. If it is only intern and resident salaries reported on Worksheet A, line 22 control is transferred to block 1110. If it is not only intern and resident salaries reported on Worksheet A, line 22 control is transferred to block 1108. At block 1108, an A-6 adjustment is created to report only intern and resident salaries on Worksheet A, line 22. Control is transferred from block 1108 to block 1110.

At block 1110, it is determined whether Worksheet A, line 22 salaries agree with salaries reported on S-3-2, line 6. If they agree control is transferred to block 1114. If they do not agree control is transferred to block 1112. At block 1112, revised intern and resident salaries are entered. From block 1112 control is transferred to block 1114.

At block 1114, it is determined whether salary amounts agree with amounts reported on S-3-2, line 6.01. Then at block 1116, it is checked whether the salary amounts agree.

If the salary amounts agree control is transferred to block 1118. If the salary amounts do not agree control is transferred to block 1120. At block 1118, the amount on S-3-2, line 9 total is reported and control is passed to block 1122. At block 1120, an adjustment is created to report only intern and resident contract personnel costs and control is passed to block 1122. At block 1122 the system goes to the next question.

Figure 12:
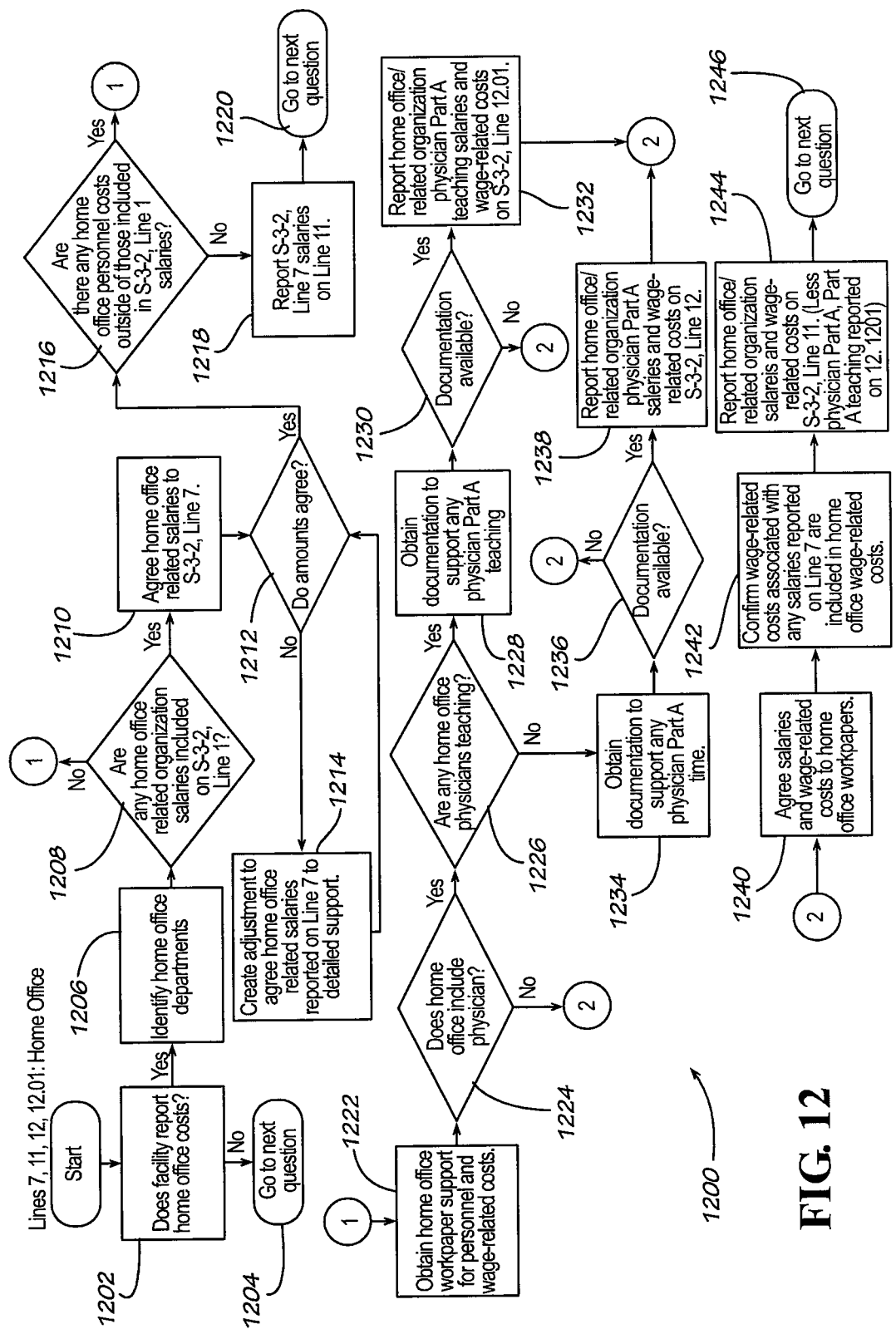
FIG. 12 shows an exemplary process for computing the home office entry for lines 7, 11, 12 and 12.01.

FIG. 12 shows an exemplary data gathering and compilation process 1200 for computing the home office entry for lines 7, 11, 12 and 12.01. This process captures and reports salaries and wages and wage related costs. The data sources for this process include audited trial balance, home office and related party workpapers, Worksheet A-8-1, ECR and S-3, Part II PUFs. Prompts and alerts can be provided to alert the user to various rules regarding the proper entries.

At block 1202, it is determined whether the facility reports home office costs. If the facility does not report home office costs, control is transferred to block 1204 which proceeds to the next question and avoids inapplicable inquiries. If the facility does report home office costs, control is transferred to block 1206. At block 1206, home office departments are identified. Then at block 1208, it is determined whether any home office related organization salaries are included on S-3-2, line 1. If they are control is transferred to block 1210; otherwise control is transferred to block 1222.

At block 1210, home office related salaries are compared to S-3-2, line 7 and at block 1212 it is determined whether the amounts agree. If the amounts agree control is transferred to block 1216. If the amounts do not agree control is transferred to block 1214. At block 1214, an adjustment is created to make home office related salaries agree with S-3-2, line 7 with detailed support. Control is transferred from block 1214 back to block 1212 to ensure that the amounts agree.

At block 1216, it is determined whether there are any home office personnel costs outside of those included in S-3-2, line 1 salaries. If there are control is transferred to block 1222; otherwise control is transferred to block 1218. At block 1218, S-3-2, line 7 salaries are reported on line 11. Then at block 1220, the system proceeds to the next question.

At block 1222, home office workpaper support is obtained for personnel and wage related costs. Then at block 1224, it is determined whether the home office includes physicians. If home office does include physicians control is transferred to block 1226; otherwise control is transferred to block 1240.

At block 1226, it is determined whether any home office physicians are teaching. If any home office physicians are teaching control is transferred to block 1228; otherwise control is transferred to block 1234. At block 1228, documentation is obtained to support any physician Part A teaching and control is transferred to block 1230. At block 1230, it is determined whether any documentation is available. If documentation is available control is transferred to block 1232; otherwise control is transferred to block 1240. At block 1232, home office related organization physician Part A teaching salaries and wage related costs are reported on S-3-2, line 12.01. Control is transferred from block 1232 to block 1240.

At block 1234, documentation is obtained to support any physician Part A time and control is transferred to block 1236. At block 1236, it is determined whether any documentation is available. If documentation is available control is transferred to block 1238; otherwise control is transferred to block 1240. At block 1238, home office related organization physician Part A salaries and wage related costs are reported on S-3-2, line 12. Control is transferred from block 1238 to block 1240.

At block 1240, salaries and wage related costs are agreed to home office workpapers. Then at block 1242, it is confirmed that wage related costs associated with any salaries reported on line 7 are included in home office wage related costs. Then at block 1244, home office related organization salaries and wage related costs are reported on S-3-2, line 11 minus physician Part A and Part A teaching reported on lines 12 and 12.01, respectively. Then at block 1246 the system goes to the next question.

Figure 13:
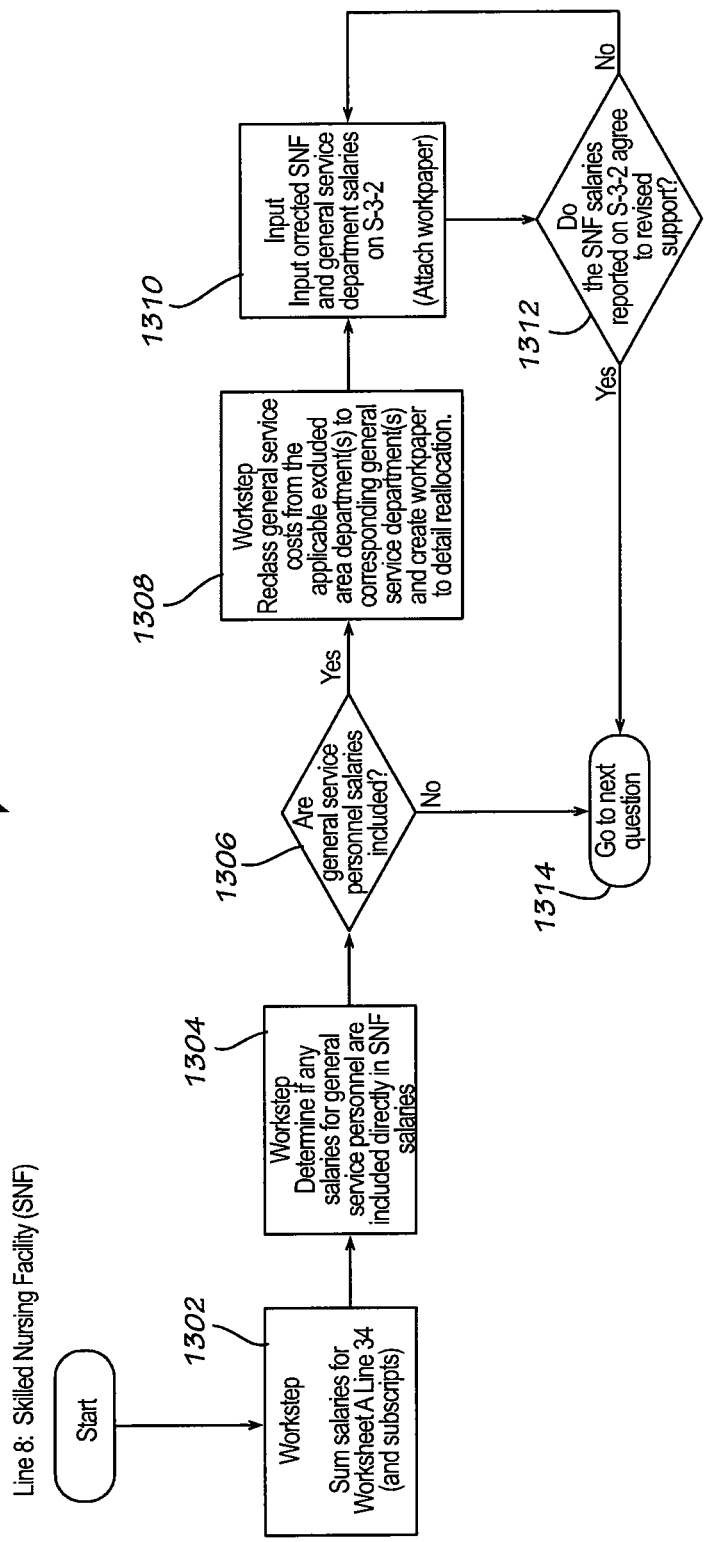
FIG. 13 shows an exemplary process for computing the skilled nursing facility (SNF) entry for line 8.

FIG. 13 shows an exemplary data gathering and compilation process 1300 for computing the skilled nursing facility (SNF) entry for line 8. This process confirms SNF salaries. The data sources for this process include audited trial balance, and PUF S-3-2, line 8, column 1. Prompts and alerts can be provided to alert the user to various rules regarding the proper entries.

At block 1302, salaries for Worksheet A, line 34 and subscripts are summed. At block 1304, it is determined if any salaries for general service personnel are included directly in SNF salaries. At block 1306, it is checked whether general service personnel salaries are included directly in SNF salaries. If general service personnel salaries are not included control is transferred to block 1314 which proceeds to the next question. If general service personnel salaries are included control is transferred to block 1308. At block 1308, general service costs from the applicable excluded area department(s) is reclassed to corresponding general service department(s) and a workpaper is created to detail the reallocation. Then at block 1310, corrected SNF and general service department salaries input on S-3-2 and can include an attached workpaper. Then at block 1312, it is determined whether the SNF salaries reported on S-3-2 agree with the revised support. If they do not agree control is passed back to block 1310. If they agree control is transferred to block 1314 which goes to the next question.

Figure 14:
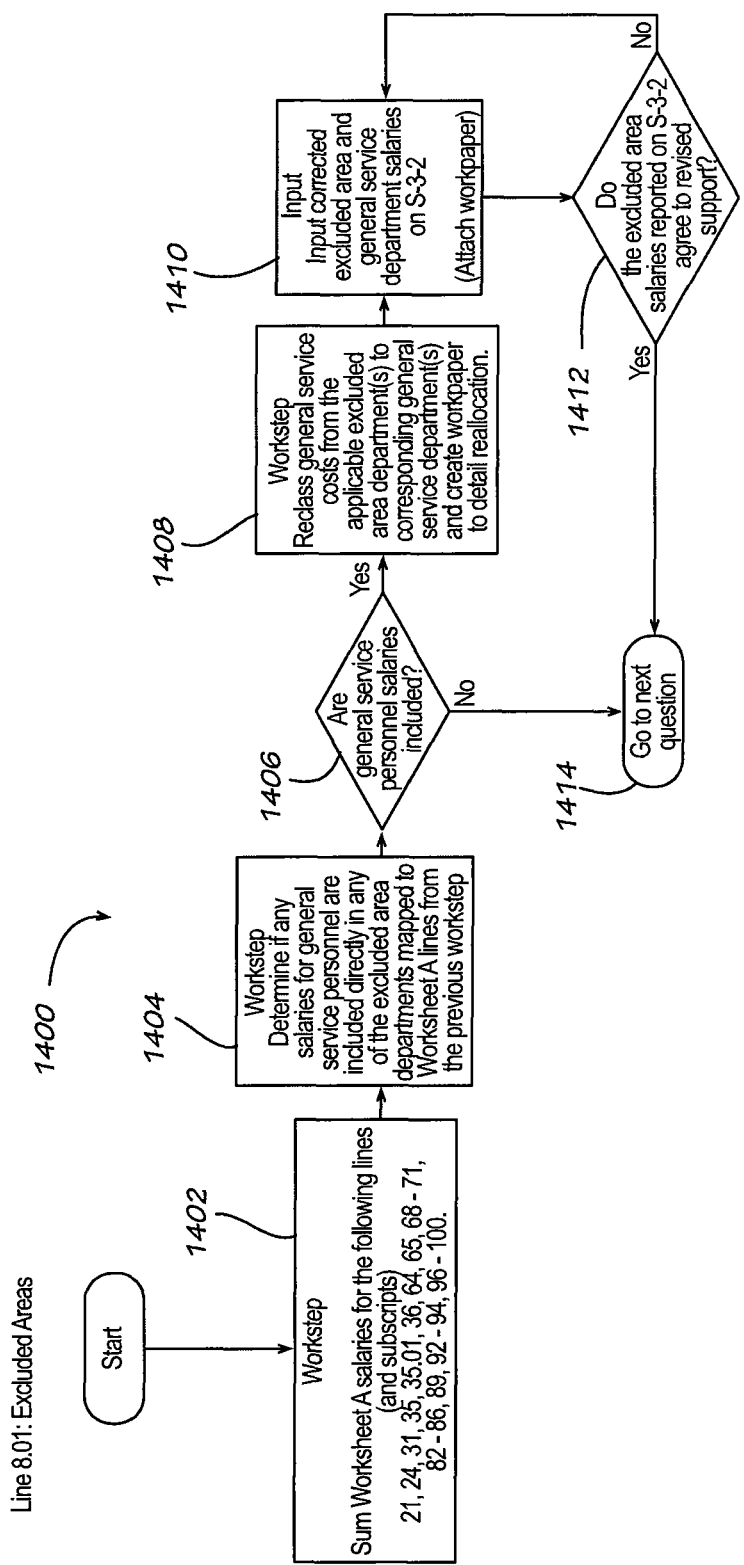
FIG. 14 shows an exemplary process for computing the excluded areas entry for line 8.01.
Figure 15:
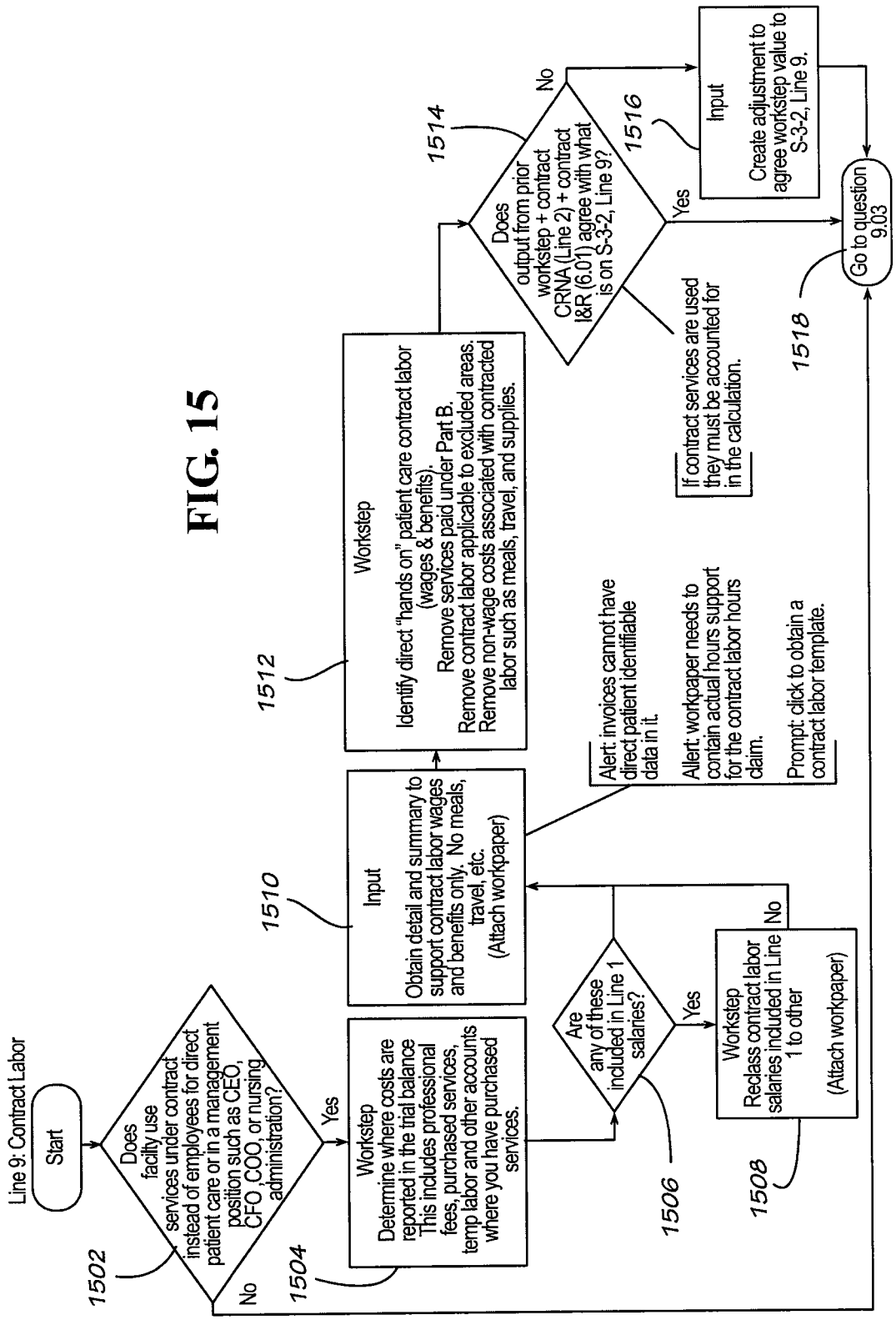
FIG. 15 shows an exemplary processes for computing the contract labor entry for line 9.

FIG. 14 shows an exemplary data gathering and compilation process 1400 for computing the excluded areas entry for line 8.01. This process confirms excluded area salaries. The data sources for this process include audited trial balance, and PUF S-3-2, line 8.01, column 1. Prompts and alerts can be provided to alert the user to various rules regarding the proper entries.

At block 1402, Worksheet A salaries for lines 21, 24, 31, 35, 35.01, 36, 64, 65, 68-71, 82-86, 89, 92-94 and 96-100 and subscripts are summed. At block 1404, it is determined if any salaries for general service personnel are included directly in any of the excluded area departments mapped to Worksheet A lines 21, 24, 31, 35, 35.01, 36, 64, 65, 68-71, 82-86, 89, 92-94 and 96-100. At block 1406, it is checked whether general service personnel salaries are included. If general service personnel salaries are not included control is transferred to block 1414 which proceeds to the next question. If general service personnel salaries are included control is transferred to block 1408. At block 1408, general service costs from the applicable excluded area department(s) is reclassed to corresponding general service department(s) and a workpaper is created to detail the reallocation. Then at block 1410, corrected excluded area and general service department salaries input on S-3-2 and can include an attached workpaper. Then at block 1412, it is determined whether the excluded area salaries reported on S-3-2 agree with the revised support. If they do not agree control is passed back to block 1410. If they agree control is transferred to block 1414 which goes to the next question.

FIGS. 15-19 shows exemplary data gathering and compilation processes 1500-1900, respectively, for computing the contract labor entries for lines 9, 9.03, 22.01, 26.01 and 27.01. These processes document includable wages and benefits for services provided under contract. The data sources for these processes include contract labor invoices and supporting workpapers, audited trial balance, ECR and PUF. Prompts and alerts can be provided to alert the user to various rules regarding the proper entries. For example, lines 9.01 and 9.02 should be zero.

At block 1502, it is determined whether the facility uses services under contract instead of employees for direct patient care or in a management position such as CEO, CFO, COO or nursing administration. If the facility does not use such services under contract then control is transferred to block 1518 which proceeds to the next question. If the facility does use such services under contract then control is transferred to block 1504.

At block 1504, it is determined where costs are reported in the trial balance, including professional fees, purchased services, temporary labor and other accounts where services are purchased. Then at block 1506 it is checked whether any of these costs are included in line 1 salaries. If these costs are included in line 1 salaries control is transferred to block 1508; otherwise control is transferred to block 1510. At block 1508, contract labor salaries included in line 1 are reclassed to other and a workpaper is attached. Then control is transferred to block 1510.

At block 1510, details and summaries are obtained to support contract labor wages and benefits only (no meals, travel etc.) and a workpaper is attached. Block 1510 can include a contract labor template to help the user prepare the workpaper. Alerts can also be given at block 1510 to inform the user that invoices should not include direct patient identifiable data, and that the workpaper needs to contain actual hours support for contract labor hours claim. Then at block 1512, direct "hands-on" patient care contract labor wages and benefits are identified and the following are removed: services paid under Part B, contract labor applicable to excluded areas, non-wage costs associated with contracted labor such as meals, travel and supplies. Then at block 1514, it is checked whether the output from block 1512 plus contract non-physician anesthetist from line 2 plus contract intern and resident from line 6.01 agrees with what is reported on S-3-2, line 9. An alert can be given at step 1514 that if contract services are used, they must be accounted for in the calculation. If they agree control is transferred to block 1518 which goes to the next question; otherwise control is transferred to block 1516. At block 1516, an adjustment is created to make the value computed in block 1514 agree with what is reported on S-3-2, line 9. Then control is transferred to block 1518 which goes to block 1602 in FIG. 16.

Figure 16:
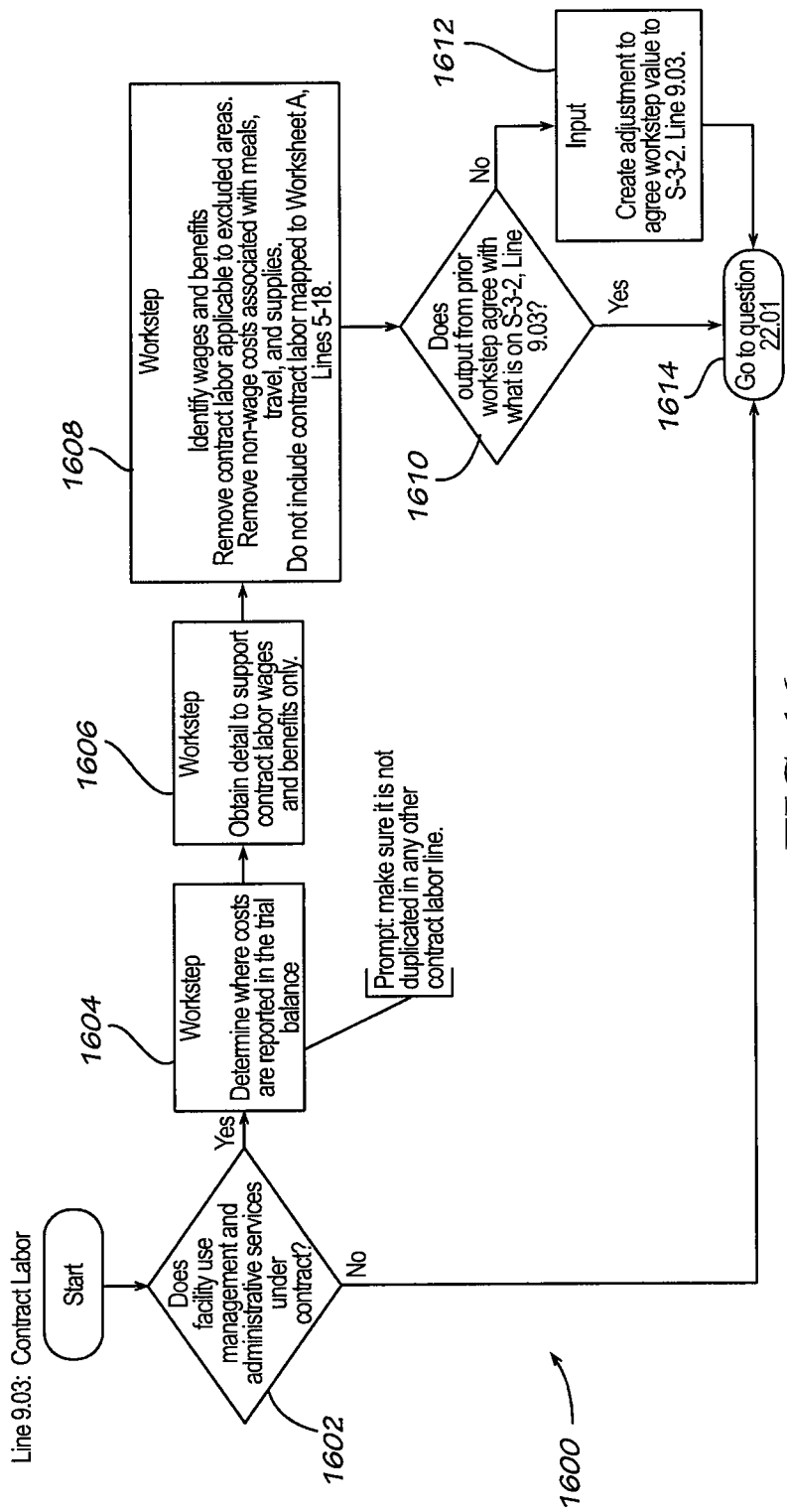
FIG. 16 shows an exemplary processes for computing the contract labor entry for line 9.03.

In FIG. 16, at block 1602, it is determined whether the facility uses management and administrative services under contract. If the facility does not use such services under contract then control is transferred to block 1614 which proceeds to the next question. If the facility does use such services under contract then control is transferred to block 1604.

At block 1604, it is determined where costs are reported in the trial balance. Block 1604 can include a prompt to make sure it is not duplicated in any other contract labor line. Then at block 1606 details are obtained to support contract labor wages and benefits only (no meals, travel etc.). Then at block 1608, wages and benefits are identified and the following are removed: contract labor applicable to excluded areas; non-wage costs associated with meals, travel and supplies; and contract labor mapped to Worksheet A, lines 5-18. Then at block 1610, it is checked whether the output from block 1608 agree with what is reported on S-3-2, line 9.03. If it agrees control is transferred to block 1614 which goes to the next question; otherwise control is transferred to block 1612. At block 1612, an adjustment is created to make the value computed in block 1608 agree with what is reported on S-3-2, line 9.03. Then control is transferred to block 1614 which goes to block 1702 in FIG. 17.

Figure 17:
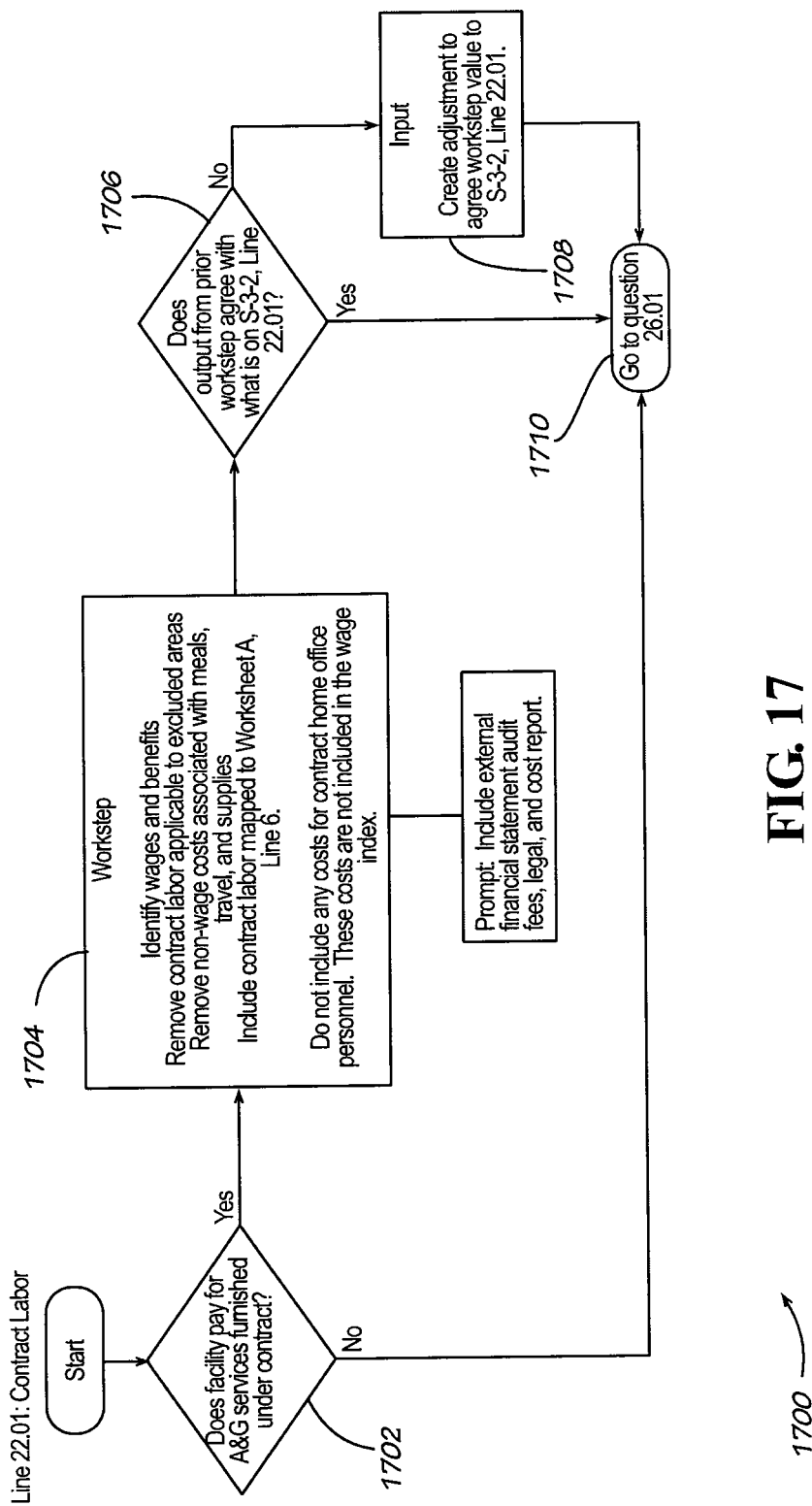
FIG. 17 shows an exemplary processes for computing the contract labor entry for line 22.01.

In FIG. 17, at block 1702, it is determined whether the facility pays for administrative and general services under contract. If the facility does not pay for such services under contract then control is transferred to block 1710 which proceeds to the next question. If the facility does pay for such services under contract then control is transferred to block 1704.

At block 1704, wages and benefits are identified and the following are removed: contract labor applicable to excluded areas; non-wage costs associated with meals, travel and supplies; any costs for contract home office personnel, and include contract labor mapped to Worksheet A, line 6. Block 1704 can include a prompt to include external financial statement audit fees, legal and cost report. Then at block 1706, it is checked whether the output from block 1704 agrees with what is reported on S-3-2, line 22.01. If it agrees control is transferred to block 1710 which goes to the next question; otherwise control is transferred to block 1708. At block 1708, an adjustment is created to make the value computed in block 1704 agree with what is reported on S-3-2, line 22.01. Then control is transferred to block 1710 which goes to block 1802 in FIG. 18.

Figure 18:
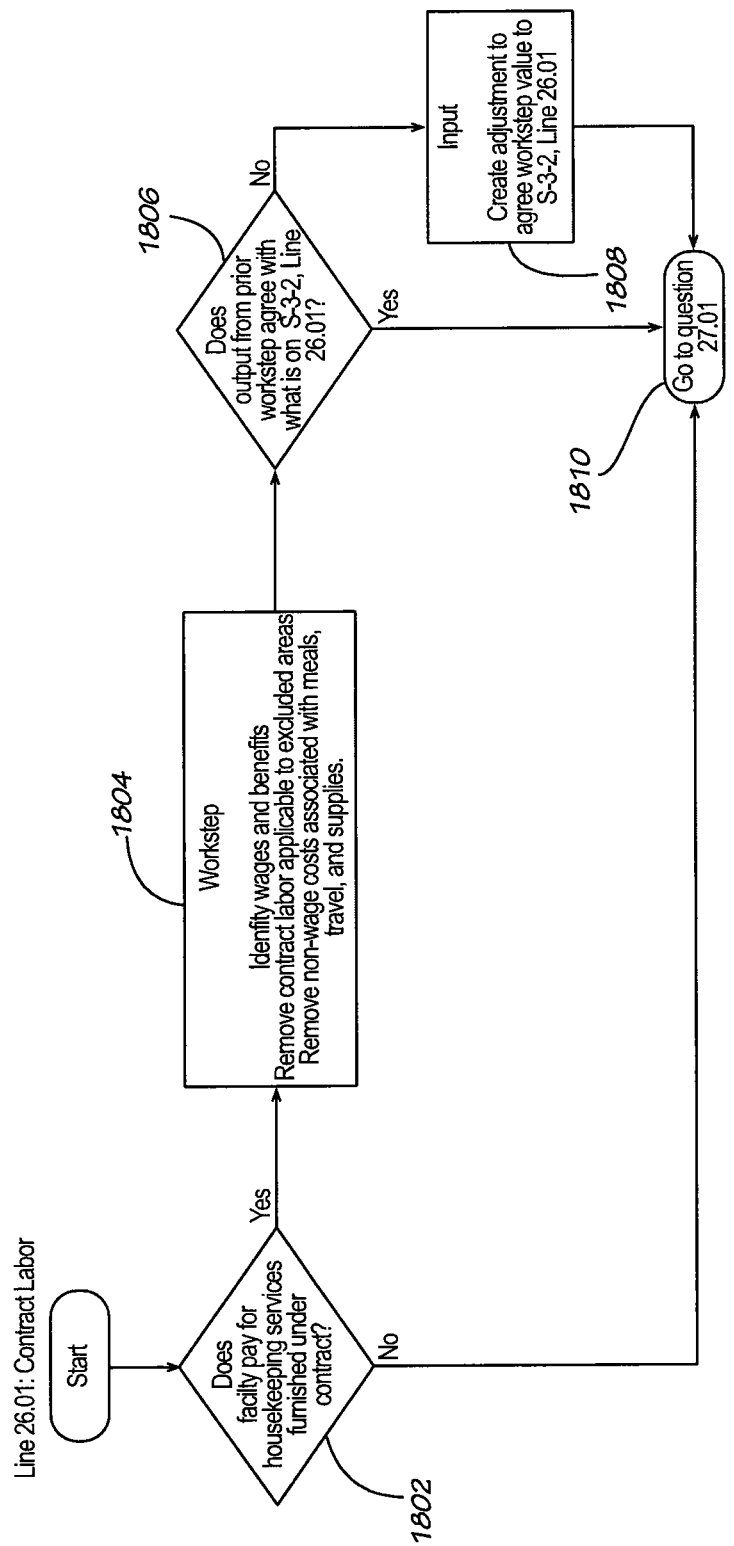
FIG. 18 shows an exemplary processes for computing the contract labor entry for line 26.01.

In FIG. 18, at block 1802, it is determined whether the facility pays for housekeeping services furnished under contract. If the facility does not pay for such services under contract then control is transferred to block 1810 which proceeds to the next question. If the facility does pay for such services under contract then control is transferred to block 1804.

At block 1804, wages and benefits are identified and the following are removed: contract labor applicable to excluded areas; and non-wage costs associated with meals, travel and supplies. Then at block 1806, it is checked whether the output from block 1804 agrees with what is reported on S-3-2, line 26.01. If it agrees control is transferred to block 1810 which goes to the next question; otherwise control is transferred to block 1808. At block 1808, an adjustment is created to make the value computed in block 1804 agree with what is reported on S-3-2, line 26.01. Then control is transferred to block 1810 which goes to block 1902 in FIG. 19.

Figure 19:
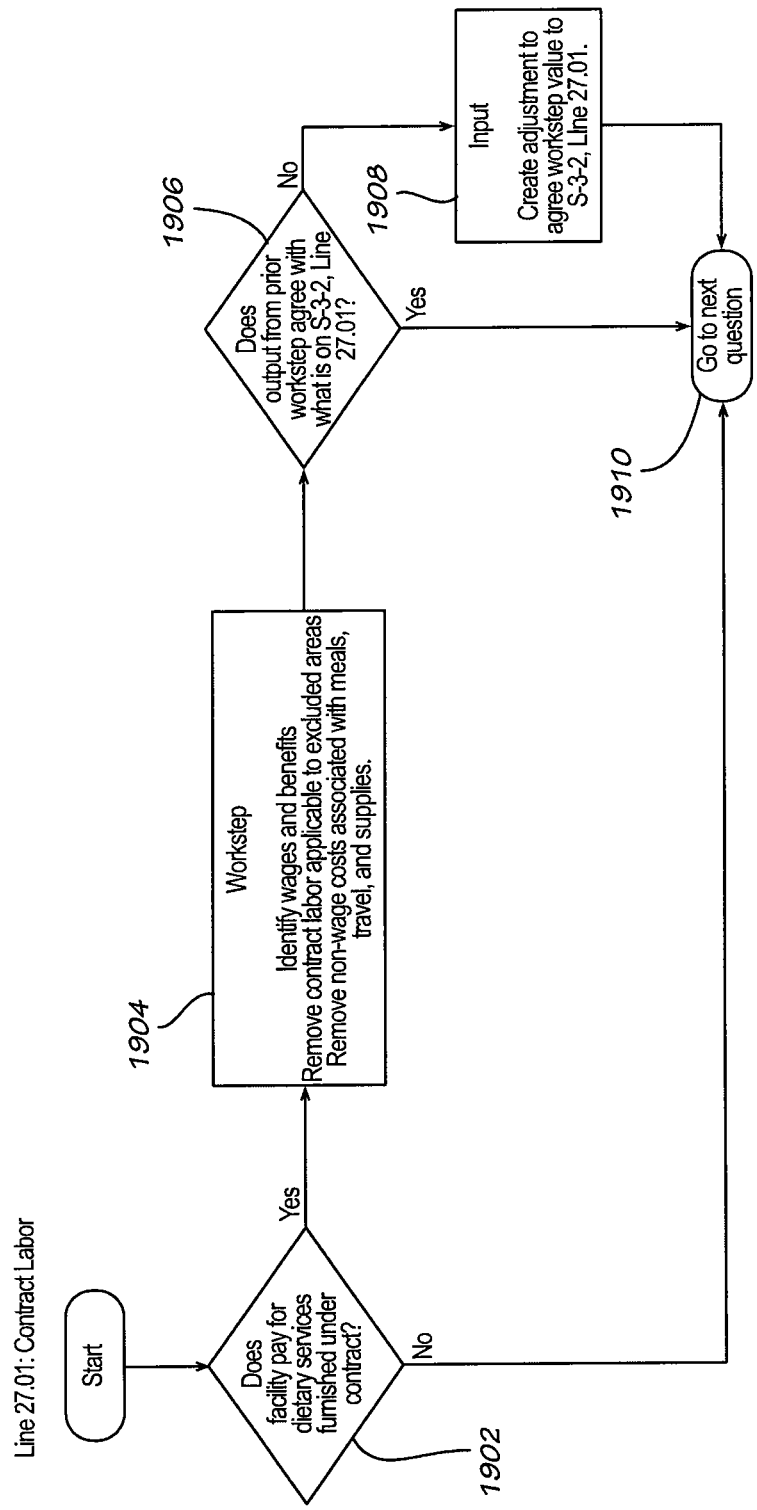
FIG. 19 shows an exemplary processes for computing the contract labor entry for line 27.01.

In FIG. 19, at block 1902, it is determined whether the facility pays for dietary services furnished under contract. If the facility does not pay for such services under contract then control is transferred to block 1910 which proceeds to the next question. If the facility does pay for such services under contract then control is transferred to block 1904.

At block 1904, wages and benefits are identified and the following are removed: contract labor applicable to excluded areas; and non-wage costs associated with meals, travel and supplies. Then at block 1906, it is checked whether the output from block 1904 agrees with what is reported on S-3-2, line 27.01. If it agrees control is transferred to block 1910 which goes to the next question; otherwise control is transferred to block 1908. At block 1908, an adjustment is created to make the value computed in block 1904 agree with what is reported on S-3-2, line 27.01. Then control is transferred to block 1910 which goes to the next question.

Figure 20:
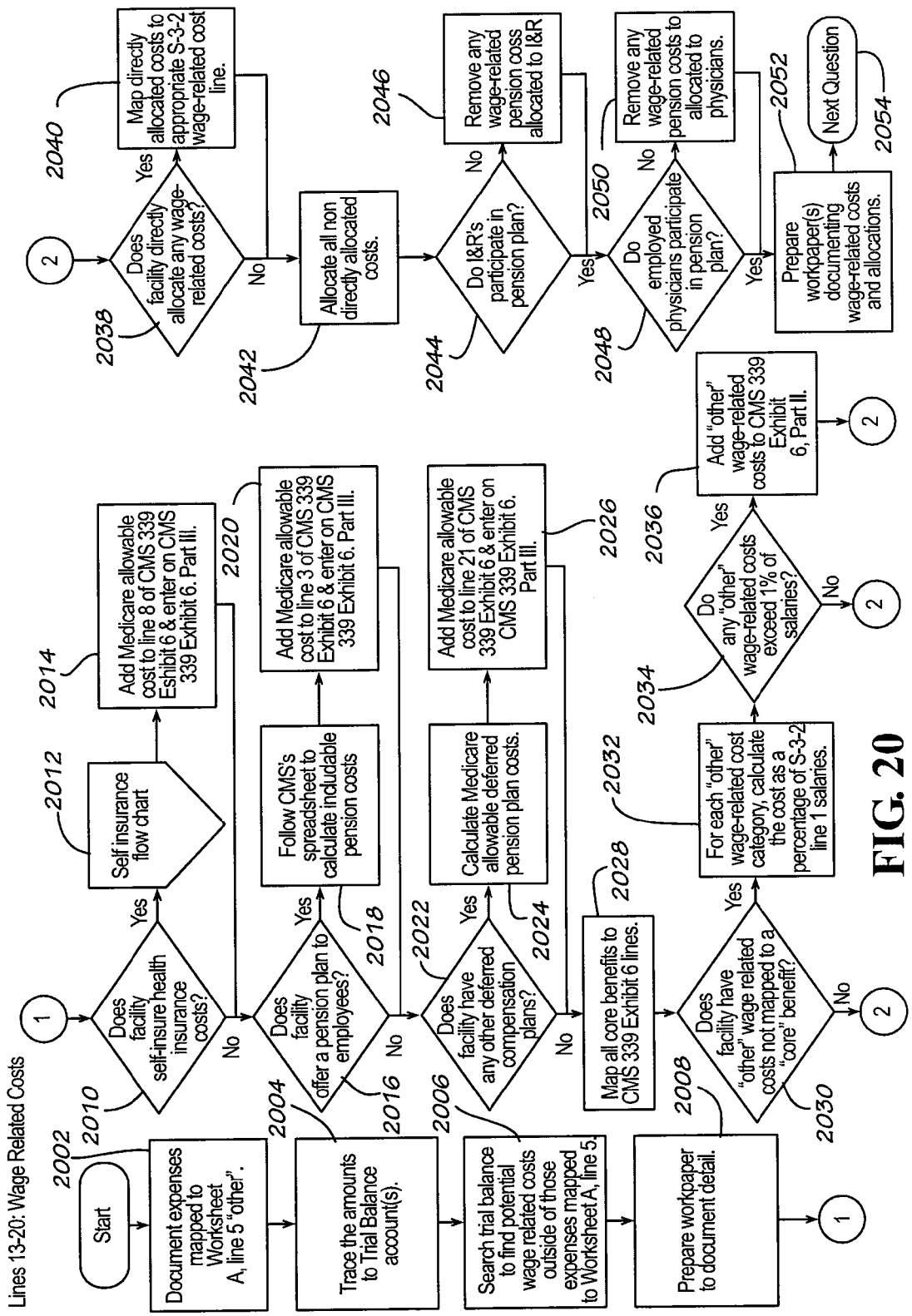
FIG. 20 shows an exemplary process for computing the wage related cost entries for lines 13 to 20.

FIG. 20 shows exemplary data gathering and compilation process 2000 for computing the wage related cost entries for lines 13 to 20. This process also connects with a self insurance process 2100 shown in FIG. 21. Prompts and alerts can be provided to alert the user to various rules regarding the proper entries.

At block 2002, expenses mapped to Worksheet A, line 5, "Other," are documented. Then at block 2004, these amounts on Worksheet A, line 5 are traced to the trial balance account(s). Then at block 2006, the trial balance is searched to find potential wage related costs outside of those expenses mapped to Worksheet A, line 5. Then at block 2008, a workpaper is prepared to document the details for blocks 2002-2006. Then at block 2010, it is determined whether the facility self-insures health insurance costs. If the facility does self-insure health insurance costs control is transferred to block 2012. If the facility does not self-insure health insurance costs control is transferred to block 2016.

At block 2012, control is transferred to the self-insurance process 2100. When control returns, the process continues at block 2014. At block 2014, Medicare allowable costs are added to line 8 of CMS 339 Exhibit 6 and are entered on CMS 339 Exhibit 6, Part III. Then control passes to block 2016.

At block 2016, it is determined whether the facility offers a pension plan to employees. If the facility offers a pension plan control is transferred to block 2018; otherwise control is transferred to block 2022. At block 2018, CMS's spreadsheet is followed to calculate includable pension costs. Then at block 2020, Medicare allowable costs are added to line 3 of CMS 339 Exhibit 6 and are entered on CMS 339 Exhibit 6, Part III. Then control passes to block 2022.

At block 2022, it is determined whether the facility has any other deferred compensation plans. If the facility has other deferred compensation plans control is transferred to block 2024; otherwise control is transferred to block 2028. At block 2024, Medicare allowable deferred pension plan costs are calculated. Then at block 2026, Medicare allowable costs are added to line 21 of CMS 339 Exhibit 6 and are entered on CMS 339 Exhibit 6, Part III. Then control passes to block 2028.

At block 2028, all core benefits are mapped to CMS 339 Exhibit 6 lines. Then at block 2030, it is determined whether the facility has other wage related costs not mapped to a core benefit. If the facility has such other wage related costs control is transferred to block 2032; otherwise control is transferred to block 2038. At block 2032, for each other wage related cost category, the cost is calculated as a percentage of S-3-2, line 1 salaries. Then at block 2034, it is determined whether any other wage related costs exceed 1% of salaries. If none of the other wage related costs exceed 1% of salaries control is transferred to block 2038; otherwise control is transferred to block 2036. At block 2036, other wage related costs are added to CMS 339 Exhibit 6, Part III. Then control passes to block 2038.

At block 2038, it is determined whether the facility directly allocates any wage related costs. If the facility does directly allocate any wage related costs control is transferred to block 2040; otherwise control is transferred to block 2042. At block 2040, directly allocated costs are mapped to appropriate S-3-2 wage related costs lines. Then control passes to block 2042.

At block 2042, all non-directly allocated costs are allocated. Then at block 2044, it is determined whether interns or residents participate in the pension plan. If interns or residents participate in the pension plan control is transferred to block 2048; otherwise control is transferred to block 2046. At block 2046, any wage related pension plan costs allocated to interns and residents are removed. Then control passes to block 2048.

At block 2048, it is determined whether employed physicians participate in the pension plan. If employed physicians participate in the pension plan control is transferred to block 2052; otherwise control is transferred to block 2050. At block 2050, any wage related pension plan costs allocated to physicians are removed. Then control passes to block 2052.

At block 2052, workpaper(s) are prepared to document wage related costs and allocations. Then at block 2054, the system goes to the next question.

Figure 21A:
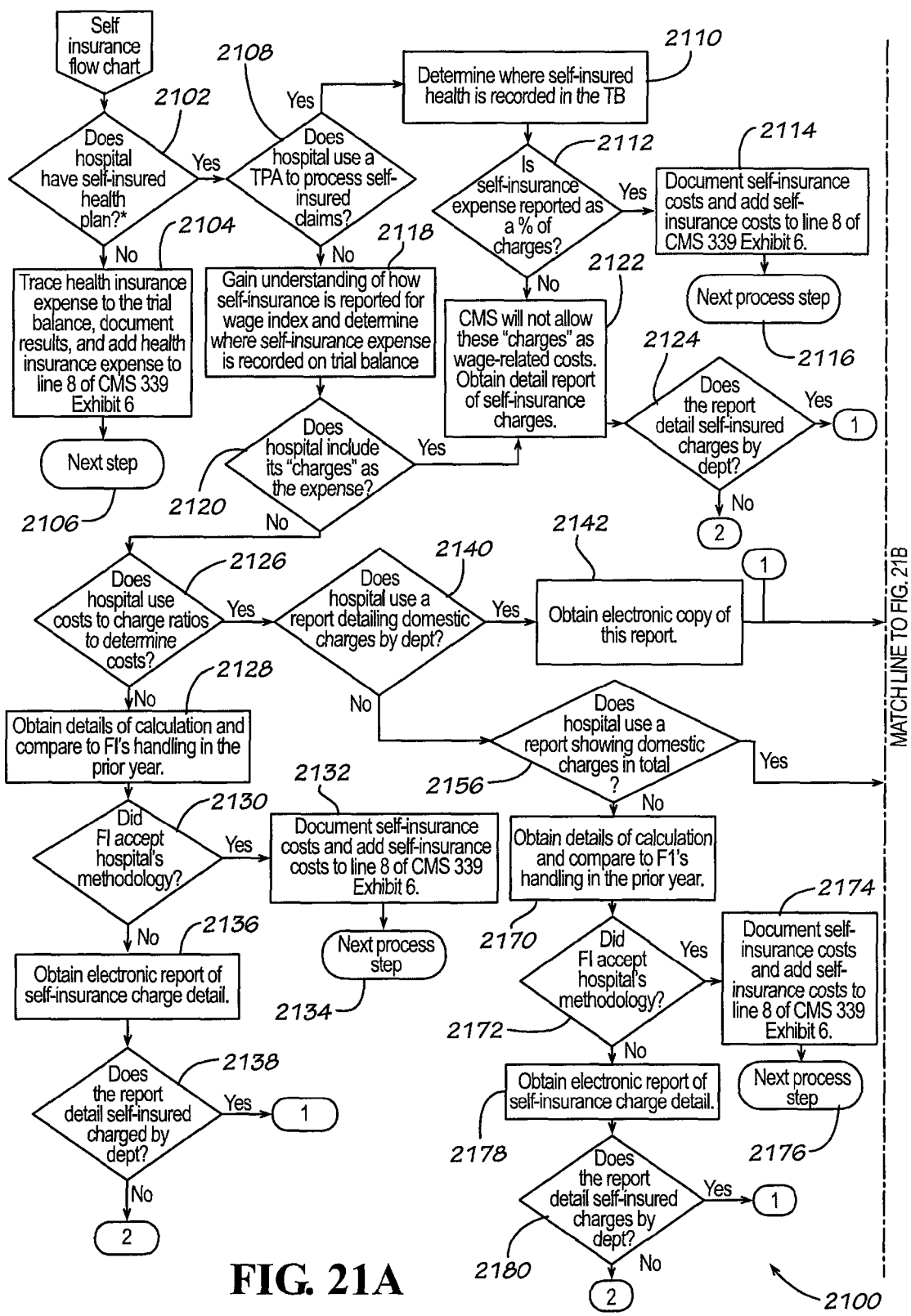
FIG. 21 shows an exemplary process for facility self-insurance wage related cost entries for lines 13 to 20.
Figure 21B:
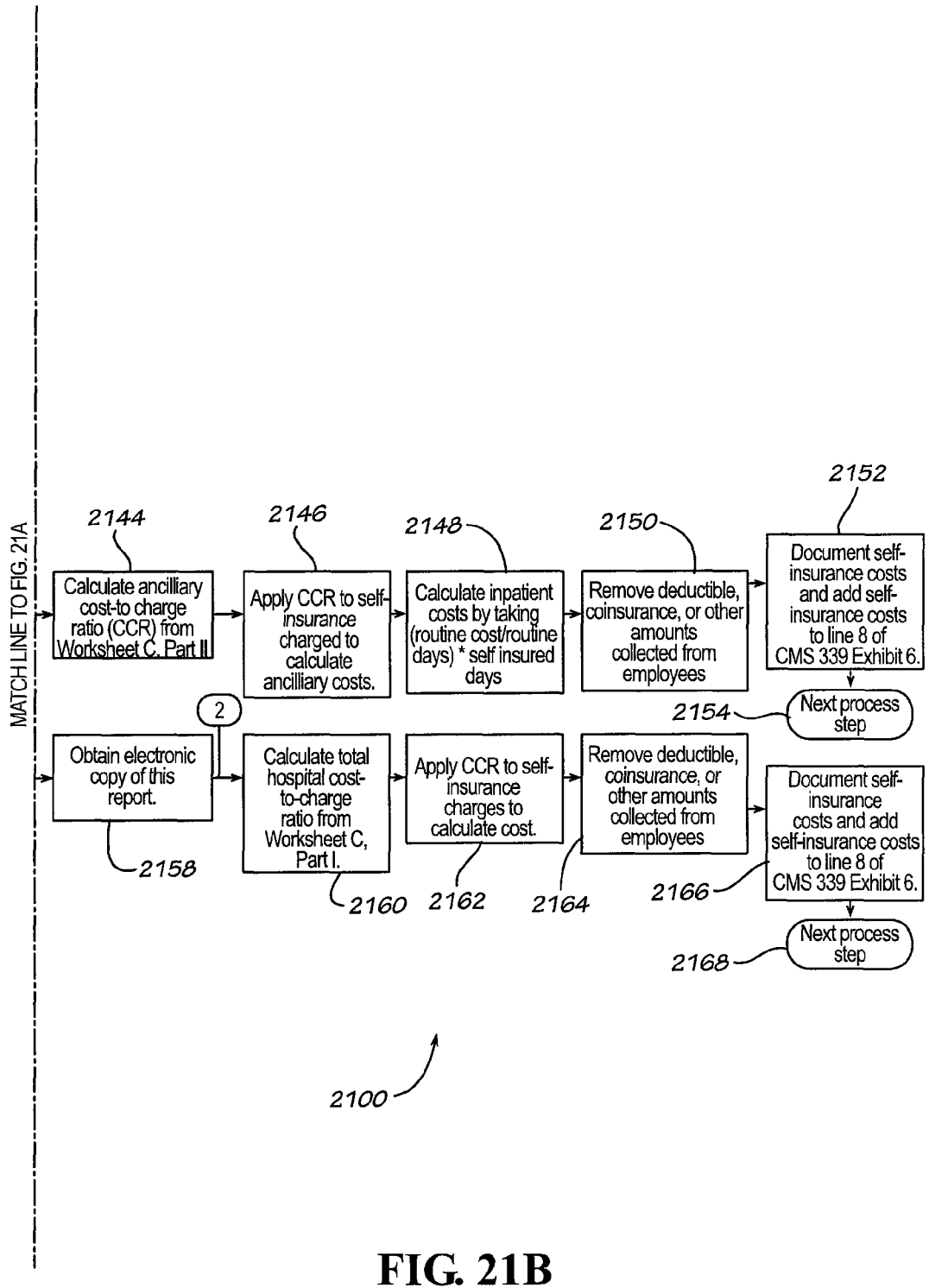

FIG. 21 shows exemplary data gathering and compilation process 2100 for facility self-insurance wage related cost entries for lines 13 to 20. This process 2100 is branched to at block 2102 from the wage related costs process 2000 shown in FIG. 20. Prompts and alerts can be provided to alert the user to various rules regarding the proper entries. If a hospital has self-insured health insurance, in-network claims are often treated differently than out-of-network claims. It will be possible for a user to follow the process 2100 down different paths for each type of claim.

At block 2102, it is determined whether the hospital has a self-insured health plan. If the hospital has a self-insured health plan control is transferred to block 2108. If the hospital does not have a self-insured health plan control is transferred to block 2104. At block 2104, health insurance expenses are traced to the trial balance; results are documented, and health insurance expenses are added to line 8 of CMS 339 Exhibit 6. From block 2104 control is transferred to block 2014 of the wage related costs process 2000 shown in FIG. 20.

At block 2108, it is determined whether the hospital uses a third party administrator to process self-insured claims. If the hospital uses a third party administrator control is transferred to block 2110; otherwise control is transferred to block 2118.

At block 2110, it is determined where self-insured costs are recorded in the trial balance. Then at block 2112, it is determined whether self-insurance expense is reported as a percentage of charges. If self-insurance expense is reported as a percentage of charges control is transferred to block 2114; otherwise control is transferred to block 2122. At block 2114, self-insurance costs are documented and self-insurance costs are added to line 8 of CMS 339 Exhibit 6. Then at block 2116, control is transferred to block 2014 of the wage related costs process 2000 shown in FIG. 20.

At block 2118, it is determined how self-insurance is reported for wage index and where self-insurance expenses are recorded on the trial balance. Then at block 2120, it is determined whether the hospital includes its "charges" as the expense. If the hospital does include its "charges" as the expense control is transferred to block 2122; otherwise control is transferred to block 2126. At block 2122, a prompt warns that CMS will not allow these "charges" as wage-related costs, and a detailed report is obtained of self-insurance charges. Then at block 2124, it is determined whether the report details self-insured charges by department. If the report details self-insured charges by department, control is transferred to block 2144; otherwise control is transferred to block 2160.

At block 2126, it is determined whether the hospital uses cost to charge ratios to determine costs. If the hospital uses cost to charge ratios control is transferred to block 2140; otherwise control is transferred to block 2128.

At block 2128, details of the self-insurance calculation are obtained and are compared to the fiscal intermediary's handling in the prior year. Then at block 2130, it is determined whether the fiscal intermediary accepted the hospital's methodology. If the hospital's methodology was accepted control is transferred to block 2132; otherwise control is transferred to block 2136. At block 2132, self-insurance costs are documented and self-insurance costs are added to CMS 339 Exhibit 6. Then at block 2134, control is transferred to block 2014 of the wage related costs process 2000 shown in FIG. 20.

At block 2136, an electronic report of self-insurance charge details is obtained. Then at block 2138, it is determined whether the report details self-insured charges by department. If the report details self-insured charges by department, control is transferred to block 2144; otherwise control is transferred to block 2160.

At block 2140, it is determined whether the hospital uses a report detailing domestic charges by department. If hospital uses a report detailing domestic charges by department control is transferred to block 2142; otherwise control is transferred to block 2156. At block 2142, an electronic copy of the report detailing domestic charges by department is obtained. Then control passes to block 2144.

At block 2144, ancillary cost-to-charge ratio (CCR) is calculated from Worksheet C, Part II. Then at block 2146, the calculated CCR is applied to self-insurance charges to calculate ancillary costs. Then at block 2148, in-patient costs are calculated by taking (routine cost/routine days)*self-insured days. Then at block 2150, deductibles, coinsurance and other amounts collected from employees is removed. Then at block 2152, self-insurance costs are documented and self-insurance costs are added to line 8 of CMS 339 Exhibit 6. Then at block 2154, control is transferred to block 2014 of the wage related costs process 2000 shown in FIG. 20.

At block 2156, it is determined whether the hospital uses a report showing domestic charges in total. If the hospital uses a report showing domestic charges in total control is transferred to block 2158; otherwise control is transferred to block 2170. At block 2158, an electronic copy of the report showing domestic charges in total is obtained. Then control is transferred to block 2160.

At block 2160, total hospital cost-to-charge ratio (CCR) is calculated from Worksheet C, Part I. Then at block 2162, the calculated CCR is applied to self-insurance charges to calculate cost. Then at block 2164, deductibles, coinsurance and other amounts collected from employees are removed. Then at block 2166, self-insurance costs are documented and self-insurance costs are added to line 8 of CMS 339 Exhibit 6. Then at block 2168, control is transferred to block 2014 of the wage related costs process 2000 shown in FIG. 20.

At block 2170, total hospital cost-to-charge ratio (CCR) is calculated from Worksheet C, Part I. Then at block 2162, the calculated CCR is applied to self-insurance charges to calculate cost. Then at block 2164, deductibles, coinsurance and other amounts collected from employees are removed. Then at block 2166, self-insurance costs are documented and self-insurance costs are added to line 8 of CMS 339 Exhibit 6. Then at block 2168, control is transferred to block 2014 of the wage related costs process 2000 shown in FIG. 20.

At block 2170, details of the report and calculations showing domestic charges in total are obtained and are compared to the fiscal intermediary's handling in the prior year. Then at block 2172, it is determined whether the fiscal intermediary accepted the hospital's methodology. If the hospital's methodology was accepted control is transferred to block 2174; otherwise control is transferred to block 2178. At block 2174, self-insurance costs are documented and self-insurance costs are added to CMS 339 Exhibit 6. Then at block 2176, control is transferred to block 2014 of the wage related costs process 2000 shown in FIG. 20.

At block 2178, an electronic report of self-insurance charge details is obtained. Then at block 2180, it is determined whether the report details self-insured charges by department. If the report details self-insured charges by department, control is transferred to block 2144; otherwise control is transferred to block 2160.

Figure 22:
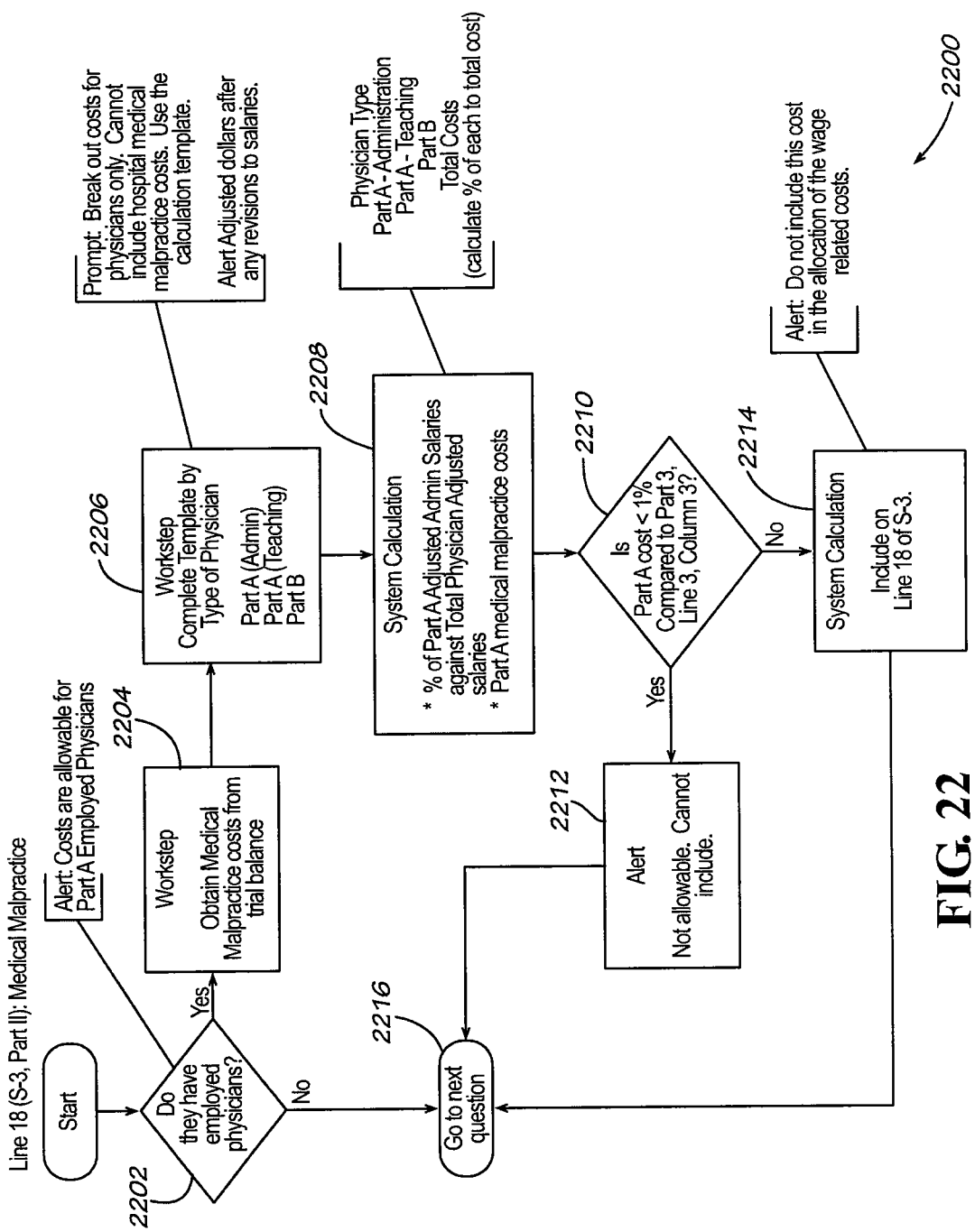
FIG. 22 shows an exemplary process for computing the medical malpractice entry for line 18.

FIG. 22 shows an exemplary data gathering and compilation process 2200 for computing the medical malpractice entry for line 18. This process calculates the medical malpractice amount. The data sources for this process include user input and calculated values as well as the S-3. Prompts and alerts can be provided to alert the user to various rules regarding the proper entries.

At block 2202, it is determined whether the facility has employed physicians. Block 2202 can include an alert that costs are allowable for Part A employed physicians. If the facility has employed physicians control is transferred to block 2204, otherwise control is transferred to block 2216. At block 2204, medical malpractice costs are obtained from the trial balance. Then at block 2206, a template can be provided for the user to complete by type of physician which breaks out: Part A (Admin), Part A (Teaching) and Part B. Block 2206 can include a prompt to break out costs for physicians only and not to include hospital medical malpractice costs. Block 2206 can also include an alert to use adjusted dollars after any revisions to salaries. Then at block 2208, a calculation is made of percentage of Part A adjusted admin salaries against total physician adjusted salaries, and a calculation of Part A medical malpractice costs. Block 2208 also calculates the percentage of each of Part A (Admin), Part A (Teaching) and Part B to total costs. Then at block 2210, it is checked whether Part A costs less than one percent compared to Part 3, line 3, column 3. If Part A costs are less than one percent control is transferred to block 2212; otherwise control is transferred to block 2214. At block 2212, an alert is provided that the costs are not allowable and cannot be included. At block 2214, medical malpractice costs are included on line 18 of S-3. Block 2214 can also include an alert to not include this cost in the allocation of the wage related costs. From either block 2212 or 2214 control passes to block 2216.

At block 2216, the system goes on to the next question.

Figure 23A:
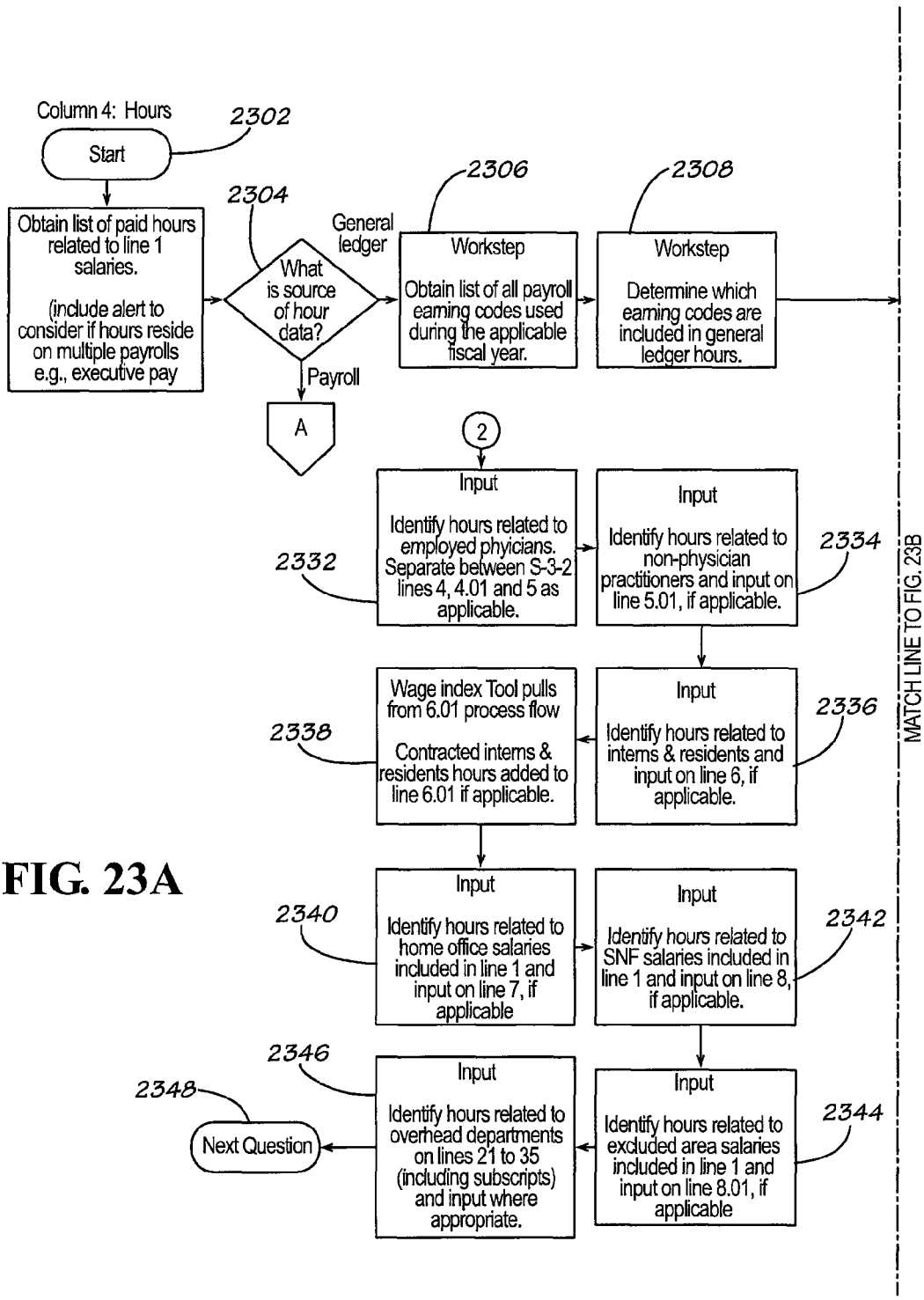
FIGS. 23 and 24 show an exemplary processes for computing the hours entry for column 4.
Figure 23B:
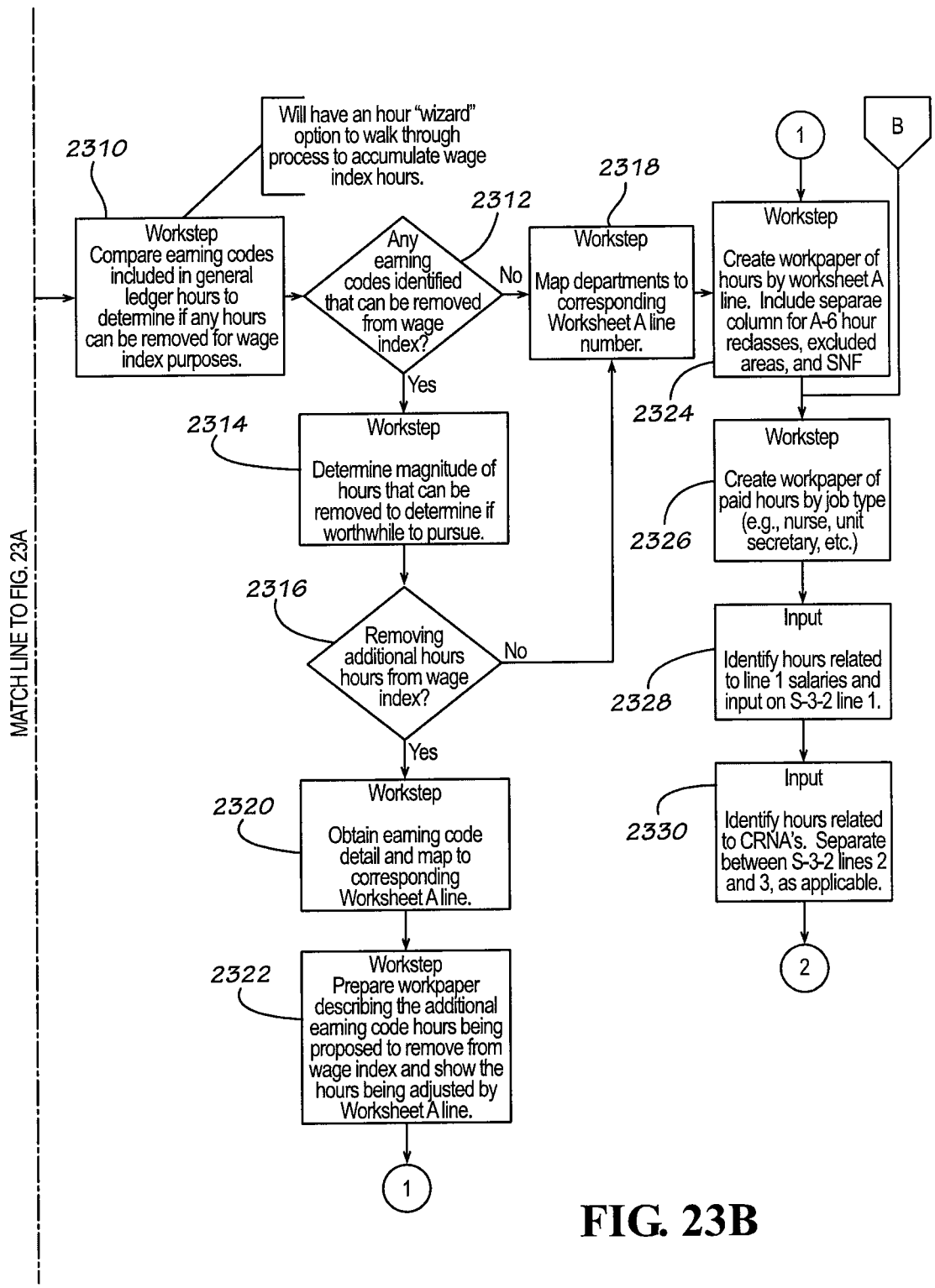
Figure 24:
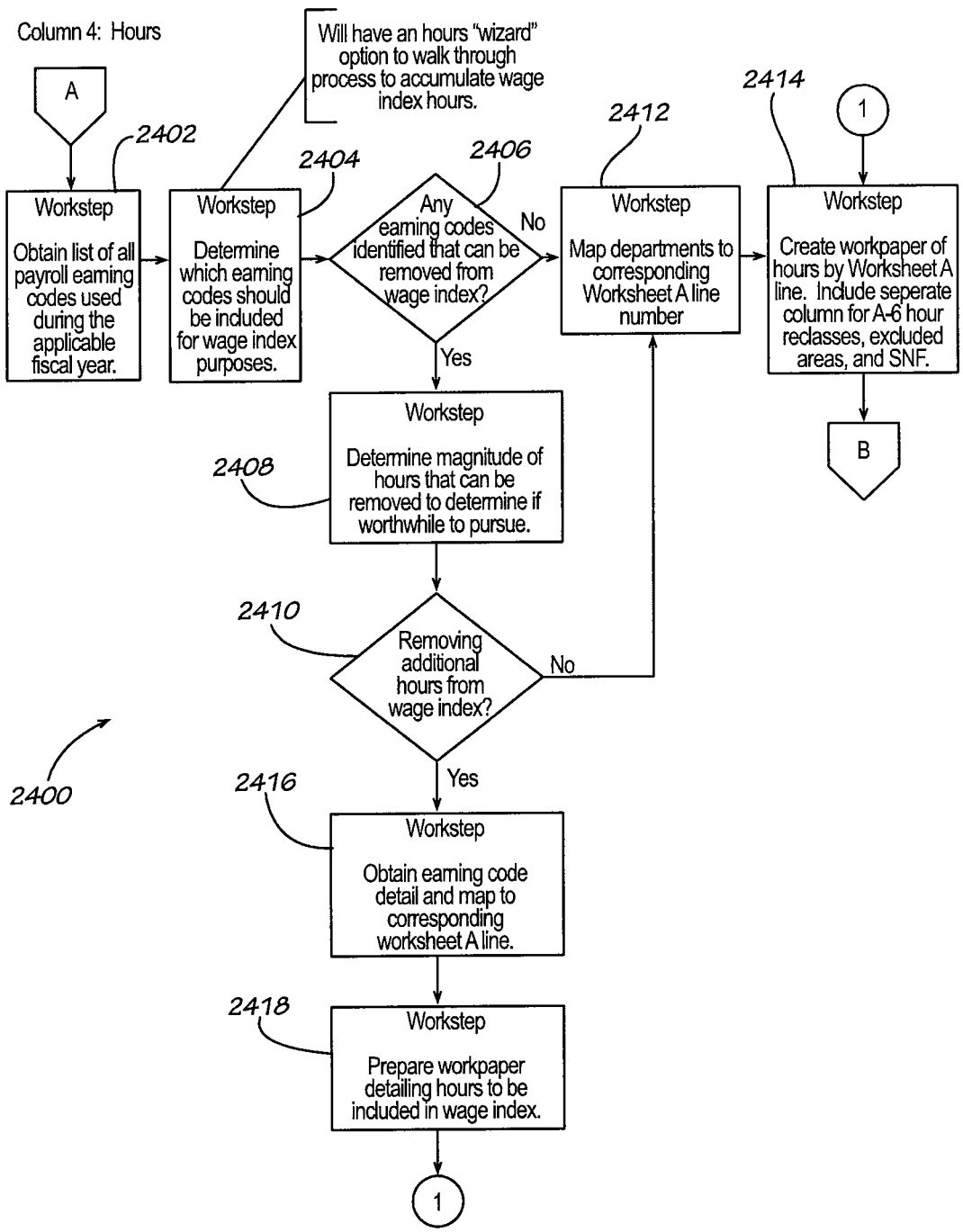

FIGS. 23 and 24 show exemplary data gathering and compilation processes 2300 and 2400, respectively, for computing the hours entry for column 4. Prompts and alerts can be provided to alert the user to various rules regarding the proper entries.

At block 2302, a list of paid hours related to line 1 salaries is obtained. An alert is also included to alert the user to consider if hours reside on multiple payrolls (e.g., executive pay). Then at block 2304, it is determined what the source of the hour data is. If the hour data comes from payroll control is transferred to block 2402 of the hours process 2400 shown in FIG. 24. If the hour data comes from the general ledger control is transferred to block 2306.

At block 2306, a list of all payroll earning codes used during the applicable fiscal year is obtained. Then at block 2308, it is determined which earning codes are included in general ledger hours. Then at block 2310, earning codes are included in the general ledger hours are compared to determine if any hours can be removed for wage index purposes. Block 2310 can include an hour wizard to walk the user through the process of accumulating wage index hours. At block 2312, it is checked whether any earning codes are identified that can be removed from wage hours. If any earning codes can be removed control is transferred to block 2314; otherwise control is transferred to block 2318. At block 2314, the magnitude of hours that can be removed is determined to determine if it is worthwhile to pursue. Then at block 2316, it is determined whether additional hours are to be removed from the wage index. If additional hours are to be removed control is transferred to block 2320; otherwise control is transferred to block 2318.

At block 2318, departments are mapped to corresponding Worksheet A line numbers. Then control is transferred to block 2324.

At block 2320, earning code details are obtained and are mapped to corresponding Worksheet A lines. Then at block 2322, a workpaper is prepared describing the additional earning code hours being proposed to remove from wage index, and showing the hours being adjusted by Worksheet A line. Then control is transferred to block 2324.

At block 2324, a workpaper is created of hours by Worksheet A line including separate column for A-6 hour reclasses, excluded areas and SNF.

At block 2326, a workpaper is created of paid hours by job type (e.g., nurse, unit secretary, etc.). Then at block 2328, hours related to line 1 salaries are identified and input on S-3-2, line 1. Then at block 2330, hours related to non-physician anesthetists are identified and separated between S-3-2, lines 2 and 3, as applicable. Then at block 2332, hours related to employed physicians are identified and separated between S-3-2, lines 4, 4.01 and 5, as applicable. Then at block 2334, hours related to non-physician practitioners and input on line 5.01, if applicable. Then at block 2336, hours related to interns and residents are identified and input on line 6, if applicable. Then at block 2338, the system pulls from 6.01 process flow and contracted intern and resident hours are added to line 6.01, if applicable. Then at block 2340, hours related to home office salaries included in line 1 are identified and input on line 7, if applicable. Then at block 2342, hours related to skilled nursing facility (SNF) salaries included in line 1 are identified and input on line 8, if applicable. Then at block 2344, hours related to excluded area salaries included in line 1 are identified and input on line 8.01, if applicable. Then at block 2346, hours related to overhead departments on lines 21 to 35 (including subscripts) are identified and input where appropriate. Then at block 2348, the system goes to the next question.

At block 2402 of process 2400, a list of all payroll earning codes used during the applicable fiscal year is obtained. Then at block 2404, it is determined which earning codes should be included for wage index purposes. Block 2404 can include an hour wizard option to walk the user through the process of accumulating wage index hours. Then at block 2406, it is checked whether any earning codes are identified that can be removed from wage hours. If any earning codes can be removed control is transferred to block 2408; otherwise control is transferred to block 2412. At block 2408, the magnitude of hours that can be removed is determined to determine if it is worthwhile to pursue. Then at block 2410, it is determined whether additional hours are to be removed from the wage index. If additional hours are to be removed control is transferred to block 2416; otherwise control is transferred to block 2412.

At block 2412, departments are mapped to corresponding Worksheet A line numbers. Then control is transferred to block 2414.

At block 2416, earning code details are obtained and are mapped to corresponding Worksheet A lines. Then at block 2418, a workpaper is prepared detailing hours to be included in wage index. Then control is transferred to block 2414.

At block 2414, a workpaper is created of hours by Worksheet A line including separate column for A-6 hour reclasses, excluded areas and SNF. Then control is transferred to block 2326 of process 2300 shown in FIG. 23.

In addition to all of the processes and functionality disclosed above, the wage index navigator system can generate various reports to assist users in the wage index review processes. Analysis reports are made up of lookup and calculation values pulled together in a tabular format to allow the recipient to make subjective review of the data and information provided for decision making or other purposes.

Dashboard reports are intended to provide high level visibility and insight into current activity, progress, and current results. The system can provide an authorized user with an Activity Dashboard that shows a hospital system, hospital or staff member progress towards completion of the wage index review process. The system can provide an authorized user with the ability to view the data entered and attached work papers of a particular assigned hospital system or hospital. The system can also display a countdown reminder of days left until deadline to users that have not yet completed the wage index review for the current year.

An impact sheet summary can be generated to display the impact across the Core Based Statistical Area (CBSA) based on proposed changes. The impact sheet can calculate the as-filed average hourly wage based upon the data from the PUF. These values are the basis from which changes are measured. The tool can calculate an estimated impact to the overall average hourly wage based on changes made to either salaries or hours through the wage index navigator system. The impact sheet summary report can have parameters to select the desired CBSA and year. The impact sheet summary can include the following fields:

Hospital name
Geographic CBSA
Salary—Overall (line 1, 21-35)
Salary—CRNA (lines 2 & 3)
Salary—Physicians (lines 4, 4.01, 5, 5.01, 10, 10.01)
Salary—Interns & Residents (lines 6)
Salary—Home office (lines 7, 11, 12, 12.01)
Salary—Excluded areas (lines 8, 8.01)
Salary—Contract labor (lines 6.01, 9, 9.01, 9.02)
Salary—Wage-related costs (lines 13-20)
Hours—All (except lines 13-20)

An exemplary impact sheet summary (without data) is shown in FIG. 25.

An impact sheet can be generated by the wage index navigator system to show the change in a hospital's overall average hourly wage based on proposed changes. The impact sheet can show the as-filed average hourly wage based upon the data from the PUF. These values are the basis from which changes are measured. The wage index navigator system can calculate and show on an impact sheet an estimated impact to the overall average hourly wage based on changes made to either salaries or hours through the system. Impacts can be calculated based on any of the following defined groupings where each grouping can represent a separate impact report:

Salaries:
Overall (line 1, 21-35)
CRNA (lines 2 & 3)
Physicians (lines 4, 4.01, 5, 5.01, 10, 10.01)
Interns & Residents (lines 6)
Home office (lines 7, 11, 12, 12.01)
Excluded areas (lines 8, 8.01)
Contract labor (lines 6.01, 9, 9.01, 9.02)
Wage-related costs (lines 13-20)
Hours:
All (except lines 13-20)
Salaries and Hours:
Overhead departments (lines 21-35)

If there are no adjustments for a particular grouping then the report can be skipped for that grouping. The proposed adjustment listing can be produced on demand. Impact sheets are not intended be included in the process outcome reports sent to the fiscal intermediary. The impact sheets can be configured to mirror S-3, Part II & III. An exemplary impact sheet is shown in FIG. 26.

A Proposed Adjustment Listing can be generated by the wage index navigator system to capture the difference between what is included in a hospital's as-filed Worksheet S-3 wage data and what is requested to be revised. The Proposed Adjustment Listing can be the package that is assembled to send to the fiscal intermediary. The Proposed Adjustment Listing can be used to determine what happens with all of the data that is captured and how it is reported to the fiscal intermediary. The wage index navigator system can initially display data pulled from the preliminary PUF unless data was manually entered by the user beforehand. The user has the option to adjust the data contained within the PUF as they complete the wage index review. The adjustments will automatically be captured to populate a proposed adjustment list. The reference number, line description, line number, and column numbers will all be predefined based on the adjustment(s) being made. The proposed adjustment listing can be configured so that only line(s) with positive or negative adjustments will be displayed in the proposed adjustment listing. The proposed adjustment listing can be produced on demand as well as included in the process outcome produced for the fiscal intermediary. The proposed adjustment listing can be configured to have the following fields:

Reference number
S-3, Part II Line Description
S-3, Part II Line Number
S-3, Part II Column Number
As-Filed Amount
Proposed Amount
Adjustment Total The system can support the ability for a user to generate an electronic data file that contains the wage index data in a desired format, such as a PDF format. The data file can be comprised of a cover letter, proposed adjustment listing, and supporting documentation. The system provides an interface that allows an authorized user to select which workpaper attachments are to be included in the data file. The system allows an authorized user to download the electronic data file to send to the fiscal intermediary. An authorized user can generate a copy of wage index process output in order to print a hard copy and mail it to the fiscal intermediary on behalf of the hospital. An authorized user can select the CBSA and choose the hospitals, and then the system will produce all of the contents for the electronic data file for the desired hospitals. An authorized user can then download and/or print the electronic data file. The wage index review process should be complete and finalized before the process outcome is produced.

The system enables an authorized user to download a template letter for the hospital or health system to customize for sending to the fiscal intermediary. The user can customize the template as desired and then upload a completed copy of the letter for later use. The electronic data file produced may be too large for certain email systems to accept it as an attachment. The system provides the ability for the user to control how the electronic data file will be broken up in to multiple files, for example by selecting how many documents will be produced and selecting the ending page for each document. The defined functionality above can be configured such that it only displays rows when the "Adjustment Total" value is not equal to zero. An exemplary portion of a proposed adjustment listing is shown in FIG. 27.

The wage index navigator system can also allow an authorized user to view a copy of an S-3, Parts II & III as entered. The system will allow the authorized user to view a report that displays the as-filed, proposed, or post desk review S-3 data as entered for a specific provider in a specific year. The report can match the standard display format commonly used for the S-3 which includes columns for:

Line Number
Description
Amount Report (Column 1)
Reclass of Salaries (Column 2)
Adjusted Salaries (Column 3)
Paid Hours Related to Salary (Column 4)
Average Hourly Wage (Column 5)

An exemplary S-3 display is shown in FIG. 28.

The wage index navigator system can also generate a county reclassification summary report that displays the financial impact within a CBSA of county reclassifications for a given fiscal year. The system will provide a report that allows an authorized user to see the financial impact of reclassifications within a particular CBSA within a given fiscal year. The report can include the following columns grouped by inpatient and outpatient for each hospital:

Hospital
Wage index without reclassification
Wage index with reclassification
Gain and the report can include the following summaries at the bottom:

Total inpatient impact
Total outpatient impact
Grand total.

An exemplary county reclassification summary report is shown in FIG. 29.

The wage index navigator system can also generate an estimated wage index values report that targets the CBSA level and projects the wage index for the in process fiscal year using the best available data. The system provides reporting functionality that allows an authorized user to run a report that shows the estimated wage index value for the federal fiscal year currently being reviewed using the best available data.

Figure 30:
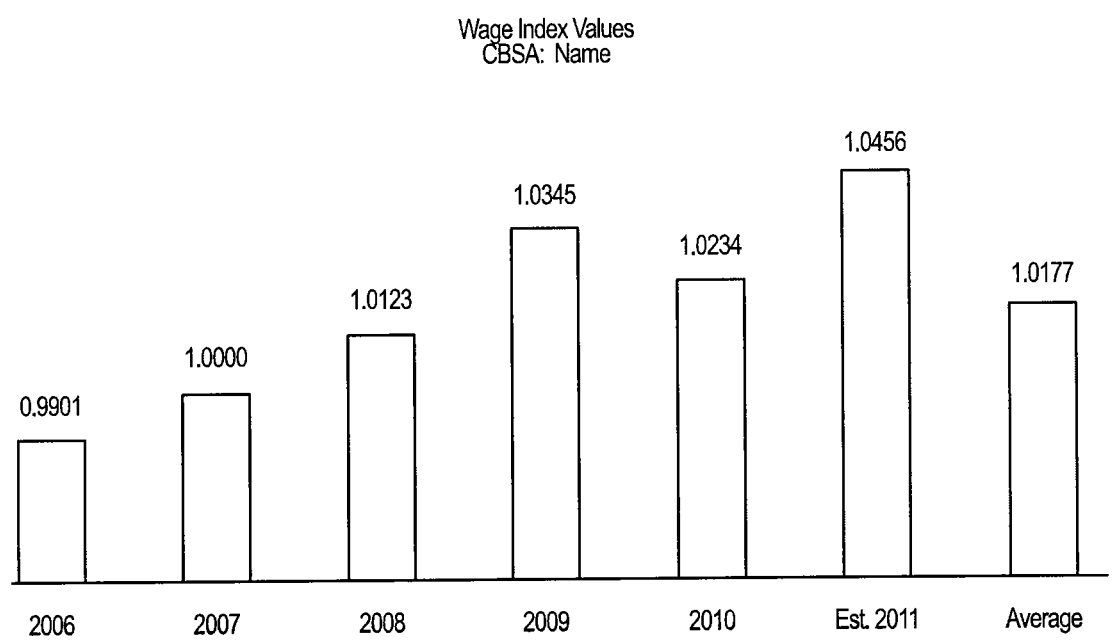
FIG. 30 shows an exemplary estimated wage index values report.

The Estimated Wage Index Calculation is available after the February PUF has been imported. After publication of the final PUF for a Federal fiscal year, this report can be considered the wage index value report which is no longer a projection but rather the actual (e.g., actual data trumps estimated values). The report displays the estimated wage index ratio for the current year and the wage index ratio for the four previous years. The report can produce as a single row where the columns contain the estimated followed by the actual wage index factor values. The report contains the following columns:
  CBSA
  Current Year Calculated value
  Prior year #1 actual
  Prior year #2 actual
  Prior year #3 actual
  Prior year #4 actual
An exemplary estimated wage index values report is shown in FIG. 30.

The wage index navigator system can also generate an estimated impact report for a CBSA that projects the financial impact of the estimated changes using the best available data. The estimated impact report contains an estimation of the average hourly wage and overall estimated reimbursement impact for a chosen CBSA by hospital. The system provides the ability for an authorized user to view adjustments initiated by the fiscal intermediary by comparing the as-reported data to the Revised S-3. The estimated impact report includes parameters for CBSA and year. The estimated impact for a hospital can include the following columns:
  Provider Name
  AHW Per Prior Year Final Rule
  Percent of CBSA Per Prior Year Final Rule
  Negative WI Adjustments
  Negative Impact on CBSA
  Negative WI Impact on Reimbursement
  Positive WI Adjustments
  Positive Impact on CBSA
  Positive WI Impact on Reimbursement
  Total Estimated WI Review AHW Impact
  Impact to CBSA AWI
  Current Reimbursement Impact (Reviewed Hosp Impact Only—Incr. of $0.06)
  Current Reimbursement Impact (Incr. of $0.06)
A portion of an exemplary estimated impact report for a CBSA is shown in FIG. 31.

Figure 32:
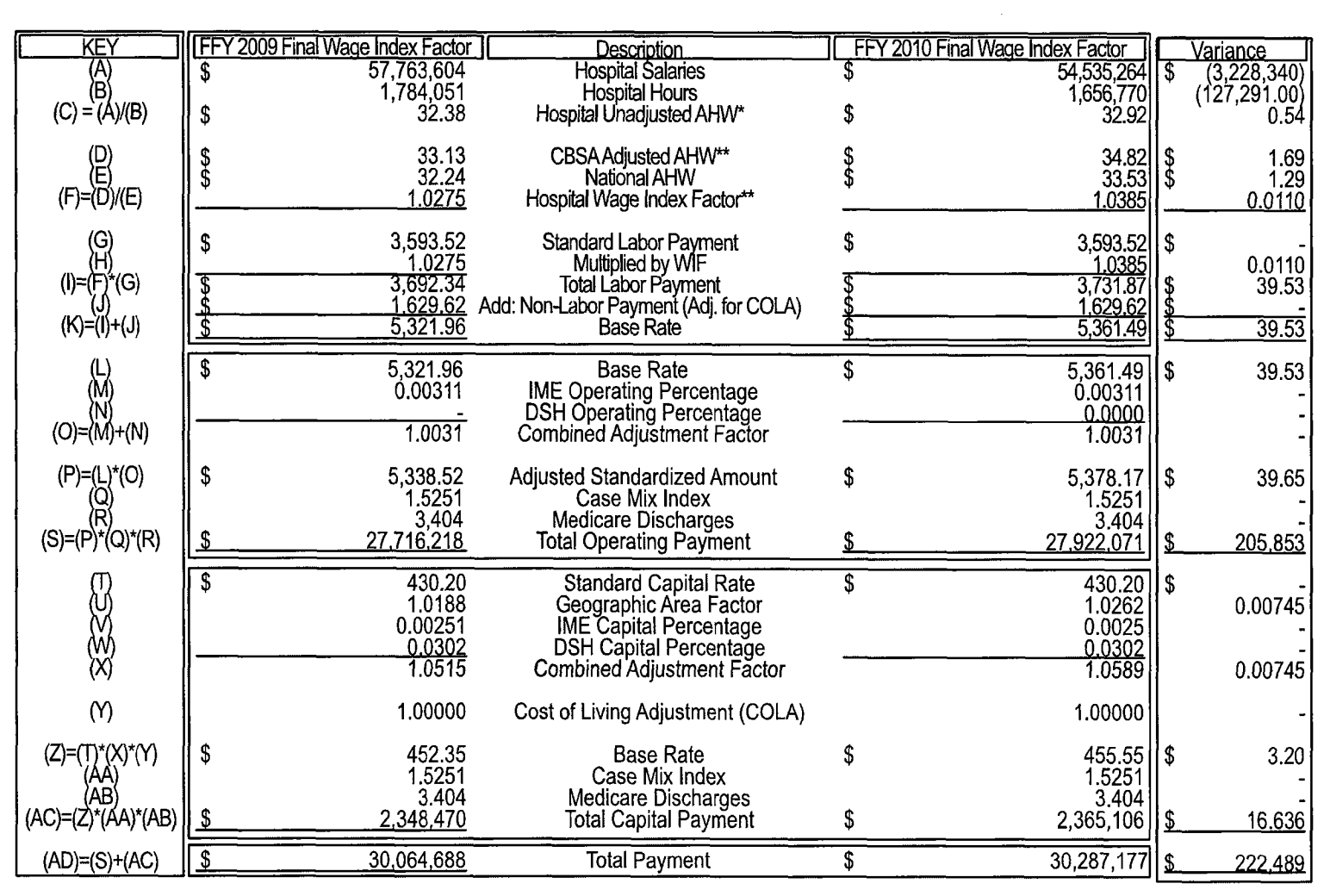

The wage index navigator system can also generate an estimated impact report for a hospital that projects the financial impact of the estimated changes using the best available data. The report uses a specific provider number off which to base the report data. The user selects a CBSA and a specific hospital within the CBSA. The estimated impact report can include a heading with the following values:
  Provider Name
  Report Name
  Provider Number
  CBSA number
and the following columns:
  Key
  Prior Fiscal Year Final Wage Index Factor
  Description
  Current Fiscal Year Final Wage Index Factor
  Variance (Current−Prior)
An exemplary estimated impact report for a hospital is shown in FIG. 32.

The wage index navigator system can also generate "What-if" impact scenarios for a CBSA. For budgeting/planning purposes hospitals have a desire to know a best guess of the estimated reimbursement impact using data available at the time. The system supports the ability for an authorized user to estimate "what-if" scenarios for a CBSA for a specified fiscal year by entering an assumed change to an individual hospital's average hourly wage (AHW), or to a CBSA's overall AHW. The system enables the user to make successive changes to the individual hospital's or CBSA's AHW. The system performs successive calculations of the current model until the user chooses to reset the values and start again. The display can include the following items based on the selected fiscal year and CBSA:
  Current AHW
  Current National AHW
  Current Wage Index Factor (WIF)
  Total AHW Increase
  Total Impact
The what-if scenario can display the following fields for each hospital (It is noted whether the field is a lookup or is part of the calculation.):
  Provider number (lookup)
  Provider name (lookup)
  Geographic CBSA (lookup)
  Post-Reclass CBSA (lookup)
  Percent CBSA (calculated)
  Increase Average Hourly Wage (post-calculation)
  Weighted Increase (post-calculation)
  Impact (post-calculation)
  Provider Wages (lookup)
  Discharges (lookup)
  Medicare Cases (lookup)
  AHW (lookup)
  CMI (lookup)
  Original WIF (lookup)
  Original Blended Rate (lookup)
  New Blended Rate (post-calculation)
  Original Payment (lookup)
  New Payment (post-calculation)
  Benefit Percent (calculated based on initial or revised S-3)
  Difference between original and new value
The system can sort the display by clicking on a particular column heading in the results display. The what-if scenario can be based upon data imported from the PUF, Final Rule Standardizing, Final Review and Correction Notice, Final Corrected Rates, and/or Final Corrected Tables data files from CMS. The system enables an authorized user to save what-if scenario values in order to support complex scenarios that require long running manipulation of values. The user can save and delete each scenario. The scenarios can be protected to only be viewable to the creating user. An exemplary what-if impact scenario report is shown in FIG. 33.

The wage index navigator system can also generate a CBSA overview report that contains a combination of lookup and calculated values to display hospital specific data for a CBSA. The CBSA overview report is based upon data from the PUF and Federal Register data files. The user chooses a fiscal year and desired CBSA for which they would like to view overview information. The report detail display can have a layout similar to the what-if scenarios display. The report can include the following columns for each hospital in a given CBSA in a given year:
  Provider Number
  Provider Name
  Geographic CBSA Number
  Salaries (lookup)
  Benefits (lookup)
  Salaries plus Benefits (calculated)

Hours (lookup)
Benefit Percent (calculated)
AHW (lookup)

An exemplary CBSA overview report is shown in FIG. 34.

The wage index navigator system can also generate exception monitoring reports. Exception monitoring reports involve comparisons of the revised S-3 or various PUF data to seek discrepancies. The revised S-3 provided in hardcopy by the fiscal intermediary can be keyed in to the system. It can then be used in comparison to other data to monitor for exceptions to expected values. A discrepancy report can compare various data points and an alert can be generated if there is a discrepancy between the data points. Alerts can trigger an email to involved hospitals notifying them that an exception has been found and directing them to a view of the S-3, where the differences are highlighted. When alerts are triggered, designated users will receive a summary email with a list of all members that have discrepancies.

A discrepancy report can be generated to compare the October PUF for the current year to the Final PUF from the prior year. An alert is generated if there is a discrepancy between them that exceeds user defined dollar or percentage variance thresholds. Additionally, an alert is generated if there are values that are identical, as the values are all expected to change in some degree.

A discrepancy report can be generated to compare the S-3 resulting from the fiscal intermediary desk review and the submitted proposed adjustments. An alert is generated if there is a discrepancy between them. Note that there are not expected to be discrepancies, so the system will call attention to any discrepancy.

A discrepancy report can be generated to compare the S-3 resulting from the fiscal intermediary desk review and the February PUF. An alert is generated if there is a discrepancy between them. Note that there are not expected to be discrepancies, so the system will call attention to any discrepancy.

A discrepancy report can be generated to compare the Revised S-3 from the fiscal intermediary desk review to the PUF file released in May. An alert is generated if there is a discrepancy between them.

A discrepancy report can be generated to compare the Revised S-3 from the fiscal intermediary desk review to the final PUF file released in August. An alert will be generated if there is a discrepancy between them.

A discrepancy report can be generated to compare the Revised S-3 from the May PUF to the final PUF file released in August. An alert will be generated if there is a discrepancy between them.

The wage index navigator system can also generate comparison reports. Comparison reports offer the ability to compare values involved in the report.

The wage index navigator system can generate a summary PUF comparison report for a CBSA. An authorized user can choose from the following parameters to compare summary PUF data for a Geographic CBSA:
  Urban/Rural
  Geographic CBSA
  Year
  Current year only, or include up to four years of historical data as well The report can include rows of data based upon the CBSA, national average, year, and historical years. The report can include the source notes included in the PUF data. The report can also include the following columns:
  CBSA AHW or National AHW label
  Initial PUF AHW
  Initial PUF Number of Hospitals
  Final PUF AHW
  Final PUF Number of Hospitals
  AHW Dollar Variance
  AHW Percent Variance
  Number of Hospitals Variance An exemplary summary PUF comparison report for a CBSA is shown in FIG. 35.

The wage index navigator system can generate a PUF comparison report for a CBSA. An authorized user can select whether the report should be produced for a CBSA or for a specific hospital within the CBSA. The report will default to the user's hospital if the user is assigned to a particular hospital. The remaining features in this section assume the report type chosen is for a CBSA. The user can choose from the following parameters to compare PUF data for a CBSA:
  CBSA
  Year
  PUF #1: Prior Year Final, Initial, February, May, August
  PUF #2: Prior Year Final, Initial, February, May, August
  Current year only, or include four years of historical data as well The report has rows based on each hospital within the CBSA. The report adjusts the PUF #1 and PUF #2 options available for selection based upon the PUF data that has been loaded for the given year. The report can include the following columns:
  Provider Number
  Hospital Name
  CBSA Number
  Service Type (indicator if it was completed by the tool)
  CBSA Percent
  PUF #1 AHW
  PUF #2 AHW
  Nominal Change in AHW
  Percent Change in AHW An exemplary PUF comparison report for a CBSA is shown in FIG. 36.

The wage index navigator system can generate a PUF comparison report for a hospital. An authorized user can select whether the report should be produced for a CBSA or for a specific hospital within the CBSA. The report will default to the user's hospital if the user is assigned to a particular hospital. The remaining features in this section assume the report type chosen is for a hospital. The user can choose from the following parameters to compare PUF data for a hospital:
  Year
  PUF #1: Prior Year Final, Initial, February, May, August
  PUF #2: Prior Year Final, Initial, February, May, August
  Current year only, or include four years of historical data as well The report has row values based on PUF line number values. The comparison report has the following columns for each PUF in the report:
  Adjusted Salaries
  Paid Hours Related to Salary in Col. 3
  (Col 3/Col 4) Average Hourly Wage An exemplary PUF comparison report for a hospital is shown in FIG. 37.

The wage index navigator system can generate a CBSA comparison report. The CBSA comparison report enables an authorized user to compare their CBSA(s) against other CBSAs. A list of comparison CBSAs can be predefined and serve as the default list of CBSAs to include in the comparison. The user can temporarily adjust the default list of CBSAs by adding or removing other target CBSAs from the list. The user can choose from the following parameters to compare PUF data for a hospital:

Year
  Viewing the comparison by AHW ($) or by Wage Index Values (%)
  Current year only, or include three years of historical data as well The comparison report includes a bar graph with the wage index value on the y-axis and the CBSAs selected on the x-axis. An exemplary CBSA comparison report is shown in FIG. 38.

The wage index navigator system can generate a comparison report of the top ten CBSAs. The report shows the top ten CBSAs ranked based on the amount of unadjusted salaries within a PUF data file. The system can automatically calculate and display the top ten CBSAs ranked in descending order by unadjusted salaries from the PUF data file selected. The user can choose month and year to determine which PUF data to use. Report columns will include:
  Numeric ranking
  CBSA name
  CBSA Number,
  Count of Providers,
  Total Salaries for the CBSA,
  Total Hours for the CBSA,
  AHW for each CBSA.

Figures 38, 39:
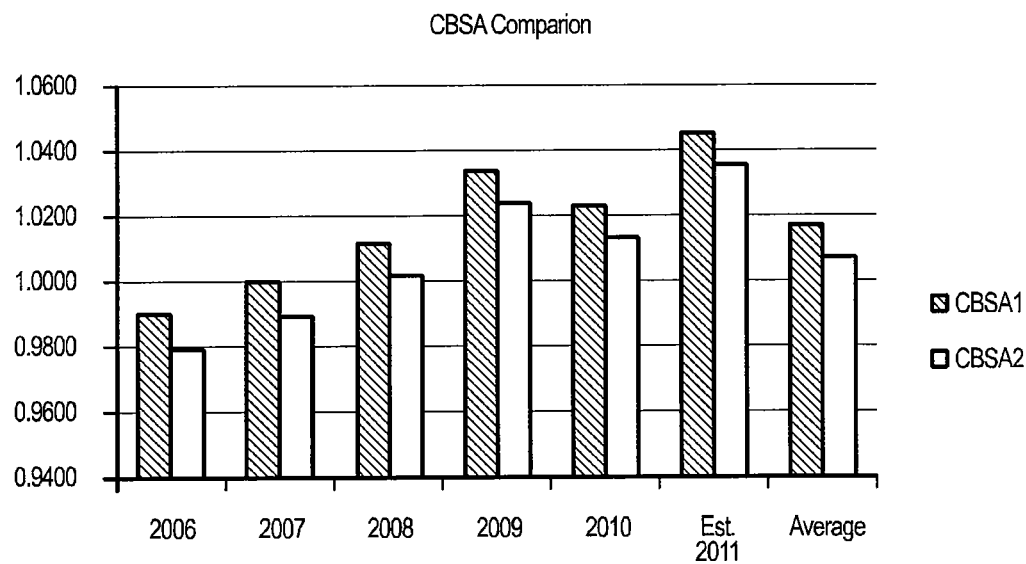
FIG. 38 shows an exemplary CBSA comparison report.
FIG. 39 shows an exemplary Top Ten CBSAs comparison report.

An exemplary Top Ten CBSAs comparison report is shown in FIG. 39.

The wage index navigator system can generate trending reports. The system can produce more accurate trending reports by allowing the reports to be generated after the February and May PUF files have been uploaded. Certain reports may not be available for a particular fiscal year until the appropriate data files have been released by CMS and imported. The trending report allows the user to select between viewing results by CBSA or for a target hospital within a CBSA. The user first selects a CBSA followed by a particular hospital within the CBSA, if desired. The trending reports rely on data from the PUF and the Federal Register tables. The system provides the capability to view the average hourly wage (dollars) by CBSA over time compared to other CBSAs and compared to the national average over time. The system enables an authorized user to view the average hourly wage index (dollars) trending for a given hospital year-over-year along with the CBSA average and compared to the national average over time. The trending report can show the average hourly wage index (ratio) by CBSA over time. The trending report can show the hours by CBSA along with the CBSA average compared to the national average over time. The trending report can show Exhibit 6 values for a hospital by line over time. The report can include a summary total at the bottom. The trending report can show benefits percent against salaries by hospital over time. A trending report can also be generated that shows the initial to final average hourly wage. An exemplary trending report is shown in FIG. 40.

Figure 41:
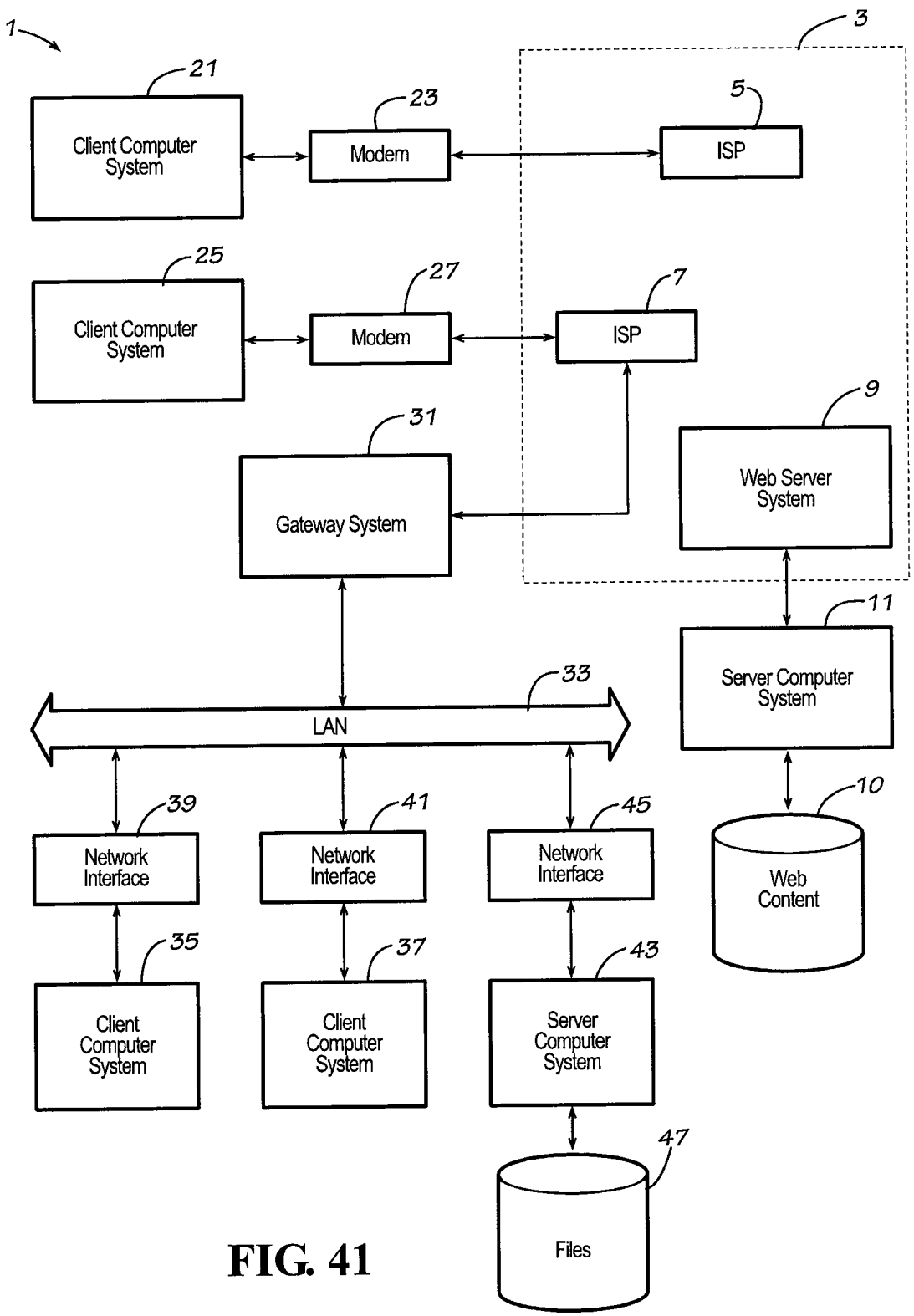
FIG. 41 shows an exemplary operating environment comprising several computer systems that are coupled together through a network.
Figure 42:
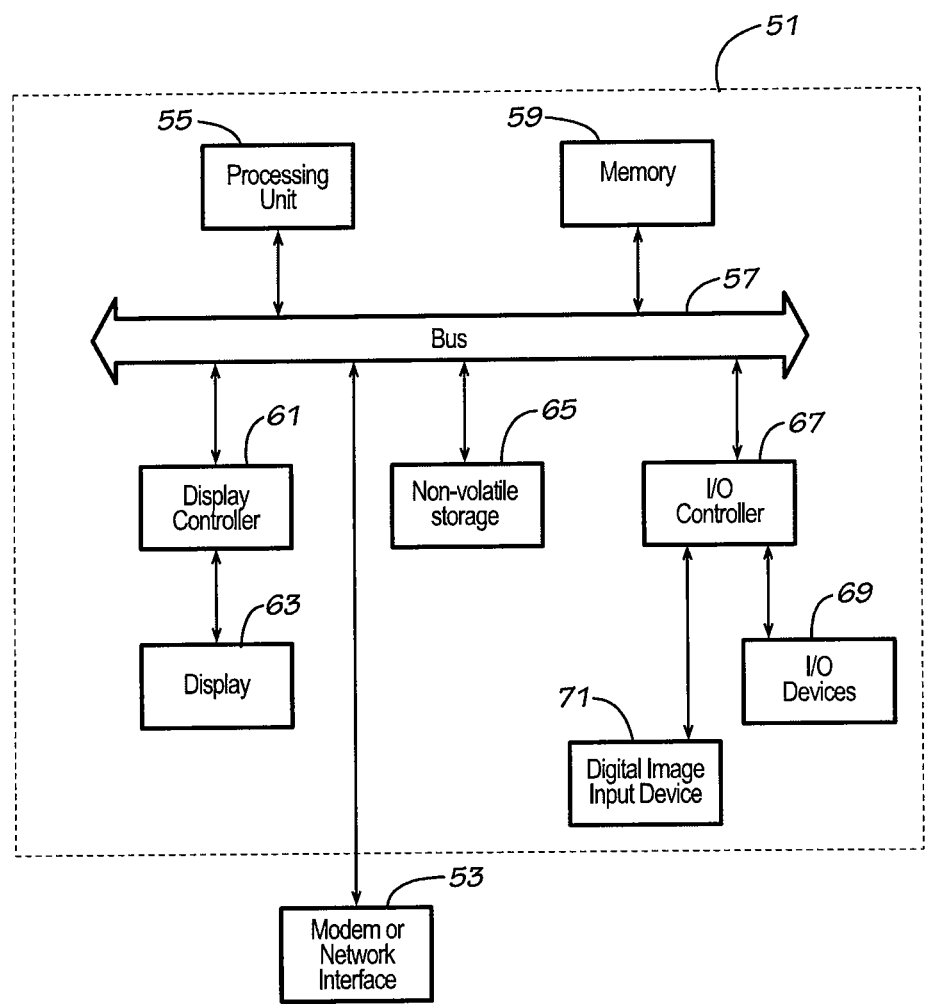
FIG. 42 shows an exemplary computer system that can be used as a client computer system or a server computer system or as a web server system.

The following description of FIGS. 41 and 42 are intended to provide an overview of computer hardware and other operating components suitable for performing the methods of the invention described above. However, it is not intended to limit the applicable environments. One of skill in the art will immediately appreciate that the invention can be practiced with other computer system configurations, including hand-held devices, multiprocessor systems, microprocessor-based or programmable consumer electronics, network PCs, minicomputers, mainframe computers, and the like. The invention can also be practiced in distributed computing environments where tasks are performed by remote processing devices that are linked through a communications network, such as a local area network (LAN), wide-are network (WAN), or over the Internet.

FIG. 41 shows several computer systems 1 that are coupled together through a network 3, such as the Internet. The term "Internet" as used herein refers to a network of networks which uses certain protocols, such as the TCP/IP protocol, and possibly other protocols such as the hypertext transfer protocol (HTTP) for hypertext markup language (HTML) documents that make up the World Wide Web (web). The physical connections of the Internet and the protocols and communication procedures of the Internet are well known to those of skill in the art. Access to the Internet 3 is typically provided by Internet service providers (ISP), such as the ISPs 5 and 7. Users on client systems, such as client computer systems 21, 25, 35, and 37 obtain access to the Internet through the Internet service providers, such as ISPs 5 and 7. Access to the Internet allows users of the client computer systems to exchange information, receive and send e-mails, and view documents, such as documents which have been prepared in the HTML format. These documents are often provided by web servers, such as web server 9 which is considered to be "on" the Internet. Often these web servers are provided by the ISPs, such as ISP 5, although a computer system can be set up and connected to the Internet without that system being also an ISP as is well known in the art.

The web server 9 is typically at least one computer system which operates as a server computer system and is configured to operate with the protocols of the World Wide Web and is coupled to the Internet. Optionally, the web server 9 can be part of an ISP which provides access to the Internet for client systems. The web server 9 is shown coupled to the server computer system 11 which itself is coupled to web content 10, which can be considered a form of a media database. It will be appreciated that while two computer systems 9 and 11 are shown in FIG. 41, the web server system 9 and the server computer system 11 can be one computer system having different software components providing the web server functionality and the server functionality provided by the server computer system 11 which will be described further below.

Client computer systems 21, 25, 35, and 37 can each, with the appropriate web browsing software, view HTML pages provided by the web server 9. The ISP 5 provides Internet connectivity to the client computer system 21 through the modem interface 23 which can be considered part of the client computer system 21. The client computer system can be a personal computer system, a network computer, a Web TV system, a handheld device, for example a smart phone, or other such computer system. Similarly, the ISP 7 provides Internet connectivity for client systems 25, 35, and 37, although as shown in FIG. 41, the connections are not the same for these three computer systems. Client computer system 25 is coupled through a modem interface 27 while client computer systems 35 and 37 are part of a LAN. While FIG. 41 shows the interfaces 23 and 27 as generically as a "modem," it will be appreciated that each of these interfaces can be an analog modem, ISDN modem, cable modem, satellite transmission interface, or other interfaces for coupling a computer system to other computer systems. Client computer systems 35 and 37 are coupled to a LAN 33 through network interfaces 39 and 41, which can be Ethernet network or other network interfaces. The LAN 33 is also coupled to a gateway computer system 31 which can provide firewall and other Internet related services for the local area network. This gateway computer system 31 is coupled to the ISP 7 to provide Internet connectivity to the client computer systems 35 and 37. The gateway computer system 31 can be a conventional server computer system. Also, the web server system 9 can be a conventional server computer system.

Alternatively, as well-known, a server computer system 43 can be directly coupled to the LAN 33 through a network interface 45 to provide files 47 and other services to the clients 35, 37, without the need to connect to the Internet through the gateway system 31.

FIG. 42 shows one example of a conventional computer system that can be used as a client computer system or a server computer system or as a web server system. It will also be appreciated that such a computer system can be used to perform many of the functions of an Internet service provider, such as ISP 5. The computer system 51 interfaces to external systems through the modem or network interface 53. It will be appreciated that the modem or network interface 53 can be considered to be part of the computer system 51. This interface 53 can be an analog modem, ISDN modem, cable modem, token ring interface, satellite transmission interface, or other interfaces for coupling a computer system to other computer systems. The computer system 51 includes a processing unit 55, which can be a conventional microprocessor such as an microprocessors made by Intel or AMD. Memory 59 is coupled to the processor 55 by a bus 57. Memory 59 can be dynamic random access memory (DRAM) and can also include static RAM (SRAM) or can be one of various other memory types known in the art. The bus 57 couples the processor 55 to the memory 59 and also to non-volatile storage 65 and to display controller 61 and to the input/output (I/O) controller 67. The display controller 61 controls a display on a display device 63 which can be a cathode ray tube (CRT), liquid crystal display (LCD) or other type of display device. The input/output devices 69 can include a keyboard, disk drives, printers, a scanner, and other input and output devices, including a mouse or other pointing device. The display controller 61 and the I/O controller 67 can be implemented with conventional well known technology. A digital image input device 71 can be a digital camera which is coupled to an I/O controller 67 in order to allow images from the digital camera to be input into the computer system 51. The non-volatile storage 65, an example of a "computer-readable storage medium" and a "machine-readable storage medium", is often a magnetic hard disk, an optical disk, or another form of storage for large amounts of data. Some of this data is often written, by a direct memory access process, into memory 59 during execution of software in the computer system 51. One of skill in the art will immediately recognize that the terms "computer-readable medium" and "machine-readable medium" include any type of "computer-readable storage medium" and "machine-readable storage medium" (e.g., storage device) that is accessible by the processor 55.

It will be appreciated that the computer system 51 is one example of many possible computer systems which have different architectures. For example, personal computers based on an Intel microprocessor often have multiple buses, one of which can be an input/output (I/O) bus for the peripherals and one that directly connects the processor 55 and the memory 59 (often referred to as a memory bus). The buses are connected together through bridge components that perform any necessary translation due to differing bus protocols.

Network computers are another type of computer system that can be used with the present invention. Network computers do not usually include a hard disk or other mass storage, and the executable programs are loaded from a network connection into the memory 59 for execution by the processor 55. A Web TV system, which is known in the art, is also considered to be a computer system according to the present invention, but it may lack some of the features shown in FIG. 42, such as certain input or output devices. A typical computer system will usually include at least a processor, memory, and a bus coupling the memory to the processor.

It will also be appreciated that the computer system 51 is controlled by operating system software which includes a file management system, such as a disk operating system, which is part of the operating system software. One example of an operating system software with its associated file management system software is the Windows family of operating systems from Microsoft Corporation of Redmond, Wash., and their associated file management systems. The file management system is typically stored in the non-volatile storage 65 and causes the processor 55 to execute the various acts required by the operating system to input and output data and to store data in memory, including storing files on the non-volatile storage 65.

The wage index navigator system also includes various system tools for configuring and utilizing the system. The system can be configured as a web-based application that operates on a web browser, for example Microsoft Internet Explorer or Firefox. The system can include available online contextual help for each page. The help pages can be maintained without programming intervention. The help text can be edited and controlled by a system administrator. The system preserves user defined preferences and data between version updates. User activity tracking scripts can be incorporated in to the system to allow for monitoring system performance and user behaviors over time. The activity tracking can be used to report on items such as amount of overall traffic, unique visitors, average number of items per visit, and other items. Note: this is for tracking the overall activity within the system and not about identifying specifically what a particular user has done.

Reports will default to display the following where applicable: Provider Name, Provider Number, Provider's fiscal year end date applicable to the Federal fiscal year, Geographic CBSA, Reclass/Redesignated CBSA, Federal fiscal year under review, and Date the report was generated.

The system includes an Administrator Console to outline the different organizations in the system and how the system can be administered. An authorized administrator manages user, organization and global settings. A Health System or hospital administrator manages preferences and settings which apply to their organization and users who are members of their organization. The system enables an administrative user to upload a public use file associated with a specific period and federal fiscal year. The system keeps an audit log of all email messages sent by the system. The system provides a console for viewing error and other debugging related messages generated by the system. There is a setting for each calendar year that allows an authorized administrator to enter the deadline for completing the wage index review process steps. Various parts of the system will be tied to entry dates and not allowed if outside that date. For example, impact reports not available at certain times or changes to the wage index process outside of the cutoff date. The administrative functionality related to administration of system data such as hospital profiles, health system profiles, CBSAs, and fiscal intermediaries will be available through the administrator console.

The wage index navigator system can support an organizational hierarchy with a number of different types of organizations represented within the system. The system supports multiple types of Organizations; "Health System", "Hospital", and "Fiscal Intermediary." Only an authorized administrator is allowed to create a new organization, or allowed to assign any organization's initial administrator. Hospitals can be associated to a Health System organization. A Health System can have one or many hospitals associated to it, but a hospital is only associated to one Health System. Each hospital is assigned a national provider number that is used to identify hospitals by CMS. The system stores the provider number associated with each hospital. Each hospital has a service type assigned which indicates which hospitals are receiving wage index review services (along with the type of service) and which are not in order to allow for benefit reporting used to promote the tool. The report will show providers grouped by service type.

The core based statistical area (CBSA) defines the geographic boundaries in which each hospital's wage index is reported and considered. The system includes an administrative console for maintaining a list of core based statistical areas with a unique identifier, and a name. Each hospital has a property indicating the core based statistical area to which it is assigned. An authorized administrator will be able to edit the CBSA to which a particular hospital is assigned. In addition, for multi-campus hospitals with campuses in different CBSAs, an authorized administrator will have the ability to enter the split percentages applicable to each CBSA. Each hospital can only be assigned to a single CBSA from the list of available CBSAs. The CBSA assignment may change from year to year through reclassification. The system supports the ability for a hospital to be assigned to a CBSA one year and a different CBSA the next year. The system can utilize the "Final Rule and Correction Notice" file to mass import the hospital and CBSA assignment data.

The fiscal intermediary (FI) is responsible for review of the wage index reporting as a gatekeeper prior to CMS. Each hospital is assigned to a FI. The system includes an administrative console to allow an authorized administrator to maintain a list of Fiscal Intermediaries with the following attributes: FI Name, Contact person name, Email address for contact, and Mailing address to send any hard copy (printed) results. Hospitals have an assigned FI to which their wage index review results can be electronically sent via email. The system provides an administrative console for an authorized administrator to change the FI assignments of a particular hospital.

The system maintains user profiles to identify and manage the attributes of each user in the system. The user profile can be configured to display a dashboard of 'activity' on the following items: wage index questions the user needs to answer for the current year, wage index questions the user has previously answered, and available reports. A user can manage or view password changes and security question updates in their user profile.

The system uses User Registration to determine how users gain access to the system. Each system role has a unique registration process. An authorized administrator creates an organization and an administrative account associated with the organization. The following information can be collected during the user setup process: First Name, Last Name, Email (double-entered), Username and Password (double-entered). Upon first login to the system the user can choose from a number of pre-determined security questions and provide answers. The security questions can then be used to secure password reset and other self service capability. Security Questions are typically pre-defined and answers not case-sensitive. New users of the system can be required to agree to a 'Terms of Use' agreement prior to using a new account. The 'Terms of Use' agreement includes verbiage about file uploads, and referencing copyrighted material. Administrator accounts associated with an organization will have the ability to create additional user accounts associated with the organization.

The system can incorporate a bulletin board-like component for the purpose of posting and viewing announcements. Announcements are a one way communication with no means to respond. Only authorized users with the appropriate permissions have the ability to create or edit an announcement. The announcements component displays as a part of the landing area a user sees when they first login to the system. When a new announcement is posted, a Title, Description, and Expiration Date is collected. The expiration date can start at a default value, for example two weeks. Text entry can be limited, for example 250 characters in the title. The text allows and displays hyperlinks. The system collects the Created By user, and a Created On date and/or Published Date. An announcement automatically expires after the specified expiration date. An expired announcement is no longer displayed. All expired announcements can be purged from the system after a designated period, for example one year from the date of expiration.

The system can employ security measures, for example SSL data encryption for pages that require a logged in user to view the content to protect data in transit, time-outs for inactive logged in users, password strength requiring a combination of letters and numbers and length of six or more characters, forgotten username retrieval process and password reset process, temporary account lock-outs based on a configurable amount of failed logins, and making users change their password on a configurable interval. The system typically require a user of the system to enter credentials before accessing data related to an association, health system, or hospital. The user is required to enter credentials only one time to access protected data until their session times out or they log out. The system can record an audit trail of all user login activity. Each user is intended to have a user account of their own and not share user accounts. The system requires each user to have a unique account name, and each account is associated with a unique email address. All user data can be stored in the application database to ensure that it is properly backed up and included in the disaster recovery readiness.

The system can support various system roles. Each user is assigned to a system role. Each system role has distinct permissions and access to functionality. The roles can include a system administrator that oversees the configuration and maintenance of the system. There can be different levels of system administrator, and different system administrators for different facilities. A reimbursement director that is responsible for completing the wage index review for one or more hospitals. Hospitals assigned to a reimbursement director may belong in one or more CBSAs. A hospital coordinator that is responsible for completing all or portions of the wage index review for a particular hospital. A fiscal intermediary that performs a desk review of the wage index. A fiscal intermediary will typically receive the materials via email and not access the system directly.

Permissions can be assigned to each of the system roles. Exemplary permission levels can include:
  No Access—A user that has not explicitly been granted any access within the application
  Reviewer—A user that has the ability to review the wage index review data for one or more hospitals and can make edits
  Owner—Owner that is responsible for completing the wage index review process for at least one hospital. The owner is responsible for ensuring the completion of the wage index review and signing off on the final version Delegate—A user that has been delegated a portion or all of the wage index review process. This user can provide data input, but cannot finalize the wage index data input An authorized system administrator can search and find any user of the system. The administrator can search by organization, name or username. The administrator can force a password change on a user, inactivate or "lock-out" a user from the system, and set the number of times a user can fail login before the system temporary inactivates or locks out their account. Accounts that are locked out because the number of failed logins has exceeded can be automatically re-enabled after a configurable timeout period.

A user can change their password at any point in time independent of the process that forces a user to change their password. A system administrator can promote existing user accounts to the different user roles, for example administrator, reimbursement director, or hospital coordinator. An administrator can be authorized to temporarily set a user's password, at which time the system shall enforce a password change on the next login.

A health system administrator role can be configured. The health system administrator can: manage members list (allow or disallow membership to an individual user); assign permissions/roles to other users that are members of the health system; act on behalf of a hospital administrator, perform any action a hospital administrator can do; and unlock a temporarily inactivated account.

A hospital administrator role can be configured. A hospital administrator can: manage members list (allow or disallow membership to an individual user), assign permissions/roles to other users that are members of the hospital, and unlock a temporarily inactivated account.

The system enables a user to retrieve a forgotten username and/or password. For forgotten usernames, the user is usually required to enter the email address they used to create the account. If the email address is found, the system shall email the user their username. For forgotten passwords, the user is usually required to enter their username, email and answer the three security questions they created during registration. If the information is verified the user is prompted on screen to create a new password. The system then generates an email to the email on file notifying the user that the password was changed; but not including the password.

While exemplary embodiments incorporating the principles of the present invention have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains.

We claim:

1. A healthcare wage index reporting method for use on a computer having a processor and a memory, the healthcare wage index reporting method comprising:
   providing questions and tasks through an electronic user interface to collect information regarding one or more hospitals for filling out a wage index and occupational mix report;
   electronically receiving hospital-related responses to the questions and tasks and storing the hospital-related responses in the memory, the hospital-related responses including the information regarding the one or more hospitals;
   processing the hospital-related responses using the processor to complete the wage index and occupational mix report;
   receiving and processing a public use file;
   comparing data in the public use file against data in the wage index and occupational mix report;
   checking the hospital-related responses using the processor to detect inconsistencies or errors;
   generating notices of detected inconsistencies or errors in the wage index and occupational mix report, wherein notices of inconsistencies or errors in the wage index and occupational mix report are generated in response to rules regarding the proper entries of expenses and administrative time that should be included in reporting and in response to rules regarding expenses that are applicable to excluded areas that should not be included in reporting;
   tracking progress in completing the wage index and occupational mix report; and
   generating a completed wage index and occupational mix report for submission to a recipient.

2. The healthcare wage index reporting method of claim 1, further comprising:
   separating the wage index and occupational mix report into a plurality of sections;
   delegating each of the plurality of sections to a coordinator for completion;
   for each completed section of the plurality of sections, compiling the information from the completed section to complete the wage index and occupational mix report.

3. The healthcare wage index reporting method of claim 2, further comprising:
   for each delegated section, tracking the progress toward completion of the delegated section,
   displaying a progress monitor showing the progress toward completion of each delegated section;
   for each delegated section, generating a notification message when the delegated section is completed.

4. The healthcare wage index reporting method of claim 1, wherein providing tasks to collect information includes instructing a user to import an electronic data file,
   wherein receiving responses to the tasks includes storing the data in the imported electronic data file in memory; and
   wherein processing the responses includes processing the data from the imported electronic data file to complete the wage index and occupational mix report.

5. The healthcare wage index reporting method of claim 4, wherein the electronic data file is a wage index and occupational mix public use file (PUF).

6. The healthcare wage index reporting method of claim 4, further comprising pre-populating responses based on the electronic data file.

7. The healthcare wage index reporting method of claim 4, further comprising generating notifications of differences between information in the wage index and occupational mix report and information received from the electronic data file.

8. The healthcare wage index reporting method of claim 7, wherein a notification is only generated when the difference between information in the wage index and occupational mix report and information received from the electronic data file exceeds a threshold for that response.

9. The healthcare wage index reporting method of claim 1, wherein the recipient is a fiscal intermediary that communicates with the Centers for Medicare and Medicaid Services (CMS).

10. The healthcare wage index reporting method of claim 1, further comprising displaying a dashboard showing progress of completing the wage index and occupational mix report, and current results for the wage index and occupational mix report.

11. The healthcare wage index reporting method of claim 1, wherein generating notices of detected inconsistencies or errors comprises:
   automatically notifying a user of a detected error; and
   not permitting progress in the wage index reporting process until the detected error is corrected.

12. The healthcare wage index reporting method of claim 1, further comprising:
   providing a user-selectable link to more detailed instructions for responding to a particular question or task; and
   displaying more detailed instructions for responding to the particular question or task when the user-selectable link is selected.

13. The healthcare wage index reporting method of claim 12, wherein the more detailed instructions include a series of questions for deriving the desired response to the particular question or task.

14. The healthcare wage index reporting method of claim 1, further comprising
   providing a workpaper template for collecting the supporting information for a particular response to a question or task;
   accepting and storing entries in the workpaper template; and
   attaching the workpaper template to an appropriate portion of the wage index and occupational mix report.

15. The healthcare wage index reporting method of claim 1, further comprising:
   validating the completed wage index and occupational mix report before submission; and
   protecting the validated wage index and occupational mix report from further modification.

16. The healthcare wage index reporting method of claim 1, further comprising:
   uploading audited financial statements; and
   reconciling the wage index and occupational mix report against the uploaded audited financial statements.

17. The healthcare wage index reporting method of claim 1, further comprising:
   generating prompts based on responses to the questions and tasks; and
   displaying the prompts as part of future questions and tasks provided to collect information for filling out a wage index and occupational mix report.

18. The healthcare wage index reporting method of claim 1, further comprising:
   determining future questions and tasks to be provided based upon responses to previous questions and tasks.

19. The healthcare wage index reporting method of claim 1, further comprising:
   generating a user-requested impact report showing the impact of proposed changes to the wage index and occupational mix report.

20. The healthcare wage index reporting method of claim 19, wherein the impact report is generated for a selected core based statistical area (CBSA).

21. The healthcare wage index reporting method of claim 1, further comprising:
   generating a user-requested county reclassification summary report showing the financial impact of county reclassification within a core based statistical area (CBSA).

22. The healthcare wage index reporting method of claim 1, further comprising:
   receiving user messages for posting on a system bulletin board;
   receiving bulletin board responses responding to posted messages on the system bulletin board;
   associating each bulletin board response with the appropriate posted message; and
   deleting each posted message and any associated responses after a designated time period.

23. A healthcare wage index reporting system comprising:
   an electronic user interface for providing questions and tasks to collect information regarding one or more hospitals for filling out a wage index and occupational mix report, and for receiving hospital-related responses to the questions and tasks including receiving a public use file, the hospital-related responses including the information regarding the one or more hospitals;
   a processor for processing the hospital-related responses to complete the wage index and occupational mix report;
   a validation module for comparing data in the public use file against data in the wage index and occupational mix report and for checking the hospital-related responses to detect inconsistencies or errors in the wage index and occupational mix report, and for generating notices of detected inconsistencies or errors in the wage index and occupational mix report, wherein notices of inconsistencies or errors in the wage index and occupational mix report are generated in response to rules regarding the proper entries of expenses and administrative time that should be included in reporting and expenses that are applicable to excluded areas that should not be included in reporting;
   an electronic dashboard for tracking progress in completing the wage index and occupational mix report; and
   a finalization module for generating a completed wage index and occupational mix report for submission to a recipient.

24. The healthcare wage index reporting system of claim 23, wherein
   the electronic user interface imports electronic data files and stores the imported data files in memory; and
   wherein the processor processes the data from the imported electronic data files to complete the wage index and occupational mix report.

25. The healthcare wage index reporting system of claim 24, wherein the processor pre-populates responses based on the electronic data file.

26. The healthcare wage index reporting system of claim 24, wherein the validation module generates notifications of differences between information in the wage index and occupational mix report and information received from the electronic data file.

27. The healthcare wage index reporting system of claim 23, wherein the validation module automatically notifies a user of a detected error; and prevents further progress in the wage index reporting process until the detected error is corrected.

28. The healthcare wage index reporting system of claim 23, further comprising a help module for providing more detailed instructions for responding to the particular question or task when a user-selectable link is selected.

29. The healthcare wage index reporting system of claim 23, wherein the electronic user interface displays templates for collecting data and preparing workpapers to support a particular response to a question or task.

30. The healthcare wage index reporting system of claim 23, wherein the finalization module validates the completed wage index and occupational mix report before submission; protects the validated wage index and occupational mix report from further modification, and electronically submits the completed wage index and occupational mix report to the recipient.

31. The healthcare wage index reporting system of claim 23, wherein the processor generates prompts based on responses to the questions and tasks; and the electronic user interface displays the prompts as part of future questions and tasks provided to collect information for filling out a wage index and occupational mix report.

32. The healthcare wage index reporting system of claim 23, further comprising a report module for generating a user-requested impact report showing the impact of proposed changes to the wage index and occupational mix report.

33. The healthcare wage index reporting system of claim 23, wherein the finalization module selects supporting documentation to be submitted with the completed wage index and occupational mix report.

\* \* \* \* \*